US006004777A

United States Patent [19]

Tartaglia et al.

[11] Patent Number: 6,004,777

[45] Date of Patent: Dec. 21, 1999

[54] VECTORS HAVING ENHANCED EXPRESSION, AND METHODS OF MAKING AND USES THEREOF

[75] Inventors: James Tartaglia, Schenectady, N.Y.; Bertram L. Jacobs, Phoenix, Ariz.; Scott J. Goebel, Ballston Spa, N.Y.; William I. Cox, Sand Lake, N.Y.; Russell Robert Gettig, Averill Park, N.Y.; Steven E. Pincus, East Greenbush, N.Y.; Enzo Paoletti, Delmar, N.Y.

[73] Assignees: Virogenetics Corporation, Troy, N.Y.; Arizona State University, Tempe, Ariz.

[21] Appl. No.: 08/815,809

[22] Filed: Mar. 12, 1997

[51] Int. Cl.[6] .......................... C12P 21/00; C12N 15/63; C12N 15/66; C12N 15/11

[52] U.S. Cl. ................. 435/69.1; 435/91.41; 435/320.1; 536/23.1; 536/23.72

[58] Field of Search .............................. 435/69.1, 91.41, 435/320.1; 536/23.1, 23.72

[56] References Cited

U.S. PATENT DOCUMENTS 5,494,807 2/1996 Paoletti et al. .

OTHER PUBLICATIONS

Piccini et al. Vaccinia Virus as an Expression Vector. Methods in Enzymology vol. 153 pp. 545–563, 1987.

Beattie et al. Journal of Virology, vol. 69, No. 1, Jan. 1995, pp. 499–505.

Ahn, B–Y. and Moss, B. 1992. RNA polymerase–associated transcription specificity factor encoded by vaccinia virus. Proc. Natl. Acad. Sci. 89: 3536–3540.

Beattie, E., Paoletti, E., and Tartaglia, J. 1995. Distinct Patterns of IFN Sensitivity Observed in Cells Infected with Vaccinia K3L and E3L Mutant Viruses. Virology 210:254–263.

Beattie, E., Tartaglia, J. and Paoletti, E. 1991, Vaccinia virus–encoded eIF–2a homologue abrogates the antiviral effect of interferon. Virology 183: 419–422.

Carroll, K., Elroy Stein, O., Moss, B. and Jagus, R. 1993. Recombinant vaccinia virus K3L gene product prevents activation of double–stranded RNA–dependent, initiation factor 2 alpha–specific protein kinase. J. Biol. Chem. 268: 12837–12842.

Chang, H–W., Watson, J. and Jacobs, B. L. 1992. The vaccinia virus E3L gene encodes a double–stranded RNA–binding protein with inhibitory activity for the interferon–induced protein kinase. Proc. Natl. Acad. Sci. USA 89: 4825–4829.

Clark, P. A., Schwemmle, M., Schickinger, J., Hilse, K., and Clemens, M. J. 1991. Binding of Epstein–Barr virus small RNA EBER–1 to double–stranded RNA–activated protein kinase DAI. Nucleic Acids Res. 19:243–248.

Davies. M. V., Chang, H. W. , Jacobs, B. L. and Kaufman, R. J. 1993. The E3L and K3L vaccinia virus gene products stimulate translation through inhibition of the double–stranded RNA–dependent protein kinase by different mechanisms. J. Virol. 67: 1688–1692.

Davies, M. V., Elroy Stein, O., Jagus, R., Moss, B. and Kaufman, R. J. 1992. The vaccinia K3L gene product potentiates translation by inhibiting double–stranded–RNA–activated protein kinase and phosphorylation of the alpha subunit of eukaryotic initiation factor 2. J. Virol. 66: 1943–1950.

Goebel, S. J., Johnson, G. P., Perkus, M. E., Davis, S. W., Winslow, J. P. and Paoletti, E. 1990. The complete DNA sequence of vaccinia virus. Virology 179: 247–266.

Harlow, E. and Lane, D. (1988). Antibodies, A Laboratory Manual. Cold Spring Harbor Laboratory. 421–470.

Hattori, M., and Sakaki, Y. (1986). Dideoxy sequencing method using denatured plasmid templates. Anal. Biochem. 152, 232–237.

Imani, F. and Jacobs, B. L. 1988. Inhibitory activity for the interferon induced protein Kinase is associated with the reovirus serotype 1 s3 protein. Proc. Natl. Acad. Sci. USA 85: 7887–7891.

Jacobs, B. L. and Langland, J. O. 1996. When two strands are better than one: the mediators and modulators of the cellular responses to double–stranded RNA. Virology 219: 339–349.

Langone, J. (1982). Applications of immobilized protein A in immunochemical techniques. J. Immunol. Methods. 55. 277–296.

Mathews, M. B. and Shenk, T. 1991. Adenovirus virus–associated RNA and translation control. J. Virol. 65: 5657–5662.

(List continued on next page.)

*Primary Examiner*—John S. Brusca
*Attorney, Agent, or Firm*—Frommer Lawrence & Haug LLP; William S. Frommer; Thomas J. Kowalski

[57] ABSTRACT

Disclosed and claimed are vectors having enhanced expression and methods for making and using them. Enhancement of expression is from substantially co-temporal expression of at least one first nucleic acid molecule and at least one second nucleic acid molecule. The second nucleic acid molecule encodes a translation factor. The contemporaneous expression can be from operably linking the first and second nucleic molecules to a single promoter, or from operably linking the first nucleic acid molecule to a first promoter and the second nucleic molecule to a second promoter wherein the first and second promoters function substantially contemporaneously. Thus, the first and second nucleic acid molecules can be at the same locus in the vector or at different loci. The second nucleic acid molecule can encode encode one translation factor or more than one translation factor. The translation factor can be a K3L open reading frame, an E3L open reading frame, a VAI RNA, an EBER RNA, a sigma 3 open reading frame, a TRBP open reading frame, or combinations thereof. The vector can be a poxvirus such as an attenuated poxvirus; for instance, a NYVAC vaccinia virus or an ALVAC canarypox virus.

15 Claims, 24 Drawing Sheets

OTHER PUBLICATIONS

Moss, B. 1990. Regulation of vaccinia virus transcription. Annu. Rev. Biochem. 59: 661–688.

Moss, B. 1992. Molecular biology of poxviruses. In *Recombinant Poxviruses.* Binns M. M., Smith, G. L. (eds). Boca Raton, FL: CRC Press; pp. 45–80.

Park, H., Davies, M. V., Langland, L. O., Chang, H–W., Nam, Y. S., Tartaglia, J., Paoletti, E., Jacobs, B. L., Kaufman, R. J. and Venkatesan, S. 1994. Proc. Natl. Acad. Sci. USA 91: 4713–4717.

Perkus, M., Limbach, K., Paoletti, E. (1989). Cloning and expression of foreign genes in vaccinia virus, using a host range selection system. J. Virology 63. 3829–3836.

Perkus, M. E., Tartaglia, J., and Paoletti, E. 1995. Poxvirus–based vaccine candidates for cancer, AIDS and other infectious diseases. J. of Leukocyte Biology 58: 1–13.

Sharp, T. V., Schwemmle, M., Jeffrey, I., Laing, K., Mellor, H., Proud, C. G., Hilse, K. and Clemens, M. J. 1993. Comparative analysis of the regulation of the interferon–inducible protein kinase PKR Epstein–Barr virus RNAs EBER–1 and EBER–2 and adenovirus VAI RNA. Nucleic Acids Res. 21: 4483–4490.

Tabor, S., and Richardson, C.C. (1987). DNA sequence analysis with a modified bacteriophage T7 polymerase. Proc. Natl. Acad. Sci. USA 84, 4767–4771.

Tartaglia, J., Perkus, M. E., Taylor, J. et al. 1992. NYVAC: A highly attenuated strain of vaccinia virus. Virology 188: 217–232.

Thimmappaya, B. C., Weinberger, C., Schneider, R. J. and Shenk, T. 1982. Adenovirus VAI RNA is required for efficient translation viral mRNAs at late times after infection. Cell 31: 543–551.

Watson, J., Chang, H–W. and Jacobs, B. L. 1991. Characterization of a vaccinia virus–induced dsRNA–binding protein that may be the inhibitor of the dsRNA–dependent protein kinase. Virology 185: 206–216.

Yuen, L, and Moss, B. (1987). Oligonucleotide sequence signaling transcriptional termination of vaccinia virus early genes. Proc. Natl. Acad. Sci. USA 84, 6417–6421.

Zhang, Y., Ahn, B–Y. and Moss, B. 1994. Targeting of a multicomponent transcription apparatus into assembling vaccinia virus particles requires RAP94, an RNA polymerase–associated protein. J. Virol. 68: 1360–1370.

FIG. 1A

Nucleotide sequence of the ALVAC C6 insertion site containing the H6 / K3L and E3L expression cassette.

| Characteristic | Position(s) |
|---|---|
| Left Arm | 1-385 |
| Right Arm | 3273-4434 |
| K3L orf | C727-464 |
| H6 Promoter | C850-728 |
| E3L | C2758-2188 |

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCAG ATCTCTCGAG
 421 GTCGACGGTA TCGATAAGCT TGATATCGAA TTCATAAAAA TTATTGATGT CTACACATCC
 481 TTTTGTAATT GACATCTATA TATCCTTTTG TATAATCAAC TCTAATCACT TTAACTTTTA
 541 CAGTTTTCCC TACCAGTTTA TCCCTATATT CAACATATCT ATCCATATGC ATCTTAACAC
 601 TCTCTGCCAA GATAGCTTCA GAGTGAGGAT AGTCAAAAAG ATAAATGTAT AGAGCATAAT
 661 CCTTCTCGTA TACTCTGCCC TTTATTACAT CGCCCGCATT GGGCAACGAA TAACAAAATG
 721 CAAGCATACG ATACAAACTT AACGGATATC GCGATAATGA AATAATTTAT GATTATTTCT
 781 CGCTTTCAAT TTAACACAAC CCTCAAGAAC CTTTGTATTT ATTTTCACTT TTTAAGTATA
 841 GAATAAAGAA AGCTCTAATT AATTAATGAA CAGATTGTTT CGTTTTCCCC TTGGCGTATC
 901 ACTAATTAAT TAACCCGGGC TGCAGCTCGA GGAATTCAAC TATATCGACA TATTTCATTT
 961 GTATACACAT AACCATTACT AACGTAGAAT GTATAGGAAG AGATGTAACG GGAACAGGGT
1021 TTGTTGATTC GCAAACTATT CTAATACATA ATTCTTCTGT TAATACGTCT TGCACGTAAT
1081 CTATTATAGA TGCCAAGATA TCTATATAAT TATTTTGTAA GATGATGTTA ACTATGTGAT
1141 CTATATAAGT AGTGTAATAA TTCATGTATT TCGATATATG TTCCAACTCT GTCTTTGTGA
1201 TGTCTAGTTT CGTAATATCT ATAGCATCCT CAAAAAATAT ATTCGCATAT ATTCCCAAGT
1261 CTTCAGTTCT ATCTTCTAAA AAATCTTCAA CGTATGGAAT ATAATAATCT ATTTTACCTC
1321 TTCTGATATC ATTAATGATA TAGTTTTTGA CACTATCTTC TGTCAATTGA TTCTTATTCA
1381 CTATATCTAA GAAACGGATA GCGTCCCTAG GACGAACTAC TGCCATTAAT ATCTCTATTA
1441 TAGCTTCTGG ACATAATTCA TCTATTATAC CAGAATTAAT GGGAACTATT CCGTATCTAT
1501 CTAACATAGT TTTAAGAAAG TCAGAATCTA AGACCTGATG TTCATATATT GGTTCATACA
1561 TGAAATGATC TCTATTGATG ATAGTGACTA TTTCATTCTC TGAAAATTGG TAACTCATTC
1621 TATATATGCT TTCCTTGTTG ATGAAGGATA GAATATACTC AATAGAATTT GTACCAACAA
1681 ACTGTTCTCT TATGAATCGT ATATCATCAT CTGAAATAAT CATGTAAGGC ATACATTTAA
1741 CAATTAGAGA CTTGTCTCCT GTTATCAATA TACTATTCTT GTGATAATTT ATGTGTGAGG
1801 CAAATTTGTC CACGTTCTTT AATTTTGTTA TAGTAGATAT CAAATCCAAT GGAGCTACAG
1861 TTCTTGGCTT AAACAGATAT AGTTTTTCTG GAACAAATTC TACAACATTA TTATAAAGGA
1921 CTTTGGGTAG ATAAGTGGGA TGAAATCCTA TTTTAATTAA TGCTATCGCA TTGTCCTCGT
1981 GCAAATATCC AAACGCTTTT GTGATAGTAT GGCATTCATT GTCTAGAAAC GCTCTACGAA
2041 TATCTGTGAC AGATATCATC TTTAGAGAAT ATACTAGTCG CGTTAATAGT ACTACAATTT
2101 GTATTTTTTA ATCTATCTCA ATAAAAAAAT TAATATGTAT GATTCAATGT ATAACTAAAC
2161 TACTAACTGT TATTGATAAC TAGAATCAGA ATCTAATGAT GACGTAACCA AGAAGTTTAT
2221 CTACTGCCAA TTTAGCTGCA TTATTTTTAG CATCTCGTTT AGATTTTCCA TCTGCCTTAT
2281 CGAATACTCT TCCGTCGATG TCTACACAGG CATAAAATGT AGGAGAGTTA CTAGGCCCAA
2341 CTGATTCAAT ACGAAAAGAC CAATCTCTCT TAGTTATTTG GCAGTACTCA TTAATAATGG
2401 TGACAGGGTT AGCATCTTTC CAATCAATAA TTTTTTTAGC CGGAATAACA TCATCAAAAG
2461 ACTTATGATC CTCTCTCATT GATTTTTCGC GGGATACATC ATCTATTATG ACGTCAGCCA
```

FIG. 1B

2521 TAGCATCAGC ATCCGGCTTA TCCGCCTCCG TTGTCATAAA CCAACGAGGA GGAATATCGT
2581 CGGAGCTGTA CACCATAGCA CTACGTTGAA GATCGTACAG AGCTTTATTA ACTTCTCGCT
2641 TCTCCATATT AAGTTGTCTA GTTAGTTGTG CAGCAGTAGC TCCTTCGATT CCAATGTTTT
2701 TAATAGCCGC ACACACAATC TCTGCGTCAG AACGCTCGTC AATATAGATC TTAGACATTT
2761 TTAGAGAGAA CTAACACAAC CAGCAATAAA ACTGAACCTA CTTTATCATT TTTTTATTCA
2821 TCATCCTCTG GTGGTTCGTC GTTTCTATCG AATGTAGCTC TGATTAACCC GTCATCTATA
2881 GGTGATGCTG GTTCTGGAGA TTCTGGAGGA GATGGATTAT TATCTGGAAG AATCTCTGTT
2941 ATTTCCTTGT TTTCATGTAT CGATTGCGTT GTAACATTAA GATTGCGAAA TGCTCTAAAT
3001 TTGGGAGGCT TAAAGTGTTG TTTGCAATCT CTACACGCGT GTCTAACTAG TGGAGGTTCG
3061 TCAGCTGCTC TAGTTTGAAT CATCATCGGC GTAGTATTCC TACTTTTACA GTTAGGACAC
3121 GGTGTATTGT ATTTCTCGTC GAGAACGTTA AAATAATCGT TGTAACTCAC ATCCTTTATT
3181 TTATCTATAT TGTATTCTAC TCCTTTCTTA ATGCATTTTA TACCGAATAA GAGATAGCGA
3241 AGGAATTCTT TTTATTGATT AACTAGTCAA ATGAGTATAT ATAATTGAAA AAGTAAAATA
3301 TAAATCATAT AATAATGAAA CGAAATATCA GTAATAGACA GGAACTGGCA GATTCTTCTT
3361 CTAATGAAGT AAGTACTGCT AAATCTCCAA AATTAGATAA AAATGATACA GCAAATACAG
3421 CTTCATTCAA CGAATTACCT TTTAATTTTT TCAGACACAC CTTATTACAA ACTAACTAAG
3481 TCAGATGATG AGAAAGTAAA TATAAATTTA ACTTATGGGT ATAATATAAT AAAGATTCAT
3541 GATATTAATA ATTTACTTAA CGATGTTAAT AGACTTATTC CATCAACCCC TTCAAACCTT
3601 TCTGGATATT ATAAAATACC AGTTAATGAT ATTAAAATAG ATTGTTTAAG AGATGTAAAT
3661 AATTATTTGG AGGTAAAGGA TATAAAATTA GTCTATCTTT CACATGGAAA TGAATTACCT
3721 AATATTAATA ATTATGATAG GAATTTTTTA GGATTTACAG CTGTTATATG TATCAACAAT
3781 ACAGGCAGAT CTATGGTTAT GGTAAAACAC TGTAACGGGA AGCAGCATTC TATGGTAACT
3841 GGCCTATGTT TAATAGCCAG ATCATTTTAC TCTATAAACA TTTTACCACA AATAATAGGA
3901 TCCTCTAGAT ATTTAATATT ATATCTAACA ACAACAAAAA AATTTAACGA TGTATGGCCA
3961 GAAGTATTTT CTACTAATAA AGATAAAGAT AGTCTATCTT ATCTACAAGA TATGAAAGAA
4021 GATAATCATT TAGTAGTAGC TACTAATATG GAAAGAAATG TATACAAAAA CGTGGAAGCT
4081 TTTATATTAA ATAGCATATT ACTAGAAGAT TTAAAATCTA GACTTAGTAT AACAAAACAG
4141 TTAAATGCCA ATATCGATTC TATATTTCAT CATAACAGTA GTACATTAAT CAGTGATATA
4201 CTGAAACGAT CTACAGACTC AACTATGCAA GGAATAAGCA ATATGCCAAT TATGTCTAAT
4261 ATTTTAACTT TAGAACTAAA ACGTTCTACC AATACTAAAA ATAGGATACG TGATAGGCTG
4321 TTAAAAGCTG CAATAAATAG TAAGGATGTA GAAGAAATAC TTTGTTCTAT ACCTTCGGAG
4381 GAAAGAACTT TAGAACAACT TAAGTTTAAT CAAACTTGTA TTTATGAAGG TACC

FIG. 2

DNA sequence of the coding region of FHV gB with modified T5NT motifs.

```
   1 ATGTCCACTC GTGGCGATCT TGGGAAGCGG CGACGAGGGA GTCGTTGGCA GGGACACAGT
  61 GGCTATTTTC GACAGAGATG TTTTTTCCCT TCTCTACTCG GTATTGCAGC GACTGGCTCC
 121 AGACATGGTA ACGGATCGTC GGGATTAACC AGACTAGCTA GATATGTTTC ATTTATCTGG
 181 ATCGTACTAT TCTTAGTCGG TCCCCGTCCA GTAGAGGGTC AATCTGGAAG CACATCGGAA
 241 CAACCCCGGC GGACTGTAGC TACCCCTGAG GTAGGGGGTA CACCACCAAA ACCAACTACA
 301 GATCCCACCG ATATGTCGGA TATGAGGGAA GCTCTCCGTG CGTCCCAAAT AGAGGCTAAC
 361 GGACCATCGA CTTTCTATAT GTGTCCACCA CCTTCAGGAT CTACTGTCGT GCGTTTAGAG
 421 CCACCACGGG CCTGTCCAGA TTATAAACTA GGGAAAAATT TTACCGAGGG TATAGCTGTA
 481 ATATTTAAAG AAAATATAGC GCCATATAAA TTCAAGGCAA ATATATACTA TAAAAACATT
 541 ATTATGACAA CGGTATGGTC TGGGAGTTCC TATGCCGTTA CAACCAACCG ATATACAGAC
 601 AGGGTTCCCG TGAAAGTTCA AGAGATTACA GATCTCATAG ATAGACGGGG TATGTGCCTC
 661 TCGAAAGCTG ATTACGTTCG TAACAATTAT CAATTTACGG CCTTTGATCG AGACGAGGAT
 721 CCCAGAGAAC TGCCTCTGAA ACCCTCCAAG TTCAACACTC CAGAGTCCCG TGGATGGCAC
 781 ACCACCAATG AAACATACAC AAAGATCGGT GCTGCTGGAT TTCACCACTC TGGGACCTCT
 841 GTAAATTGCA TCGTAGAGGA AGTGGATGCA AGATCTGTAT ATCCATATGA CTCATTTGCT
 901 ATCTCCACTG GTGACGTGAT TCACATGTCT CCATTCTTTG GGCTGAGGGA TGGAGCCCAT
 961 GTAGAACATA CTAGTTATTC TTCAGACAGA TTTCAACAAA TCGAGGGATA CTATCCAATA
1021 GACTTGGATA CGCGATTACA ACTGGGGGCA CCAGTTTCTC GCAATTTTTT GGAAACTCCG
1081 CATGTGACAG TGGCCTGGAA CTGGACCCCA AAGTCTGGTC GGGTATGTAC CTTAGCCAAA
1141 TGGAGGGAAA TAGATGAAAT GCTACGCGAT GAATATCAGG GCTCCTATAG ATTTACAGCC
1201 AAGACCATAT CCGCTACTTT CATCTCCAAT ACTTCACAAT TTGAAATCAA TCGTATCCGT
1261 TTGGGGGACT GTGCCACCAA GGAGGCAGCC GAAGCCATAG ACCGGATTTA TAAGAGTAAA
1321 TATAGTAAAA CTCATATTCA GACTGGAACC CTGGAGACCT ACCTAGCCCG TGGGGGATTT
1381 CTAATAGCTT TCCGTCCCAT GATCAGCAAC GAACTAGCAA AGTTATATAT CAATGAATTA
1441 GCACGTTCCA ATCGCACGGT AGATCTCAGT GCACTCCTCA ATCCATCTGG GGAAACAGTA
1501 CAACGAACTA GAAGATCGGT CCCATCTAAT CAACATCATA GGTCGCGGCG CAGCACAATA
1561 GAGGGGGGTA TAGAAACCGT GAACAATGCA TCACTCCTCA AGACCACCTC ATCTGTGGAA
1621 TTCGCAATGC TACAATTTGC CTATGACTAC ATACAAGCCC ATGTAAATGA AATGTTGAGT
1681 CGGATAGCCA CTGCCTGGTG TACACTTCAG AACCGCGAAC ATGTGCTGTG GACAGAGACC
1741 CTAAAACTCA ATCCCGGTGG GGTGGTCTCG ATGGCCCTAG AACGTCGTGT ATCCGCGCGC
1801 CTACTTGGAG ATGCCGTCGC CGTAACACAA TGTGTTAACA TTTCTAGCGG ACATGTCTAT
1861 ATCCAAAATT CTATGCGGGT GACGGGTTCA TCAACGACAT GTTACAGCCG CCCTCTTGTT
1921 TCCTTCCGTG CCCTCAATGA CTCCGAATAC ATAGAAGGAC AACTAGGGGA AAACAATGAA
1981 CTTCTCGTGG AACGAAAACT AATTGAGCCT TGCACTGTCA ATAATAAGCG GTATTTTAAG
2041 TTTGGGGCAG ATTATGTATA TTTTGAGGAT TATGCGTATG TCCGTAAAGT CCCGCTATCG
2101 GAGATAGAAC TGATAAGTGC GTATGTGAAT TTAAATCTTA CTCTCCTAGA GGATCGTGAA
2161 TTTCTCCCAC TCGAAGTTTA TACACGAGCT GAGCTGGAAG ATACCGGCCT TTTGGACTAC
2221 AGCGAGATTC AACGCCGCAA CCAACTCCAC GCCTTAAAAT TTTATGATAT AGACAGCATA
2281 GTCAGAGTGG ATAATAATCT TGTCATCATG CGTGGTATGG CAAATTTCTT TCAGGGACTC
2341 GGGGATGTGG GGGCTGGTTT CGGCAAGGTG GTCTTAGGGG CTGCGAGTGC GGTAATCTCA
2401 ACAGTATCAG GCGTATCATC ATTTCTAAAC AACCCATTTG GAGCATTGGC CGTGGGACTG
2461 TTAATATTAG CTGGCATCGT CGCAGCATTC CTGGCATATC GCTATATATC TAGATTACGT
2521 GCAAATCCAA TGAAAGCCTT ATATCCTGTG ACGACTAGGA ATTTGAAACA GACGCTAAGA
2581 GCCCGCTCAA CGGCTGGTGG GGATAGCGAC CCGGGAGTCG ATGACTTCGA TGAGGAAAAG
2641 CTAATGCAGG CAAGGGAGAT GATAAAATAT ATGTCCCTCG TATCGGCTAT GGAGCAACAA
2701 GAACATAAGG CGATGAAAAA GAATAAGGGC CCAGCGATCC TAACGAGTCA TCTCACTAAC
2761 ATGGCCCTCC GTCGCCGTGG ACCTAAATAC CAACGCCTCA ATAATCTTGA TAGCGGTGAT
2821 GATACTGAAA CAAATCTTGT CTAA
```

FIG. 3A

DNA sequence of the the H6 promoted FHV gB donor plasmid pC3H6FHVB.

H6 promoter: 3958 - 3835

FHV gB coding region: 3834 - 991

C3 left arm: 15 - 939

C3 right arm: 4056 - 6628

```
   1 GCGGCCGCGT CGACATGCAT TGTTAGTTCT GTAGATCAGT AACGTATAGC ATACGAGTAT
  61 AATTATCGTA GGTAGTAGGT ATCCTAAAAT AAATCTGATA CAGATAATAA CTTTGTAAAT
 121 CAATTCAGCA ATTTCTCTAT TATCATGATA ATGATTAATA CACAGCGTGT CGTTATTTTT
 181 TGTTACGATA GTATTTCTAA AGTAAAGAGC AGGAATCCCT AGTATAATAG AAATAATCCA
 241 TATGAAAAAT ATAGTAATGT ACATATTTCT AATGTTAACA TATTTATAGG TAAATCCAGG
 301 AAGGGTAATT TTTACATATC TATATACGCT TATTACAGTT ATTAAAAATA TACTTGCAAA
 361 CATGTTAGAA GTAAAAAAGA AAGAACTAAT TTTACAAAGT GCTTTACCAA AATGCCAATG
 421 GAAATTACTT AGTATGTATA TAATGTATAA AGGTATGAAT ATCACAAACA GCAAATCGGC
 481 TATTCCCAAG TTGAGAAACG GTATAATAGA TATATTTCTA GATACCATTA ATAACCTTAT
 541 AAGCTTGACG TTTCCTATAA TGCCTACTAA GAAAACTAGA AGATACATAC ATACTAACGC
 601 CATACGAGAG TAACTACTCA TCGTATAACT ACTGTTGCTA ACAGTGACAC TGATGTTATA
 661 ACTCATCTTT GATGTGGTAT AAATGTATAA TAACTATATT ACACTGGTAT TTTATTTCAG
 721 TTATATACTA TATAGTATTA AAAATTATAT TTGTATAATT ATATTATTAT ATTCAGTGTA
 781 GAAAGTAAAA TACTATAAAT ATGTATCTCT TATTTATAAC TTATTAGTAA AGTATGTACT
 841 ATTCAGTTAT ATTGTTTTAT AAAAGCTAAA TGCTACTAGA TTGATATAAA TGAATATGTA
 901 ATAAATTAGT AATGTAGTAT ACTAATATTA ACTCACATTT GACTAATTAG CTATAAAAAC
 961 CCGGGCTGCA GCCCGGGAAG CTTACAAAAA TTAGACAAGA TTTGTTTCAG TATCATCACC
1021 GCTATCAAGA TTATTGAGGC GTTGGTATTT AGGTCCACGG CGACGGAGGG CCATGTTAGT
1081 GAGATGACTC GTTAGGATCG CTGGGCCCTT ATTCTTTTTC ATCGCCTTAT GTTCTTGTTG
1141 CTCCATAGCC GATACGAGGG ACATATATTT TATCATCTCC CTTGCCTGCA TTAGCTTTTC
1201 CTCATCGAAG TCATCGACTC CCGGGTCGCT ATCCCCACCA GCCGTTGAGC GGGCTCTTAG
1261 CGTCTGTTTC AAATTCCTAG TCGTCACAGG ATATAAGGCT TTCATTGGAT TTGCACGTAA
1321 TCTAGATATA TAGCGATATG CCAGGAATGC TGCGACGATG CCAGCTAATA TTAACAGTCC
1381 CACGGCCAAT GCTCCAAATG GGTTGTTTAG AAATGATGAT ACGCCTGATA CTGTTGAGAT
1441 TACCGCACTC GCAGCCCCTA AGACCACCTT GCCGAAACCA GCCCCCACAT CCCCGAGTCC
1501 CTGAAAGAAA TTTGCCATAC CACGCATGAT GACAAGATTA TTATCCACTC TGACTATGCT
1561 GTCTATATCA TAAAATTTTA AGGCGTGGAG TTGGTTGCGG CGTTGAATCT CGCTGTAGTC
1621 CAAAAGGCCG GTATCTTCCA GCTCAGCTCG TGTATAAACT TCGAGTGGGA GAAATTCACG
1681 ATCCTCTAGG AGAGTAAGAT TTAAATTCAC ATACGCACTT ATCAGTTCTA TCTCCGATAG
1741 CGGGACTTTA CGGACATACG CATAATCCTC AAAATATACA TAATCTGCCC CAAACTTAAA
1801 ATACCGCTTA TTATTGACAG TGCAAGGCTC AATTAGTTTT CGTTCCACGA GAAGTTCATT
1861 GTTTTCCCCT AGTTGTCCTT CTATGTATTC GGAGTCATTG AGGGCACGGA AGGAAACAAG
1921 AGGGCGGCTG TAACATGTCG TTGATGAACC CGTCACCCGC ATAGAATTTT GGATATAGAC
1981 ATGTCCGCTA GAAATGTTAA CACATTGTGT TACGGCGACG GCATCTCCAA GTAGGCGCGC
2041 GGATACACGA CGTTCTAGGG CCATCGAGAC CACCCCACCG GGATTGAGTT TTAGGGTCTC
2101 TGTCCACAGC ACATGTTCGC GGTTCTGAAG TGTACACCAG GCAGTGGCTA TCCGACTCAA
2161 CATTTCATTT ACATGGGCTT GTATGTAGTC ATAGGCAAAT TGTAGCATTG CGAATTCCAC
2221 AGATGAGGTG GTCTTGAGGA GTGATGCATT GTTCACGGTT TCTATACCCC CCTCTATTGT
```

FIG. 3B

| | | | | | | |
|---|---|---|---|---|---|---|
| 2281 | GCTGCGCCGC | GACCTATGAT | GTTGATTAGA | TGGGACCGAT | CTTCTAGTTC | GTTGTACTGT |
| 2341 | TTCCCCAGAT | GGATTGAGGA | GTGCACTGAG | ATCTACCGTG | CGATTGGAAC | GTGCTAATTC |
| 2401 | ATTGATATAT | AACTTTGCTA | GTTCGTTGCT | GATCATGGGA | CGGAAAGCTA | TTAGAAATCC |
| 2461 | CCCACGGGCT | AGGTAGGTCT | CCAGGGTTCC | AGTCTGAATA | TGAGTTTTAC | TATATTTACT |
| 2521 | CTTATAAATC | CGGTCTATGG | CTTCGGCTGC | CTCCTTGGTG | GCACAGTCCC | CCAAACGGAT |
| 2581 | ACGATTGATT | TCAAATTGTG | AAGTATTGGA | GATGAAAGTA | GCGGATATGG | TCTTGGCTGT |
| 2641 | AAATCTATAG | GAGCCCTGAT | ATTCATCGCG | TAGCATTTCA | TCTATTTCCC | TCCATTTGGC |
| 2701 | TAAGGTACAT | ACCCGACCAG | ACTTTGGGGT | CCAGTTCCAG | GCCACTGTCA | CATGCGGAGT |
| 2761 | TTCCAAAAAA | TTGCGAGAAA | CTGGTGCCCC | CAGTTGTAAT | CGCGTATCCA | AGTCTATTGG |
| 2821 | ATAGTATCCC | TCGATTTGTT | GAAATCTGTC | TGAAGAATAA | CTAGTATGTT | CTACATGGGC |
| 2881 | TCCATCCCTC | AGCCCAAAGA | ATGGAGACAT | GTGAATCACG | TCACCAGTGG | AGATAGCAAA |
| 2941 | TGAGTCATAT | GGATATACAG | ATCTTGCATC | CACTTCCTCT | ACGATGCAAT | TTACAGAGGT |
| 3001 | CCCAGAGTGG | TGAAATCCAG | CAGCACCGAT | CTTTGTGTAT | GTTTCATTGG | TGGTGTGCCA |
| 3061 | TCCACGGGAC | TCTGGAGTGT | TGAACTTGGA | GGGTTTCAGA | GGCAGTTCTC | TGGGATCCTC |
| 3121 | GTCTCGATCA | AAGGCCGTAA | ATTGATAATT | GTTACGAACG | TAATCAGCTT | TCGAGAGGCA |
| 3181 | CATACCCCGT | CTATCTATGA | GATCTGTAAT | CTCTTGAACT | TTCACGGGAA | CCCTGTCTGT |
| 3241 | ATATCGGTTG | GTTGTAACGG | CATAGGAACT | CCCAGACCAT | ACCGTTGTCA | TAATAATGTT |
| 3301 | TTTATAGTAT | ATATTTGCCT | TGAATTTATA | TGGCGCTATA | TTTTCTTTAA | ATATTACAGC |
| 3361 | TATACCCTCG | GTAAAATTTT | TCCCTAGTTT | ATAATCTGGA | CAGGCCCGTG | GTGGCTCTAA |
| 3421 | ACGCACGACA | GTAGATCCTG | AAGGTGGTGG | ACACATATAG | AAAGTCGATG | GTCCGTTAGC |
| 3481 | CTCTATTTGG | GACGCACGGA | GAGCTTCCCT | CATATCCGAC | ATATCGGTGG | GATCTGTAGT |
| 3541 | TGGTTTTGGT | GGTGTACCCC | CTACCTCAGG | GGTAGCTACA | GTCCGCCGGG | GTTGTTCCGA |
| 3601 | TGTGCTTCCA | GATTGACCCT | CTACTGGACG | GGGACCGACT | AAGAATAGTA | CGATCCAGAT |
| 3661 | AAATGAAACA | TATCTAGCTA | GTCTGGTTAA | TCCCGACGAT | CCGTTACCAT | GTCTGGAGCC |
| 3721 | AGTCGCTGCA | ATACCGAGTA | GAGAAGGGAA | AAAACATCTC | TGTCGAAAAT | AGCCACTGTG |
| 3781 | TCCCTGCCAA | CGACTCCCTC | GTCGCCGCTT | CCCAAGATCG | CCACGAGTGG | ACATTACGAT |
| 3841 | ACAAACTTAA | CGGATATCGC | GATAATGAAA | TAATTTATGA | TTATTTCTCG | CTTTCAATTT |
| 3901 | AACACAACCC | TCAAGAACCT | TTGTATTTAT | TTTCACTTTT | TAAGTATAGA | ATAAAGAAGC |
| 3961 | TCTAATTAAT | TAAGCTACAA | ATAGTTTCGT | TTTCACCTTG | TCTAATAACT | AATTAATTAA |
| 4021 | CCCGGATCGA | TCCCGATTTT | TATGACTAGT | TAATCAAATA | AAAAGCATAC | AAGCTATTGC |
| 4081 | TTCGCTATCG | TTACAAAATG | GCAGGAATTT | TGTGTAAACT | AAGCCACATA | CTTGCCAATG |
| 4141 | AAAAAAATAG | TAGAAAGGAT | ACTATTTTAA | TGGGATTAGA | TGTTAAGGTT | CCTTGGGATT |
| 4201 | ATAGTAACTG | GGCATCTGTT | AACTTTTACG | ACGTTAGGTT | AGATACTGAT | GTTACAGATT |
| 4261 | ATAATAATGT | TACAATAAAA | TACATGACAG | GATGTGATAT | TTTTCCTCAT | ATAACTCTTG |
| 4321 | GAATAGCAAA | TATGGATCAA | TGTGATAGAT | TTGAAAATTT | CAAAAAGCAA | ATAACTGATC |
| 4381 | AAGATTTACA | GACTATTTCT | ATAGTCTGTA | AAGAAGAGAT | GTGTTTTCCT | CAGAGTAACG |
| 4441 | CCTCTAAACA | GTTGGGAGCG | AAAGGATGCG | CTGTAGTTAT | GAAACTGGAG | GTATCTGATG |
| 4501 | AACTTAGAGC | CCTAAGAAAT | GTTCTGCTGA | ATGCGGTACC | CTGTTCGAAG | GACGTGTTTG |
| 4561 | GTGATATCAC | AGTAGATAAT | CCGTGGAATC | CTCACATAAC | AGTAGGATAT | GTTAAGGAGG |
| 4621 | ACGATGTCGA | AAACAAGAAA | CGCCTAATGG | AGTGCATGTC | CAAGTTTAGG | GGGCAAGAAA |
| 4681 | TACAAGTTCT | AGGATGGTAT | TAATAAGTAT | CTAAGTATTT | GGTATAATTT | ATTAAATAGT |
| 4741 | ATAATTATAA | CAAATAATAA | ATAACATGAT | AACGGTTTTT | ATTAGAATAA | AATAGAGATA |
| 4801 | ATATCATAAT | GATATATAAT | ACTTCATTAC | CAGAAATGAG | TAATGGAAGA | CTTATAAATG |
| 4861 | AACTGCATAA | AGCTATAAGG | TATAGAGATA | TAAATTTAGT | AAGGTATATA | CTTAAAAAAT |
| 4921 | GCAAATACAA | TAACGTAAAT | ATACTATCAA | CGTCTTTGTA | TTTAGCCGTA | AGTATTTCTG |
| 4981 | ATATAGAAAT | GGTAAAATTA | TTACTAGAAC | ACGGTGCCGA | TATTTTAAAA | TGTAAAAATC |
| 5041 | CTCCTCTTCA | TAAAGCTGCT | AGTTTAGATA | ATACAGAAAT | TGCTAAACTA | CTAATAGATT |
| 5101 | CTGGCGCTGA | CATAGAACAG | ATACATTCTG | GAAATAGTCC | GTTATATATT | TCTGTATATA |
| 5161 | GAAACAATAA | GTCATTAACT | AGATATTTAT | TAAAAAAAGG | TGTTAATTGT | AATAGATTCT |
| 5221 | TTCTAAATTA | TTACGATGTA | CTGTATGATA | AGATATCTGA | TGATATGTAT | AAAATATTTA |
| 5281 | TAGATTTTAA | TATTGATCTT | AATATACAAA | CTAGAAATTT | TGAAACTCCG | TTACATTACG |
| 5341 | CTATAAAGTA | TAAGAATATA | GATTTAATTA | GGATATTGTT | AGATAATAGT | ATTAAAATAG |
| 5401 | ATAAAAGTTT | ATTTTTGCAT | AAACAGTATC | TCATAAAGGC | ACTTAAAAAT | AATTGTAGTT |
| 5461 | ACGATATAAT | AGCGTTACTT | ATAAATCACG | GAGTGCCTAT | AAACGAACAA | GATGATTTAG |

FIG. 3C

```
5521 GTAAAACCCC ATTACATCAT TCGGTAATTA ATAGAAGAAA AGATGTAACA GCACTTCTGT
5581 TAAATCTAGG AGCTGATATA AACGTAATAG ATGACTGTAT GGGCAGTCCC TTACATTACG
5641 CTGTTTCACG TAACGATATC GAAACAACAA AGACACTTTT AGAAAGAGGA TCTAATGTTA
5701 ATGTGGTTAA TAATCATATA GATACCGTTC TAAATATAGC TGTTGCATCT AAAAACAAAA
5761 CTATAGTAAA CTTATTACTG AAGTACGGTA CTGATACAAA GTTGGTAGGA TTAGATAAAC
5821 ATGTTATTCA CATAGCTATA GAAATGAAAG ATATTAATAT ACTGAATGCG ATCTTATTAT
5881 ATGGTTGCTA TGTAAACGTC TATAATCATA AAGGTTTCAC TCCTCTATAC ATGGCAGTTA
5941 GTTCTATGAA AACAGAATTT GTTAAACTCT TACTTGACCA CGGTGCTTAC GTAAATGCTA
6001 AAGCTAAGTT ATCTGGAAAT ACTCCTTTAC ATAAAGCTAT GTTATCTAAT AGTTTTAATA
6061 ATATAAAATT ACTTTTATCT TATAACGCCG ACTATAATTC TCTAAATAAT CACGGTAATA
6121 CGCCTCTAAC TTGTGTTAGC TTTTTAGATG ACAAGATAGC TATTATGATA ATATCTAAAA
6181 TGATGTTAGA AATATCTAAA AATCCTGAAA TAGCTAATTC AGAAGGTTTT ATAGTAAACA
6241 TGGAACATAT AAACAGTAAT AAAAGACTAC TATCTATAAA AGAATCATGC GAAAAAGAAC
6301 TAGATGTTAT AACACATATA AAGTTAAATT CTATATATTC TTTTAATATC TTTCTTGACA
6361 ATAACATAGA TCTTATGGTA AAGTTCGTAA CTAATCCTAG AGTTAATAAG ATACCTGCAT
6421 GTATACGTAT ATATAGGGAA TTAATACGGA AAAATAAATC ATTAGCTTTT CATAGACATC
6481 AGCTAATAGT TAAAGCTGTA AAAGAGAGTA AGAATCTAGG AATAATAGGT AGGTTACCTA
6541 TAGATATCAA ACATATAATA ATGGAACTAT TAAGTAATAA TGATTTACAT TCTGTTATCA
6601 CCAGCTGTTG TAACCCAGTA GTATAAAG
```

FIG. 4A

POL/NEF epitopes

```
         10         20         30         40         50         60         70         80         90        100        110
    *    *     *    *     *    *     *    *     *    *     *    *     *    *     *    *     *    *     *    *     *    *
TTTTTTTCAT TATTTAGAAA TTATGCATTT TAGATCTTTA TAAGCGGCCG TGATTAACTA GTCATAAAAA CCCGGGATCG ATTCTAGACT CGAGGGTACC GGATCTTAAT
AAAAAAAGTA ATAAATCTTT AATACGTAAA ATCTAGAAAT ATTCGCCGGC ACTAATTGAT CAGTATTTTT GGGCCCTAGC TAAGATCTGA GCTCCCATGG CCTAGAATTA

        120        130        140        150        160        170        180        190        200        210        220
    *    *     *    *     *    *     *    *     *    *     *    *     *    *     *    *     *    *     *    *     *    *
TAATTAGTCA TCAGGCAGGG CGAGAACGAG ACTATCTGCT CGTTAATTAA TTAGGTCGAC GGATCCCCCA ACAAAAACTA ATCAGCTATC GGGGTTAATT AATTAGTTAT
ATTAATCAGT AGTCCGTCCC GCTCTTGCTC TGATAGACGA GCAATTAATT AATCCAGCTG CCTAGGGGGT TGTTTTTGAT TAGTCGATAG CCCCAATTAA TTAATCAATA

        230        240        250        260        270        280        290        300        310        320        330
    *    *     *    *     *    *     *    *     *    *     *    *     *    *     *    *     *    *     *    *     *    *
TAGACAAGGT GAAAACGAAA CTATTTGTAG CTTAATTAAT TAGAGCTTCT TTATTCTATA CTTAAAAAGT GAAAATAAAT ACAAAGGTTC TTGAGGGTTG TGTTAAATTG
ATCTGTTCCA CTTTTGCTTT GATAAACATC GAATTAATTA ATCTCGAAGA AATAAGATAT GAATTTTTCA CTTTTATTTA TGTTTCCAAG AACTCCCAAC ACAATTTAAC
                                                   ______________________H6 promoter_____________________>

        340        350        360        370        380        390        400        410        420        430
    *    *     *    *     *    *     *    *     *    *     *    *     *    *     *    *     *    *     *    *
AAAGCGAGAA ATAATCATAA ATTATTTCAT TATCGCGATA TCCGTTAAGT TTGTATCGTA ATG CCA CTA ACA GAA GAA GCA GAG CTA GAA CTG GCA GAA AAC
TTTCGCTCTT TATTAGTATT TAATAAAGTA ATAGCGCTAT AGGCAATTCA AACATAGCAT TAC GGT GAT TGT CTT CTT CGT CTC GAT CTT GAC CGT CTT TTG
______________________H6 promoter____________________> Met Pro Leu Thr Glu Glu Ala Glu Leu Glu Leu Ala Glu Asn
                                                       _______________POL/NEF Epitopes_______________>
```

FIG. 4B

```
        440         450         460         470         480         490         500         510         520
   *     *     *     *     *     *     *     *     *     *     *     *     *     *     *     *     *     *
AGA GAG ATT CTA AAA GAA CCA GTA CAT GGA GTG TAT TAT GAC CCA TCA AAA GAC TTA ATA GCA GAA ATA CAG AAG CAG GGG CAA GGC CAA
TCT CTC TAA GAT TTT CTT GGT CAT GTA CCT CAC ATA ATA CTG GGT AGT TTT CTG AAT TAT CGT CTT TAT GTC TTC GTC CCC GTT CCG GTT
Arg Glu Ile Leu Lys Glu Pro Val His Gly Val Tyr Tyr Asp Pro Ser Lys Asp Leu Ile Ala Glu Ile Gln Lys Gln Gly Gln Gly Gln
_____________________________________________POL/NEF Epitopes_____________________________________________>

        530         540         550         560         570         580         590         600         610
   *     *     *     *     *     *     *     *     *     *     *     *     *     *     *     *     *     *
TGG ACA TAT CAA ATT TAT CAA GAG CCA TTT AAA AAT CTG AAA ACA GGA ATG GAG TGG AGA TTT GAT TCT AGA TTA GCA TTT CAT CAC GTA
ACC TGT ATA GTT TAA ATA GTT CTC GGT AAA TTT TTA GAC TTT TGT CCT TAC CTC ACC TCT AAA CTA AGA TCT AAT CGT AAA GTA GTG CAT
Trp Thr Tyr Gln Ile Tyr Gln Glu Pro Phe Lys Asn Leu Lys Thr Gly Met Glu Trp Arg Phe Asp Ser Arg Leu Ala Phe His His Val
_____________________________________________POL/NEF Epitopes_____________________________________________>

        620         630         640         650         660         670         680         690         700
   *     *     *     *     *     *     *     *     *     *     *     *     *     *     *     *     *     *
GCT AGA GAA TTA CAT CCT GAA TAT TTT AAA AAT TGT AAG CTT ATG GCA ATA TTC CAA AGT AGC ATG ACA AAA ATC TTA GAG CCT TTT AGA
CGA TCT CTT AAT GTA GGA CTT ATA AAA TTT TTA ACA TTC GAA TAC CGT TAT AAG GTT TCA TCG TAC TGT TTT TAG AAT CTC GGA AAA TCT
Ala Arg Glu Leu His Pro Glu Tyr Phe Lys Asn Cys Lys Leu Met Ala Ile Phe Gln Ser Ser Met Thr Lys Ile Leu Glu Pro Phe Arg
_____________________________________________POL/NEF Epitopes_____________________________________________>

        710         720         730         740         750         760         770         780         790
   *     *     *     *     *     *     *     *     *     *     *     *     *     *     *     *     *     *
AAA CAA AAT CCA GAC ATA GTT ATC TAT CAA TAC ATG GAT GAT TTG TAT GTA GGA TCT GAC TTA GAA ATA GGG CAG CAT AGA ACA AAA ATA
TTT GTT TTA GGT CTG TAT CAA TAG ATA GTT ATG TAC CTA CTA AAC ATA CAT CCT AGA CTG AAT CTT TAT CCC GTC GTA TCT TGT TTT TAT
Lys Gln Asn Pro Asp Ile Val Ile Tyr Gln Tyr Met Asp Asp Leu Tyr Val Gly Ser Asp Leu Glu Ile Gly Gln His Arg Thr Lys Ile
_____________________________________________POL/NEF Epitopes_____________________________________________>

        800         810         820         830         840         850         860         870         880
   *     *     *     *     *     *     *     *     *     *     *     *     *     *     *     *     *     *
GAG GAG CTG AGA CAA CAT CTG TTG AGG TGG GGA CTT ACA ACC ATG GTA GGT TTT CCA GTA ACA CCT CAA GTA CCT TTA AGA CCA ATG ACT
CTC CTC GAC TCT GTT GTA GAC AAC TCC ACC CCT GAA TGT TGG TAC CAT CCA AAA GGT CAT TGT GGA GTT CAT GGA AAT TCT GGT TAC TGA
Glu Glu Leu Arg Gln His Leu Leu Arg Trp Gly Leu Thr Thr Met Val Gly Phe Pro Val Thr Pro Gln Val Pro Leu Arg Pro Met Thr
_____________________________________________POL/NEF Epitopes_____________________________________________>
```

FIG. 4C

```
     890       900        910       920       930       940       950       960       970
 *    *    *    *    *    *    *    *    *    *    *    *    *    *    *    *    *    *
TAC AAA GCA GCT GTA GAT CTT TCT CAC TTT TTA AAA GAA AAA GGA GGT TTA GAA GGG CTA ATT CAT TCT CAA CGA AGA CAA GAT ATT CTT
ATG TTT CGT CGA CAT CTA GAA AGA GTG AAA AAT TTT CTT TTT CCT CCA AAT CTT CCC GAT TAA GTA AGA GTT GCT TCT GTT CTA TAA GAA
Tyr Lys Ala Ala Val Asp Leu Ser His Phe Leu Lys Glu Lys Gly Gly Leu Glu Gly Leu Ile His Ser Gln Arg Arg Gln Asp Ile Leu
___________________________________________POL/NEF Epitopes___________________________________________>

     980       990       1000      1010      1020      1030      1040      1050      1060
 *    *    *    *    *    *    *    *    *    *    *    *    *    *    *    *    *    *
GAT TTG TGG ATT TAT CAT ACA CAA GGA TAT TTT CCT GAT TGG CAG AAT TAC ACA CCA GGA CCA GGA GTC AGA TAC CCA TTA ACC TTT GGT
CTA AAC ACC TAA ATA GTA TGT GTT CCT ATA AAA GGA CTA ACC GTC TTA ATG TGT GGT CCT GGT CCT CAG TCT ATG GGT AAT TGG AAA CCA
Asp Leu Trp Ile Tyr His Thr Gln Gly Tyr Phe Pro Asp Trp Gln Asn Tyr Thr Pro Gly Pro Gly Val Arg Tyr Pro Leu Thr Phe Gly
___________________________________________POL/NEF Epitopes___________________________________________>

     1070      1080      1090      1100      1110      1120      1130      1140      1150
 *    *    *    *    *    *    *    *    *    *    *    *    *    *    *    *    *    *
TGG TGC TAC AAG CTA GTA CCA ATG ATT GAG ACT GTA CCA GTA AAA TTA AAG CCA GGA ATG GAT GGC CCA AAA GTT AAA CAA TGG CCA TTG
ACC ACG ATG TTC GAT CAT GGT TAC TAA CTC TGA CAT GGT CAT TTT AAT TTC GGT CCT TAC CTA CCG GGT TTT CAA TTT GTT ACC GGT AAC
Trp Cys Tyr Lys Leu Val Pro Met Ile Glu Thr Val Pro Val Lys Leu Lys Pro Gly Met Asp Gly Pro Lys Val Lys Gln Trp Pro Leu
___________________________________________POL/NEF Epitopes___________________________________________>

     1160      1170      1180      1190      1200      1210      1220      1230      1240
 *    *    *    *    *    *    *    *    *    *    *    *    *    *    *    *    *    *
ACA GAA GAA AAA ATA AAA GCA TTA GTA GAA ATT TGT ACA GAG ATG GAA AAG GAA GGG AAA ATT TCA AAA ATT GGG CCT TAA TTTTTCT
TGT CTT CTT TTT TAT TTT CGT AAT CAT CTT TAA ACA TGT CTC TAC CTT TTC CTT CCC TTT TAA AGT TTT TAA CCC GGA ATT AAAAAGA
Thr Glu Glu Lys Ile Lys Ala Leu Val Glu Ile Cys Thr Glu Met Glu Lys Glu Gly Lys Ile Ser Lys Ile Gly Pro
_________________________________POL/NEF Epitopes_________________________________>

     1250       1260       1270       1280       1290       1300       1310       1320       1330       1340       1350
 *    *    *    *    *    *    *    *    *    *    *    *    *    *    *    *    *    *    *    *    *    *
GCAGCCCGGG GGATCCTTTT TATAGCTAAT TAGTCACGTA CCTTTGAGAG TACCACTTCA GCTACCTCTT TTGTGTCTCA GAGTAACTTT CTTTAATCAA TTCCAAAACA
CGTCGGGCCC CCTAGGAAAA ATATCGATTA ATCAGTGCAT GGAAACTCTC ATGGTGAAGT CGATGGAGAA AACACAGAGT CTCATTGAAA GAAATTAGTT AAGGTTTTGT
```

gag (+ pro) and gp120 (+ transmembrane)

FIG. 5A

| FEATURES | From | To/Span | Description |
|---|---|---|---|
| frag | 1 | 56 | C3 flanking arm |
| frag | 162 | 76 (C) | HIV1 (IIIB) env transmembrane region |
| frag | 1728 | 163 (C) | HIV1 (MN) gp120 gene |
| frag | 1853 | 1729 (C) | vaccinia H6 promoter |
| frag | 1925 | 1983 | vaccinia I3L promoter |
| frag | 1984 | 3746 | HIV1 (IIIB) gag/pro gene |
| frag | 3753 | 3808 | C3 flanking arm |

```
        10        20        30        40        50        60        70        80        90       100       110       120
TAATGTAGTATACTAATATTAACTCACATTTGACTAATTAGCTATAAAAACCCGGGATCGATTCTAGAATAAAAATTATCCCTGCCTAACTCTATTCACTACAGAGAGTACAGCAAAAAC
ATTACATCATATGATTATAATTGAGTGTAAACTGATTAATCGATATTTTTGGGCCCTAGCTAAGATCTTATTTTTAATAGGGACGGATTGAGATAAGTGATGTCTCTCATGTCGTTTTTG
____________________C3 FLANKING ARM____________________>                          G  Q  R  V  R  N  V  V  S  L  V  A  F  V
                                                                                <____HIV1 (IIIB) ENV TRANSMEMBRANE REGION_____

       130       140       150       160       170       180       190       200       210       220       230       240
TATTCTTAAACCTACCAAGCCTCCTACTATCATTATGAATAATCTTTTTTCTCTCTGCACCACTCTTCTCTTTGCCTTGGTGGGTGCTACTCCTAATGGTTCAATTGTTACTACTTTATA
ATAAGAATTTGGATGGTTCGGAGGATGATAGTAATACTTATTAGAAAAAAGAGAGACGTGGTGAGAAGAGAAACGGAACCACCCACGATGAGGATTACCAAGTTAACAATGATGAAATAT
 I  R  L  G  V  L  G  G  V  I  M  I  F  L  R  K  E  R  Q  V  V  R  R  K  A  K  T  P  A  V  G  L  P  E  I  T  V  V  K  Y
<__HIV1 (IIIB) ENV TRANSMEMBRANE REGION___
                                         <___________________________HIV1 (MN) GP120 GENE_______________________________

       250       260       270       280       290       300       310       320       330       340       350       360
TTTATATAATTCACTTCTCCAATTGTCCCTCATATCTCCTCCTCCAGGTCTGAAGATCTCGGTGTCGTTCGTGTCCGTGTCCTTACCACCATCTCTTGTTAATAGTAGCCCTGTAATATT
AAATATATTAAGTGAAGAGGTTAACAGGGAGTATAGAGGAGGAGGTCCAGACTTCTAGAGCCACAGCAAGCACAGGCACAGGAATGGTGGTAGAGAACAATTATCATCGGGACATTATAA
 K  Y  L  E  S  R  W  N  D  R  M  D  G  G  G  P  R  F  I  E  T  D  N  T  D  T  D  K  G  G  D  R  T  L  L  L  G  T  I  N
<________________________________________________HIV1 (MN) GP120 GENE____________________________________________________
```

FIG. 5B 370 380 390 400 410 420 430 440 450 460 470 480
TGATGAACATCTAATTTGTCCTTCAATGGGAGGGGCATATATTGCTTTTCCTACTTCCTGCCACATGTTTATAATTTGTTTTATTTTGCATTGAAGTGTGATATTGTTATTTGACCCTGT
ACTACTTGTAGATTAAACAGGAAGTTACCCTCCCCGTATATAACGAAAAGGATGAAGGACGGTGTACAAATATTAAACAAAATAAAACGTAACTTCACACTATAACAATAAACTGGGACA
S S C R I Q G E I P P A Y I A K G V E Q W M N I I Q K I K C Q L T I N N N S G T
<____ HIV1 (MN) GP120 GENE ____

490 500 510 520 530 540 550 560 570 580 590 600
AGTATTATTCCAAGTATTATTACCATTCCAAGTACTATTAAACAGTGGTGATGAATTACAGTAGAAGAATTCCCCTCCACAATTAAAACTGTGCATTACAATTTCTGGGTCCCCTCCTGA
TCATAATAAGGTTCATAATAATGGTAAGGTTCATGATAATTTGTCACCACTACTTAATGTCATCTTCTTAAGGGGAGGTGTTAATTTTGACACGTAATGTTAAAGACCCAGGGGAGGACT
T N N W T N N G N W T S N F L P S S N C Y F F E G G C N F S H M V I E P D G G S
<____ HIV1 (MN) GP120 GENE ____

610 620 630 640 650 660 670 680 690 700 710 720
GGATTGATTAAAGACTATTGTTTTATTCTTAAATTGTTCTTTTAATTTGCTAACTATCTGTCTTAAAGTGTCATTCCATTTTGCTCTACTAATGTTACAATGTGCTTGTCTTATAGTTCC
CCTAACTAATTTCTGATAACAAAATAAGAATTTAACAAGAAAATTAAACGATTGATAGACAGAATTTCACAGTAAGGTAAAACGAGATGATTACAATGTTACACGAACAGAATATCAAGG
S Q N F V I T K N K F Q E K L K S V I Q R L T D N W K A R S I N C H A Q R I T G
<____ HIV1 (MN) GP120 GENE ____

730 740 750 760 770 780 790 800 810 820 830 840
TATTATATTTTTTGTTGTATAAAATGCTCTCCCTGGTCCTATATGTATCCTTTTTCTTTTATTGTAGTTGGGTCTTGTACAATTAATTTGTACAGATTCATTCAGATGTACTATGATGGT
ATAATATAAAAAACAACATATTTTACGAGAGGGACCAGGATATACATAGGAAAAAGAAAATAACATCAACCCAGAACATGTTAATTAAACATGTCTAAGTAAGTCTACATGATACTACCA
I I N K T T Y F A R G P G I H I R K R K N Y N P R T C N I Q V S E N L H V I I T
<____ HIV1 (MN) GP120 GENE ____

850 860 870 880 890 900 910 920 930 940 950 960
TTTAGCATTATCATTGAAATTCTCAGATCTAATTACTACCTCTTCTTCTGCTAGACTGCCATTTAACAGCAGTTGAGTTGATACTACTGGCCTAATTCCATGTGTACATTGTACTGTGCT
AAATCGTAATAGTAACTTTAAGAGTCTAGATTAATGATGGAGAAGAAGACGATCTGACGGTAAATTGTCGTCAACTCAACTATGATGACCGGATTAAGGTACACATGTAACATGACACGA
K A N D N F N E S R I V V E E E A L S G N L L L Q T S V V P R I G H T C Q V T S
<____ HIV1 (MN) GP120 GENE ____

FIG. 5C

```
       970       980       990      1000      1010      1020      1030      1040      1050      1060      1070      1080
GACATTTTTACATGATCCTTTTCCACTGAACTTTTTATCGTTACACTTTAGAATCGCAAAACCAGCCGGGGCACAATAGTGTATGGGAATTGGCTCAAAGGATATCTTTGGACAAGCTTG
CTGTAAAAATGTACTAGGAAAAGGTGACTTGAAAAATAGCAATGTGAAATCTTAGCGTTTTGGTCGGCCCCGTGTTATCACATACCCTTAACCGAGTTTCCTATAGAAACCTGTTCGAAC
 V  N  K  C  S  G  K  G  S  F  K  K  D  N  C  K  L  I  A  F  G  A  P  A  C  Y  H  I  P  I  P  E  F  S  I  K  P  C  A  Q
<_______________________________________________HIV1 (MN) GP120 GENE__________________________________________________

      1090      1100      1110      1120      1130      1140      1150      1160      1170      1180      1190      1200
TGTAATGACTGAGGTATTACAACTTATCAACCTATAGCTGGTACTATCATTATTTATTGATACTATATCAAGTTTATAAAGAAGTGCATATTCTTTCTGCATCTTATCTCTTATGCTTGT
ACATTACTGACTCCATAATGTTGAATAGTTGGATATCGACCATGATAGTAATAAATAACTATGATATAGTTCAAATATTTCTTCACGTATAAGAAAGACGTAGAATAGAGAATACGAACA
 T  I  V  S  T  N  C  S  I  L  R  Y  S  T  S  D  N  N  I  S  V  I  D  L  K  Y  L  L  A  Y  E  K  Q  M  K  D  R  I  S  T
<_______________________________________________HIV1 (MN) GP120 GENE__________________________________________________

      1210      1220      1230      1240      1250      1260      1270      1280      1290      1300      1310      1320
GGTGATATTGAAAGAGCAGTTTTTCATTTCTCCTCCCTTTATTGTTCCCTCGCTATTACTATTGTTATTAGCAGTACTATTATTGGTATTAGTAGTATTCCTCAAATCAGTGCAATTTAA
CCACTATAACTTTCTCGTCAAAAAGTAAAGAGGAGGGAAATAACAAGGGAGCGATAATGATAACAATAATCGTCATGATAATAACCATAATCATCATAAGGAGTTTAGTCACGTTAAATT
 T  I  N  F  S  C  N  K  M  E  G  G  K  I  T  G  E  S  N  S  N  N  N  A  T  S  N  N  T  N  T  T  N  R  L  D  T  C  N  L
<_______________________________________________HIV1 (MN) GP120 GENE__________________________________________________

      1330      1340      1350      1360      1370      1380      1390      1400      1410      1420      1430      1440
AGTAACACAGAGTGGGGTTAATTTTACACATGGCTTTAGGCTTTGATCCCATAAACTGATTATATCCTCATGCATCTGTTCTACCATGTTATTTTTCCACATGTTAAAATTTTCTGTCAC
TCATTGTGTCTCACCCCAATTAAAATGTGTACCGAAATCCGAAACTAGGGTATTTGACTAATATAGGAGTACGTAGACAAGATGGTACAATAAAAAGGTGTACAATTTTAAAAGACAGTG
 T  V  C  L  P  T  L  K  V  C  P  K  L  S  Q  D  W  L  S  I  I  D  E  H  M  Q  E  V  M  N  N  K  W  M  N  F  N  E  T  V
<_______________________________________________HIV1 (MN) GP120 GENE__________________________________________________

      1450      1460      1470      1480      1490      1500      1510      1520      1530      1540      1550      1560
ATTTACCAATTCTACTTCTTGTGGGTTGGGGTCTGTGGGTACACAGGCATGTGTGGCCCAAACATTATGTACCTCTGTATCATATGCTTTAGCATCTGATGCACAAAATAGAGTGGTGGT
TAAATGGTTAAGATGAAGAACACCCAACCCCAGACACCCATGTGTCCGTACACACCGGGTTTGTAATACATGGAGACATAGTATACGAAATCGTAGACTACGTGTTTTATCTCACCACCA
 N  V  L  E  V  E  Q  P  N  P  D  T  P  V  C  A  H  T  A  W  V  N  H  V  E  T  D  Y  A  K  A  D  S  A  C  F  L  T  T  T
<_______________________________________________HIV1 (MN) GP120 GENE__________________________________________________
```

FIG.5D

```
      1570      1580      1590      1600      1610      1620      1630      1640      1650      1660      1670      1680
TGCTTCTTTCCACACAGGTACCCCATAATAGACTGTGACCCACAATTTTTCTGTAGCACTACAGATCATCAACATCCCAAGGAGCATGGTGCCCCATCTCCACCCCCATCTCCACAAGTG
ACGAAGAAAGGTGTGTCCATGGGGTATTATCTGACACTGGGTGTTAAAAAGACATCGTGATGTCTAGTAGTTGTAGGGTTCCTCGTACCACGGGGTAGAGGTGGGGGTAGAGGTGTTCAC
 A  E  K  W  V  P  V  G  Y  Y  V  T  V  W  L  K  E  T  A  S  C  I  M  L  M  G  L  L  M  T  G  W  R  W  G  W  R  W  L  H
<________________________________HIV1 (MN) GP120 GENE______________________________________

      1690      1700      1710      1720      1730      1740      1750      1760      1770      1780      1790      1800
CTGATATTTCTCCTTCACTCTCATTGCCACTGTCTTCTGCTCTTTCATATACGATACAAACTTAACGCATATCGCGATAATGAAATAATTTATGATTATTTCTCGCTTTCAATTTAACAC
GACTATAAAGAGGAAGTGAGAGTAACGGTGACAGAAGACGAGAAAGTATATGCTATGTTTGAATTGCGTATAGCGCTATTACTTTATTAAATACTAATAAAGAGCGAAAGTTAAATTGTG
 Q  Y  K  E  K  V  R  M  A  V  T  K  Q  E  K  M
<________HIV1 (MN) GP120 GENE__________
                                         <________________VACCINIA H6 PROMOTER___________________

      1810      1820      1830      1840      1850      1860      1870      1880      1890      1900      1910      1920
AACCCTCAAGAACCTTTGTATTTATTTTCACTTTTTAAGTATAGAATAAAGAAGCTCTAATTAATTAAGCTACAAATAGTTTCGTTTTCACCTTGTCTAATAACTAATTAATTAACCCGG
TTGGGAGTTCTTGGAAACATAAATAAAAGTGAAAAATTCATATCTTATTTCTTCGAGATTAATTAATTCGATGTTTATCAAAGCAAAAGTGGAACAGATTATTGATTAATTAATTGGGCC
<__________VACCINIA H6 PROMOTER_____________

      1930      1940      1950      1960      1970      1980      1990      2000      2010      2020      2030      2040
ATCTTGAGATAAAGTGAAAATATATATCATTATATTACAAAGTACAATTATTTAGGTTTAATCATGGGTGCGAGAGCGTCAGTATTAAGCGGGGGAGAATTAGATCGATGGGAAAAAATT
TAGAACTCTATTTCACTTTTATATATAGTAATATAATGTTTCATGTTAATAAATCCAAATTAGTACCCACGCTCTCGCAGTCATAATTCGCCCCCTCTTAATCTAGCTACCCTTTTTTAA
   ____________VACCINIA I3L PROMOTER_______________> M  G  A  R  A  S  V  L  S  G  G  E  L  D  R  W  E  K  I
                                                    __________HIV1 (IIIB) GAG/PRO GENE___________>

      2050      2060      2070      2080      2090      2100      2110      2120      2130      2140      2150      2160
CGGTTAAGGCCAGGGGGAAAGAAAAAATATAAATTAAAACATATAGTATGGGCAAGCAGGGAGCTAGAACGATTCGCAGTTAATCCTGGCCTGTTAGAAACATCAGAAGGCTGTAGACAA
GCCAATTCCGGTCCCCCTTTCTTTTTTATATTTAATTTTGTATATCATACCCGTTCGTCCCTCGATCTTGCTAAGCGTCAATTAGGACCGGACAATCTTTGTAGTCTTCCGACATCTGTT
 R  L  R  P  G  G  K  K  K  Y  K  L  K  H  I  V  W  A  S  R  E  L  E  R  F  A  V  N  P  G  L  L  E  T  S  E  G  C  R  Q
________________________________HIV1 (IIIB) GAG/PRO GENE_______________________________>

      2170      2180      2190      2200      2210      2220      2230      2240      2250      2260      2270      2280
```

```
ATACTGGGACAGCTACAACCATCCCTTCAGACAGGATCAGAAGAACTTAGATCATTATATAATACAGTAGCAACCCTCTATTGTGTGCATCAAAGGATAGAGATAAAAGACACCAAGGAA
TATGACCCTGTCGATGTTGGTAGGGAAGTCTGTCCTAGTCTTCTTGAATCTAGTAATATATTATGTCATCGTTGGGAGATAACACACGTAGTTTCCTATCTCTATTTTCTGTGGTTCCTT
 I  L  G  Q  L  Q  P  S  L  Q  T  G  S  E  E  L  R  S  L  Y  N  T  V  A  T  L  Y  C  V  H  Q  R  I  E  I  K  D  T  K  E
________________________________________________HIV1 (IIIB) GAG/PRO GENE_______________________________________________>

       2290      2300      2310      2320      2330      2340      2350      2360      2370      2380      2390      2400
GCTTTAGACAAGATAGAGGAAGAGCAAAACAAAAGTAAGAAAAAAGCACAGCAAGCAGCAGCTGACACAGGACACAGCAATCAGGTCAGCCAAAATTACCCTATAGTGCAGAACATCCAG
CGAAATCTGTTCTATCTCCTTCTCGTTTTGTTTTCATTCTTTTTTCGTGTCGTTCGTCGTCGACTGTGTCCTGTGTCGTTAGTCCAGTCGGTTTTAATGGGATATCACGTCTTGTAGGTC
 A  L  D  K  I  E  E  E  Q  N  K  S  K  K  K  A  Q  Q  A  A  A  D  T  G  H  S  N  Q  V  S  Q  N  Y  P  I  V  Q  N  I  Q
________________________________________________HIV1 (IIIB) GAG/PRO GENE_______________________________________________>

       2410      2420      2430      2440      2450      2460      2470      2480      2490      2500      2510      2520
GGGCAAATGGTACATCAGGCCATATCACCTAGAACTTTAAATGCATGGGTAAAAGTAGTAGAAGAGAAGGCTTTCAGCCCAGAAGTGATACCCATGTTTTCAGCATTATCAGAAGGAGCC
CCCGTTTACCATGTAGTCCGGTATAGTGGATCTTGAAATTTACGTACCCATTTTCATCATCTTCTCTTCCGAAAGTCGGGTCTTCACTATGGGTACAAAAGTCGTAATAGTCTTCCTCGG
 G  Q  M  V  H  Q  A  I  S  P  R  T  L  N  A  W  V  K  V  V  E  E  K  A  F  S  P  E  V  I  P  M  F  S  A  L  S  E  G  A
________________________________________________HIV1 (IIIB) GAG/PRO GENE_______________________________________________>

       2530      2540      2550      2560      2570      2580      2590      2600      2610      2620      2630      2640
ACCCCACAAGATTTAAACACCATGCTAAACACAGTGGGGGGACATCAAGCAGCCATGCAAATGTTAAAAGAGACCATCAATGAGGAAGCTGCAGAATGGGATAGAGTGCATCCAGTGCAT
TGGGGTGTTCTAAATTTGTGGTACGATTTGTGTCACCCCCCTGTAGTTCGTCGGTACGTTTACAATTTTCTCTGGTAGTTACTCCTTCGACGTCTTACCCTATCTCACGTAGGTCACGTA
 T  P  Q  D  L  N  T  M  L  N  T  V  G  G  H  Q  A  A  M  Q  M  L  K  E  T  I  N  E  E  A  A  E  W  D  R  V  H  P  V  H
________________________________________________HIV1 (IIIB) GAG/PRO GENE_______________________________________________>

       2650      2660      2670      2680      2690      2700      2710      2720      2730      2740      2750      2760
GCAGGGCCTATTGCACCAGGCCAGATGAGAGAACCAAGGGGAAGTGACATAGCAGGAACTACTAGTACCCTTCAGGAACAAATAGGATGGATGACAAATAATCCACCTATCCCAGTAGGA
CGTCCCGGATAACGTGGTCCGGTCTACTCTCTTGGTTCCCCTTCACTGTATCGTCCTTGATGATCATGGGAAGTCCTTGTTTATCCTACCTACTGTTTATTAGGTGGATAGGGTCATCCT
 A  G  P  I  A  P  G  Q  M  R  E  P  R  G  S  D  I  A  G  T  T  S  T  L  Q  E  Q  I  G  W  M  T  N  N  P  P  I  P  V  G
________________________________________________HIV1 (IIIB) GAG/PRO GENE_______________________________________________>
```

FIG. 5F

```
       2770      2780      2790      2800      2810      2820      2830      2840      2850      2860      2870      2880
GAAATTTATAAAAGATGGATAATCCTGGGATTAAATAAAATAGTAAGAATGTATAGCCCTACCAGCATTCTGGACATAAGACAAGGACCAAAAGAACCCTTTAGAGACTATGTAGACCGG
CTTTAAATATTTTCTACCTATTAGGACCCTAATTTATTTTATCATTCTTACATATCGGGATGGTCGTAAGACCTGTATTCTGTTCCTGGTTTTCTTGGGAAATCTCTGATACATCTGGCC
 E  I  Y  K  R  W  I  I  L  G  L  N  K  I  V  R  M  Y  S  P  T  S  I  L  D  I  R  Q  G  P  K  E  P  F  R  D  Y  V  D  R
_______________________________________________HIV1 (IIIB) GAG/PRO GENE______________________________________________>

       2890      2900      2910      2920      2930      2940      2950      2960      2970      2980      2990      3000
TTCTATAAAACTCTAAGAGCCGAGCAAGCTTCACAGGAGGTAAAAAATTGGATGACAGAAACCTTGTTGGTCCAAAATGCGAACCCAGATTGTAAGACTATTTTAAAAGCATTGGGACCA
AAGATATTTTGAGATTCTCGGCTCGTTCGAAGTGTCCTCCATTTTTTAACCTACTGTCTTTGGAACAACCAGGTTTTACGCTTGGGTCTAACATTCTGATAAAATTTTCGTAACCCTGGT
 F  Y  K  T  L  R  A  E  Q  A  S  Q  E  V  K  N  W  M  T  E  T  L  L  V  Q  N  A  N  P  D  C  K  T  I  L  K  A  L  G  P
_______________________________________________HIV1 (IIIB) GAG/PRO GENE______________________________________________>

       3010      3020      3030      3040      3050      3060      3070      3080      3090      3100      3110      3120
GCGGCTACACTAGAAGAAATGATGACAGCATGTCAGGGAGTAGGAGGACCCGGCCATAAGGCAAGAGTTTTGGCTGAAGCAATGAGCCAAGTAACAAATTCAGCTACCATAATGATGCAG
CGCCGATGTGATCTTCTTTACTACTGTCGTACAGTCCCTCATCCTCCTGGGCCGGTATTCCGTTCTCAAAACCGACTTCGTTACTCGGTTCATTGTTTAAGTCGATGGTATTACTACGTC
 A  A  T  L  E  E  M  M  T  A  C  Q  G  V  G  G  P  G  H  K  A  R  V  L  A  E  A  M  S  Q  V  T  N  S  A  T  I  M  M  Q
_______________________________________________HIV1 (IIIB) GAG/PRO GENE______________________________________________>

       3130      3140      3150      3160      3170      3180      3190      3200      3210      3220      3230      3240
AGAGGCAATTTTAGGAACCAAAGAAAGATTGTTAAGTGTTTCAATTGTGGCAAAGAAGGGCACACAGCCAGAAATTGCAGGGCCCCTAGGAAAAAGGGCTGTTGGAAATGTGGAAAGGAA
TCTCCGTTAAAATCCTTGGTTTCTTTCTAACAATTCACAAAGTTAACACCGTTTCTTCCCGTGTGTCGGTCTTTAACGTCCCGGGGATCCTTTTTCCCGACAACCTTTACACCTTTCCTT
 R  G  N  F  R  N  Q  R  K  I  V  K  C  F  N  C  G  K  E  G  H  T  A  R  N  C  R  A  P  R  K  K  G  C  W  K  C  G  K  E
_______________________________________________HIV1 (IIIB) GAG/PRO GENE______________________________________________>

       3250      3260      3270      3280      3290      3300      3310      3320      3330      3340      3350      3360
GGACACCAAATGAAAGATTGTACTGAGAGACAGGCTAATTTTTTAGGGAAGATCTGGCCTTCCTACAAGGGAAGGCCAGGGAATTTTCTTCAGAGCAGACCAGAGCCAACAGCCCCACCA
CCTGTGGTTTACTTTCTAACATGACTCTCTGTCCGATTAAAAAATCCCTTCTAGACCGGAAGGATGTTCCCTTCCGGTCCCTTAAAAGAAGTCTCGTCTGGTCTCGGTTGTCGGGGTGGT
 G  H  Q  M  K  D  C  T  E  R  Q  A  N  F  L  G  K  I  W  P  S  Y  K  G  R  P  G  N  F  L  Q  S  R  P  E  P  T  A  P  P
_______________________________________________HIV1 (IIIB) GAG/PRO GENE______________________________________________>
```

FIG. 5G

```
      3370      3380      3390      3400      3410      3420      3430      3440      3450      3460      3470      3480
GAAGAGAGCTTCAGGTCTGGGGTAGAGACAACAACTCCCCCTCAGAAGCAGGAGCCGATAGACAAGGAACTGTATCCTTTAACTTCCCTCAGATCACTCTTTGGCAACGACCCCTCGTCA
CTTCTCTCGAAGTCCAGACCCCATCTCTGTTGTTGAGGGGGAGTCTTCGTCCTCGGCTATCTGTTCCTTGACATAGGAAATTGAAGGGAGTCTAGTGAGAAACCGTTGCTGGGGAGCAGT
 E  E  S  F  R  S  G  V  E  T  T  T  P  P  Q  K  Q  E  P  I  D  K  E  L  Y  P  L  T  S  L  R  S  L  F  G  N  D  P  S  S
                                                                                            P  Q  I  T  L  W  Q  R  P  L  V
____________________________________________HIV1 (IIIB) GAG/PRO GENE_____________________________________________>

      3490      3500      3510      3520      3530      3540      3550      3560      3570      3580      3590      3600
CAATAAAGATAGGGGGGCAACTAAAGGAAGCTCTATTAGATACAGGAGCAGATGATACAGTATTAGAAGAAATGAGTTTGCCAGGAAGATGGAAACCAAAAATGATAGGGGGAATTGGAG
GTTATTTCTATCCCCCCGTTGATTTCCTTCGAGATAATCTATGTCCTCGTCTACTATGTCATAATCTTCTTTACTCAAACGGTCCTTCTACCTTTGGTTTTTACTATCCCCCTTAACCTC
 Q
T  I  K  I  G  G  Q  L  K  E  A  L  L  D  T  G  A  D  D  T  V  L  E  E  M  S  L  P  G  R  W  K  P  K  M  I  G  G  I  G
____________________________________________HIV1 (IIIB) GAG/PRO GENE_____________________________________________>

      3610      3620      3630      3640      3650      3660      3670      3680      3690      3700      3710      3720
GTTTTATCAAAGTAAGACAGTATGATCAGATACTCATAGAAATCTGTGGACATAAAGCTATAGGTACAGTATTAGTAGGACCTACACCTGTCAACATAATTGGAAGAAATCTGTTGACTC
CAAAATAGTTTCATTCTGTCATACTAGTCTATGAGTATCTTTAGACACCTGTATTTCGATATCCATGTCATAATCATCCTGGATGTGGACAGTTGTATTAACCTTCTTTAGACAACTGAG
G  F  I  K  V  R  Q  Y  D  Q  I  L  I  E  I  C  G  H  K  A  I  G  T  V  L  V  G  P  T  P  V  N  I  I  G  R  N  L  L  T
____________________________________________HIV1 (IIIB) GAG/PRO GENE_____________________________________________>

      3730      3740      3750      3760      3770      3780      3790      3800
AGATTGGTTGCACTTTAAATTTTTAACCCGGGGGATCCCGATTTTTATGACTAGTTAATCAAATAAAAAGCATACAAGCTATTGCTTC
TCTAACCAACGTGAAATTTAAAAATTGGGCCCCCTAGGGCTAAAAATACTGATCAATTAGTTTATTTTTCGTATGTTCGATAACGAAG
Q  I  G  C  T  L  N  F             <__________________C3 FLANKING ARM__________________
___HIV1 (IIIB) GAG/PRO____>
```

```
        10         20         30         40         50         60         70         80         90        100        110
     *   *      *   *      *   *      *   *      *   *      *   *      *   *      *   *      *   *      *   *      *   *
GAGCTCGCGG CCGCCTATCA AAAGTCTTAA TGAGTTAGGT GTAGATAGTA TAGATATTAC TACAAAGGTA TTCATATTTC CTATCAATTC TAAAGTAGAT GATATTAATA
CTCGAGCGCC GGCGGATAGT TTTCAGAATT ACTCAATCCA CATCTATCAT ATCTATAATG ATGTTTCCAT AAGTATAAAG GATAGTTAAG ATTTCATCTA CTATAATTAT

       120        130        140        150        160        170        180        190        200        210        220
     *   *      *   *      *   *      *   *      *   *      *   *      *   *      *   *      *   *      *   *      *   *
ACTCAAAGAT GATGATAGTA GATAATAGAT ACGCTCATAT AATGACTGCA AATTTGGACG GTTCACATTT TAATCATCAC GCGTTCATAA GTTTCAACTG CATAGATCAA
TGAGTTTCTA CTACTATCAT CTATTATCTA TGCGAGTATA TTACTGACGT TTAAACCTGC CAAGTGTAAA ATTAGTAGTG CGCAAGTATT CAAAGTTGAC GTATCTAGTT

       230        240        250        260        270        280        290        300        310        320        330
     *   *      *   *      *   *      *   *      *   *      *   *      *   *      *   *      *   *      *   *      *   *
AATCTCACTA AAAAGATAGC CGATGTATTT GAGAGAGATT GGACATCTAA CTACGCTAAA GAAATTACAG TTATAAATAA TACATAATGG ATTTTGTTAT CATCAGTTAT
TTAGAGTGAT TTTTCTATCG GCTACATAAA CTCTCTCTAA CCTGTAGATT GATGCGATTT CTTTAATGTC AATATTTATT ATGTATTACC TAAAACAATA GTAGTCAATA

       340        350        360        370        380        390        400        410        420        430        440
     *   *      *   *      *   *      *   *      *   *      *   *      *   *      *   *      *   *      *   *      *   *
ATTTAACATA AGTACAATAA AAAGTATTAA ATAAAAATAC TTACTTACGA AAAAATGACT AATTAGCTAT AAAAACCCAG ATCTCTCGAG GTCGACGGTA TCGATAAGCT
TAAATTGTAT TCATGTTATT TTTCATAATT TATTTTTATG AATGAATGCT TTTTTACTGA TTAATCGATA TTTTTGGGTC TAGAGAGCTC CAGCTGCCAT AGCTATTCGA

       450        460           470         480         490         500         510         520         530
     *   *      *   *        *   *      *     *      *     *      *     *      *     *      *     *      *     *
TGATATCGAA TTCATAAAAA TT A TTG ATG TCT ACA CAT CCT TTT GTA ATT GAC ATC TAT ATA TCC TTT TGT ATA ATC AAC TCT AAT CAC TTT
ACTATAGCTT AAGTATTTTT AA T AAC TAC AGA TGT GTA GGA AAA CAT TAA CTG TAG ATA TAT AGG AAA ACA TAT TAG TTG AGA TTA GTG AAA
                           <Q   H   R   C   M   R   K   Y   N   V   D   I   Y   G   K   T   Y   D   V   R   I   V   K
                           -----------------------------------------k3L---------------------------------------------
```

FIG.6B

```
540            550          560          570          580          590          600          610          620
 *       *      *     *      *     *      *     *      *     *      *     *      *     *      *     *      *
AAC TTT TAC AGT TTT CCC TAC CAG TTT ATC CCT ATA TTC AAC ATA TCT ATC CAT ATG CAT CTT AAC ACT CTC TGC CAA GAT AGC TTC AGA
TTG AAA ATG TCA AAA GGG ATG GTC AAA TAG GGA TAT AAG TTG TAT AGA TAG GTA TAC GTA GAA TTG TGA GAG ACG GTT CTA TCG AAG TCT
<V   K   V   T   K   G   V   L   K   D   R   Y   E   V   Y   R   D   M   H   M   K   V   S   E   A   L   I   A   E   S
------------------------------------------------------------------K3L------------------------------------------

    630          640          650          660          670          680          690          700          710
 *       *      *     *      *     *      *     *      *     *      *     *      *     *      *     *      *
GTG AGG ATA GTC AAA AAG ATA AAT GTA TAG AGC ATA ATC CTT CTC GTA TAC TCT GCC CTT TAT TAC ATC GCC CGC ATT GGG CAA CGA ATA
CAC TCC TAT CAG TTT TTC TAT TTA CAT ATC TCG TAT TAG GAA GAG CAT ATG AGA CGG GAA ATA ATG TAG CGG GCG TAA CCC GTT GCT TAT
<H   P   Y   D   F   L   Y   I   Y   L   A   Y   D   K   E   Y   V   R   G   K   I   V   D   G   A   N   P   L   S   Y
------------------------------------------------------------------K3L------------------------------------------

    720          730        740        750        760        770        780        790        800        810
 *       *      *     *     *     *     *     *     *     *     *     *     *     *     *     *     *     *
ACA AAA TGC AAG CAT ACG ATACAAACTT AACGGATATC GCGATAATGA AATAATTTAT GATTATTTCT CGCTTTCAAT TTAACACAAC CCTCAAGAAC
TGT TTT ACG TTC GTA TGC TATGTTTGAA TTGCCTATAG CGCTATTACT TTATTAAATA CTAATAAAGA GCGAAAGTTA AATTGTGTTG GGAGTTCTTG
<C   F   A   L   M
----------------K3L

    820        830        840        850        860        870        880        890        900        910        920
 *     *     *     *     *     *     *     *     *     *     *     *     *     *     *     *     *     *     *     *     *     *
CTTTGTATTT ATTTTCACTT TTTAAGTATA GAATAAAGAA AGCTCTAATT AATTAATGAA CAGATTGTTT CGTTTTCCCC TTGGCGTATC ACTAATTAAT TAACCCGGGC
GAAACATAAA TAAAAGTGAA AAATTCATAT CTTATTTCTT TCGAGATTAA TTAATTACTT GTCTAACAAA GCAAAAGGGG AACCGCATAG TGATTAATTA ATTGGGCCCG

    930        940        950        960        970        980        990       1000       1010       1020       1030
 *     *     *     *     *     *     *     *     *     *     *     *     *     *     *     *     *     *     *     *     *     *
TGCAGCTCGA GGAATTCAAC TATATCGACA TATTTCATTT GTATACACAT AACCATTACT AACGTAGAAT GTATAGGAAG AGATGTAACG GGAACAGGGT TTGTTGATTC
ACGTCGAGCT CCTTAAGTTG ATATAGCTGT ATAAAGTAAA CATATGTGTA TTGGTAATGA TTGCATCTTA CATATCCTTC TCTACATTGC CCTTGTCCCA AACAACTAAG

   1040       1050       1060       1070       1080       1090       1100       1110       1120       1130       1140
 *     *     *     *     *     *     *     *     *     *     *     *     *     *     *     *     *     *     *     *     *     *
GCAAACTATT CTAATACATA ATTCTTCTGT TAATACGTCT TGCACGTAAT CTATTATAGA TGCCAAGATA TCTATATAAT TATTTTGTAA GATGATGTTA ACTATGTGAT
CGTTTGATAA GATTATGTAT TAAGAAGACA ATTATGCAGA ACGTGCATTA GATAATATCT ACGGTTCTAT AGATATATTA ATAAAACATT CTACTACAAT TGATACACTA
```

FIG. 6C

```
       1150       1160       1170       1180       1190       1200       1210       1220       1230       1240       1250
    *     *     *     *     *     *     *     *     *     *     *     *     *     *     *     *     *     *     *     *     *     *
CTATATAAGT AGTGTAATAA TTCATGTATT TCGATATATG TTCCAACTCT GTCTTTGTGA TGTCTAGTTT CGTAATATCT ATAGCATCCT CAAAAAATAT ATTCGCATAT
GATATATTCA TCACATTATT AAGTACATAA AGCTATATAC AAGGTTGAGA CAGAAACACT ACAGATCAAA GCATTATAGA TATCGTAGGA GTTTTTTATA TAAGCGTATA

       1260       1270       1280       1290       1300       1310       1320       1330       1340       1350       1360
    *     *     *     *     *     *     *     *     *     *     *     *     *     *     *     *     *     *     *     *     *     *
ATTCCCAAGT CTTCAGTTCT ATCTTCTAAA AAATCTTCAA CGTATGGAAT ATAATAATCT ATTTTACCTC TTCTGATATC ATTAATGATA TAGTTTTTGA CACTATCTTC
TAAGGGTTCA GAAGTCAAGA TAGAAGATTT TTTAGAAGTT GCATACCTTA TATTATTAGA TAAAATGGAG AAGACTATAG TAATTACTAT ATCAAAAACT GTGATAGAAG

       1370       1380       1390       1400       1410       1420       1430       1440       1450       1460       1470
    *     *     *     *     *     *     *     *     *     *     *     *     *     *     *     *     *     *     *     *     *     *
TGTCAATTGA TTCTTATTCA CTATATCTAA GAAACGGATA GCGTCCCTAG GACGAACTAC TGCCATTAAT ATCTCTATTA TAGCTTCTGG ACATAATTCA TCTATTATAC
ACAGTTAACT AAGAATAAGT GATATAGATT CTTTGCCTAT CGCAGGGATC CTGCTTGATG ACGGTAATTA TAGAGATAAT ATCGAAGACC TGTATTAAGT AGATAATATG

       1480       1490       1500       1510       1520       1530       1540       1550       1560       1570       1580
    *     *     *     *     *     *     *     *     *     *     *     *     *     *     *     *     *     *     *     *     *     *
CAGAATTAAT GGGAACTATT CCGTATCTAT CTAACATAGT TTTAAGAAAG TCAGAATCTA AGACCTGATG TTCATATATT GGTTCATACA TGAAATGATC TCTATTGATG
GTCTTAATTA CCCTTGATAA GGCATAGATA GATTGTATCA AAATTCTTTC AGTCTTAGAT TCTGGACTAC AAGTATATAA CCAAGTATGT ACTTTACTAG AGATAACTAC

       1590       1600       1610       1620       1630       1640       1650       1660       1670       1680       1690
    *     *     *     *     *     *     *     *     *     *     *     *     *     *     *     *     *     *     *     *     *     *
ATAGTGACTA TTTCATTCTC TGAAAATTGG TAACTCATTC TATATATGCT TTCCTTGTTG ATGAAGGATA GAATATACTC AATAGAATTT GTACCAACAA ACTGTTCTCT
TATCACTGAT AAAGTAAGAG ACTTTTAACC ATTGAGTAAG ATATATACGA AAGGAACAAC TACTTCCTAT CTTATATGAG TTATCTTAAA CATGGTTGTT TGACAAGAGA
```

FIG. 6D

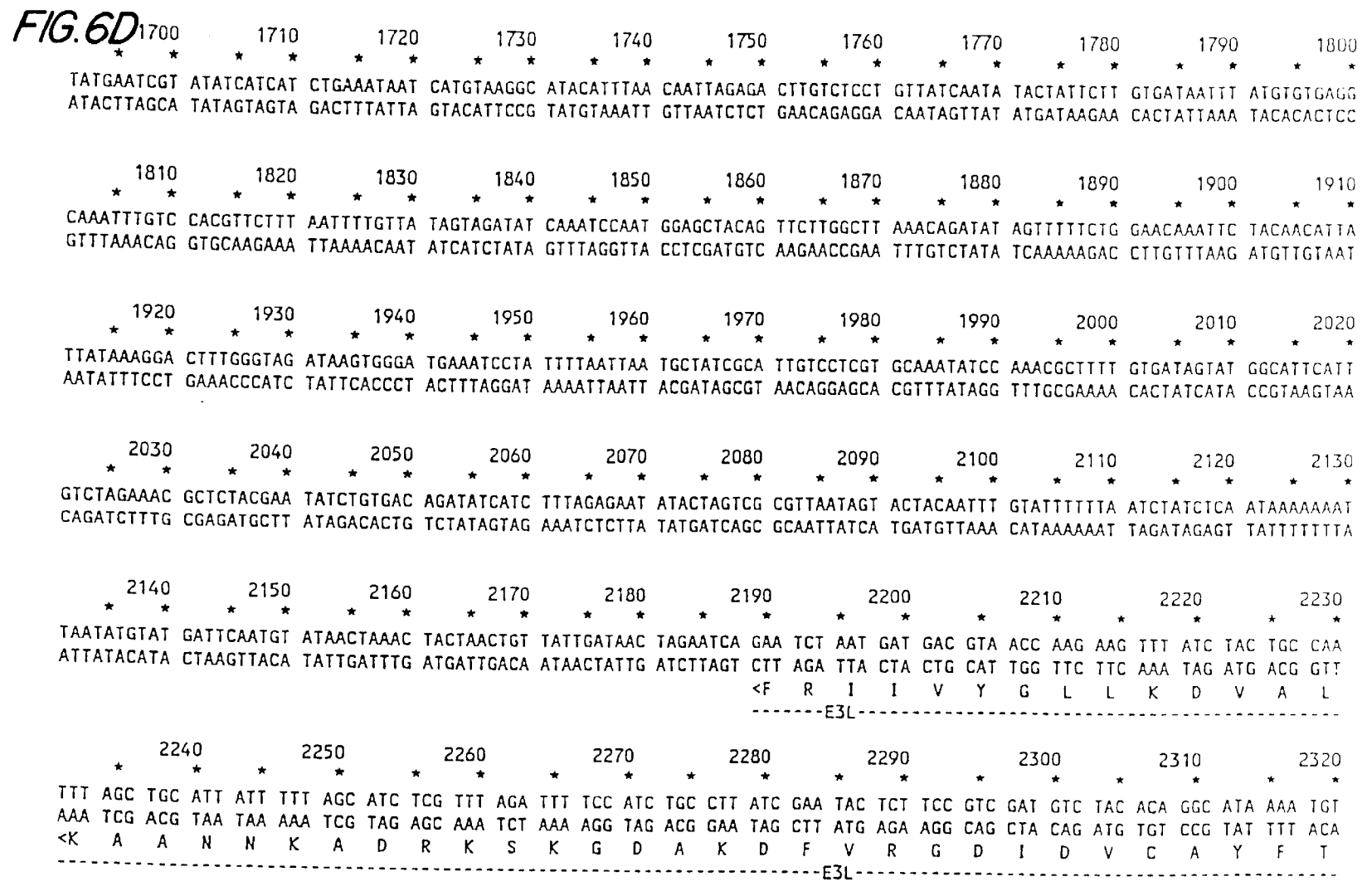

```
1700        1710       1720       1730       1740       1750       1760       1770       1780       1790       1800
TATGAATCGT ATATCATCAT CTGAAATAAT CATGTAAGGC ATACATTTAA CAATTAGAGA CTTGTCTCCT GTTATCAATA TACTATTCTT GTGATAATTT ATGTGTGAGG
ATACTTAGCA TATAGTAGTA GACTTTATTA GTACATTCCG TATGTAAATT GTTAATCTCT GAACAGAGGA CAATAGTTAT ATGATAAGAA CACTATTAAA TACACACTCC

      1810       1820       1830       1840       1850       1860       1870       1880       1890       1900       1910
CAAATTTGTC CACGTTCTTT AATTTTGTTA TAGTAGATAT CAAATCCAAT GGAGCTACAG TTCTTGGCTT AAACAGATAT AGTTTTTCTG GAACAAATTC TACAACATTA
GTTTAAACAG GTGCAAGAAA TTAAAACAAT ATCATCTATA GTTTAGGTTA CCTCGATGTC AAGAACCGAA TTTGTCTATA TCAAAAAGAC CTTGTTTAAG ATGTTGTAAT

      1920       1930       1940       1950       1960       1970       1980       1990       2000       2010       2020
TTATAAAGGA CTTTGGGTAG ATAAGTGGGA TGAAATCCTA TTTTAATTAA TGCTATCGCA TTGTCCTCGT GCAAATATCC AAACGCTTTT GTGATAGTAT GGCATTCATT
AATATTTCCT GAAACCCATC TATTCACCCT ACTTTAGGAT AAAATTAATT ACGATAGCGT AACAGGAGCA CGTTTATAGG TTTGCGAAAA CACTATCATA CCGTAAGTAA

      2030       2040       2050       2060       2070       2080       2090       2100       2110       2120       2130
GTCTAGAAAC GCTCTACGAA TATCTGTGAC AGATATCATC TTTAGAGAAT ATACTAGTCG CGTTAATAGT ACTACAATTT GTATTTTTTA ATCTATCTCA ATAAAAAAAT
CAGATCTTTG CGAGATGCTT ATAGACACTG TCTATAGTAG AAATCTCTTA TATGATCAGC GCAATTATCA TGATGTTAAA CATAAAAAAT TAGATAGAGT TATTTTTTTA

      2140       2150       2160       2170       2180       2190        2200        2210        2220        2230
TAATATGTAT GATTCAATGT ATAACTAAAC TACTAACTGT TATTGATAAC TAGAATCA GAA TCT AAT GAT GAC GTA ACC AAG AAG TTT ATC TAC TGC CAA
ATTATACATA CTAAGTTACA TATTGATTTG ATGATTGACA ATAACTATTG ATCTTAGT CTT AGA TTA CTA CTG CAT TGG TTC TTC AAA TAG ATG ACG GTT
                                                               <F   R   I   I   V   Y   G   L   L   K   D   V   A   L
                                                               -------E3L-------------------------------------------

        2240        2250        2260        2270        2280        2290        2300        2310        2320
TTT AGC TGC ATT ATT TTT AGC ATC TCG TTT AGA TTT TCC ATC TGC CTT ATC GAA TAC TCT TCC GTC GAT GTC TAC ACA GGC ATA AAA TGT
AAA TCG ACG TAA TAA AAA TCG TAG AGC AAA TCT AAA AGG TAG ACG GAA TAG CTT ATG AGA AGG CAG CTA CAG ATG TGT CCG TAT TTT ACA
<K   A   A   N   N   K   A   D   R   K   S   K   G   D   A   K   D   F   V   R   G   D   I   D   V   C   A   Y   F   T
-------------------------------------------------------------E3L--------------------------------------------------------
```

FIG.6E

```
2330        2340        2350        2360        2370        2380        2390        2400        2410
AGG AGA GTT ACT AGG CCC AAC TGA TTC AAT ACG AAA AGA CCA ATC TCT CTT AGT TAT TTG GCA GTA CTC ATT AAT AAT GGT GAC AGG GTT
TCC TCT CAA TGA TCC GGG TTG ACT AAG TTA TGC TTT TCT GGT TAG AGA GAA TCA ATA AAC CGT CAT GAG TAA TTA TTA CCA CTG TCC CAA
<P   S   N   S   P   G   V   S   E   I   R   F   S   W   D   R   K   T   I   Q   C   Y   E   N   I   I   T   V   P   N
-----------------------------------------------------------------E3L----------------------------------------------

        2420        2430        2440        2450        2460        2470        2480        2490        2500
AGC ATC TTT CCA ATC AAT AAT TTT TTT AGC CGG AAT AAC ATC ATC AAA AGA CTT ATG ATC CTC TCT CAT TGA TTT TTC GCG GGA TAC ATC
TCG TAG AAA GGT TAG TTA TTA AAA AAA TCG GCC TTA TTG TAG TAG TTT TCT GAA TAC TAG GAG AGA GTA ACT AAA AAG CGC CCT ATG TAG
<A   D   K   W   D   I   I   K   K   A   P   I   V   D   D   F   S   K   H   D   E   R   M   S   K   E   R   S   V   D
-----------------------------------------------------------------E3L----------------------------------------------

        2510        2520        2530        2540        2550        2560        2570        2580        2590
ATC TAT TAT GAC GTC AGC CAT AGC ATC AGC ATC CGG CTT ATC CGC CTC CGT TGT CAT AAA CCA ACG AGG AGG AAT ATC GTC GGA GCT GTA
TAG ATA ATA CTG CAG TCG GTA TCG TAG TCG TAG GCC GAA TAG GCG GAG GCA ACA GTA TTT GGT TGC TCC TCC TTA TAG CAG CCT CGA CAT
<D   I   I   V   D   A   M   A   D   A   D   P   K   D   A   E   T   T   M   F   W   R   P   P   I   D   D   S   S   Y
-----------------------------------------------------------------E3L----------------------------------------------

        2600        2610        2620        2630        2640        2650        2660        2670        2680
CAC CAT AGC ACT ACG TTG AAG ATC GTA CAG AGC TTT ATT AAC TTC TCG CTT CTC CAT ATT AAG TTG TCT AGT TAG TTG TGC AGC AGT AGC
GTG GTA TCG TGA TGC AAC TTC TAG CAT GTC TCG AAA TAA TTG AAG AGC GAA GAG GTA TAA TTC AAC AGA TCA ATC AAC ACG TCG TCA TCG
<V   M   A   S   R   Q   L   D   Y   L   A   K   N   V   E   R   K   E   M   N   L   Q   R   T   L   Q   A   A   T   A
-----------------------------------------------------------------E3L----------------------------------------------

        2690        2700        2710        2720        2730        2740        2750        2760        2770
TCC TTC GAT TCC AAT GTT TTT AAT AGC CGC ACA CAC AAT CTC TGC GTC AGA ACG CTC GTC AAT ATA GAT CTT AGA CAT TT TTAGAGAGAA
AGG AAG CTA AGG TTA CAA AAA TTA TCG GCG TGT GTG TTA GAG ACG CAG TCT TGC GAG CAG TTA TAT CTA GAA TCT GTA AA AATCTCTCTT
<G   E   I   G   I   N   K   I   A   A   C   V   I   E   A   D   S   R   E   D   I   Y   I   K   S   M
-----------------------------------------------------------------E3L--------------------------
```

FIG. 6F

```
      2780       2790       2800       2810       2820       2830       2840       2850       2860       2870       2880
   *    *     *    *     *    *     *    *     *    *     *    *     *    *     *    *     *    *     *    *     *    *
CTAACACAAC CAGCAATAAA ACTGAACCTA CTTTATCATT TTTTTATTCA TCATCCTCTG GTGGTTCGTC GTTTCTATCG AATGTAGCTC TGATTAACCC GTCATCTATA
GATTGTGTTG GTCGTTATTT TGACTTGGAT GAAATAGTAA AAAAATAAGT AGTAGGAGAC CACCAAGCAG CAAAGATAGC TTACATCGAG ACTAATTGGG CAGTAGATAT

      2890       2900       2910       2920       2930       2940       2950       2960       2970       2980       2990
   *    *     *    *     *    *     *    *     *    *     *    *     *    *     *    *     *    *     *    *     *    *
GGTGATGCTG GTTCTGGAGA TTCTGGAGGA GATGGATTAT TATCTGGAAG AATCTCTGTT ATTTCCTTGT TTTCATGTAT CGATTGCGTT GTAACATTAA GATTGCGAAA
CCACTACGAC CAAGACCTCT AAGACCTCCT CTACCTAATA ATAGACCTTC TTAGAGACAA TAAAGGAACA AAAGTACATA GCTAACGCAA CATTGTAATT CTAACGCTTT

      3000       3010       3020       3030       3040       3050       3060       3070       3080       3090       3100
   *    *     *    *     *    *     *    *     *    *     *    *     *    *     *    *     *    *     *    *     *    *
TGCTCTAAAT TTGGGAGGCT TAAAGTGTTG TTTGCAATCT CTACACGCGT GTCTAACTAG TGGAGGTTCG TCAGCTGCTC TAGTTTGAAT CATCATCGGC GTAGTATTCC
ACGAGATTTA AACCCTCCGA ATTTCACAAC AAACGTTAGA GATGTGCGCA CAGATTGATC ACCTCCAAGC AGTCGACGAG ATCAAACTTA GTAGTAGCCG CATCATAAGG

      3110       3120       3130       3140       3150       3160       3170       3180       3190       3200       3210
   *    *     *    *     *    *     *    *     *    *     *    *     *    *     *    *     *    *     *    *     *    *
TACTTTTACA GTTAGGACAC GGTGTATTGT ATTTCTCGTC GAGAACGTTA AAATAATCGT TGTAACTCAC ATCCTTTATT TTATCTATAT TGTATTCTAC TCCTTTCTTA
ATGAAAATGT CAATCCTGTG CCACATAACA TAAAGAGCAG CTCTTGCAAT TTTATTAGCA ACATTGAGTG TAGGAAATAA AATAGATATA ACATAAGATG AGGAAAGAAT

      3220       3230       3240       3250       3260       3270       3280       3290       3300       3310       3320
   *    *     *    *     *    *     *    *     *    *     *    *     *    *     *    *     *    *     *    *     *    *
ATGCATTTTA TACCGAATAA GAGATAGCGA AGGAATTCTT TTTATTGATT AACTAGTCAA ATGAGTATAT ATAATTGAAA AAGTAAAATA TAAATCATAT AATAATGAAA
TACGTAAAAT ATGGCTTATT CTCTATCGCT TCCTTAAGAA AAATAACTAA TTGATCAGTT TACTCATATA TATTAACTTT TTCATTTTAT ATTTAGTATA TTATTACTTT
```

FIG. 6G

```
      3330       3340       3350       3360       3370       3380       3390       3400       3410       3420       3430
   *     *    *     *    *     *    *     *    *     *    *     *    *     *    *     *    *     *    *     *    *     *
CGAAATATCA GTAATAGACA GGAACTGGCA GATTCTTCTT CTAATGAAGT AAGTACTGCT AAATCTCCAA AATTAGATAA AAATGATACA GCAAATACAG CTTCATTCAA
GCTTTATAGT CATTATCTGT CCTTGACCGT CTAAGAAGAA GATTACTTCA TTCATGACGA TTTAGAGGTT TTAATCTATT TTTACTATGT CGTTTATGTC GAAGTAAGTT

      3440       3450       3460       3470       3480       3490       3500       3510       3520       3530       3540
   *     *    *     *    *     *    *     *    *     *    *     *    *     *    *     *    *     *    *     *    *     *
CGAATTACCT TTTAATTTTT TCAGACACAC CTTATTACAA ACTAACTAAG TCAGATGATG AGAAAGTAAA TATAAATTTA ACTTATGGGT ATAATATAAT AAAGATTCAT
GCTTAATGGA AAATTAAAAA AGTCTGTGTG GAATAATGTT TGATTGATTC AGTCTACTAC TCTTTCATTT ATATTTAAAT TGAATACCCA TATTATATTA TTTCTAAGTA

      3550       3560       3570       3580       3590       3600       3610       3620       3630       3640       3650
   *     *    *     *    *     *    *     *    *     *    *     *    *     *    *     *    *     *    *     *    *     *
GATATTAATA ATTTACTTAA CGATGTTAAT AGACTTATTC CATCAACCCC TTCAAACCTT TCTGGATATT ATAAAATACC AGTTAATGAT ATTAAAATAG ATTGTTTAAG
CTATAATTAT TAAATGAATT GCTACAATTA TCTGAATAAG GTAGTTGGGG AAGTTTGGAA AGACCTATAA TATTTTATGG TCAATTACTA TAATTTTATC TAACAAATTC

      3660       3670       3680       3690       3700       3710       3720       3730       3740       3750       3760
   *     *    *     *    *     *    *     *    *     *    *     *    *     *    *     *    *     *    *     *    *     *
AGATGTAAAT AATTATTTGG AGGTAAAGGA TATAAAATTA GTCTATCTTT CACATGGAAA TGAATTACCT AATATTAATA ATTATGATAG GAATTTTTTA GGATTTACAG
TCTACATTTA TTAATAAACC TCCATTTCCT ATATTTTAAT CAGATAGAAA GTGTACCTTT ACTTAATGGA TTATAATTAT TAATACTATC CTTAAAAAAT CCTAAATGTC

      3770       3780       3790       3800       3810       3820       3830       3840       3850       3860       3870
   *     *    *     *    *     *    *     *    *     *    *     *    *     *    *     *    *     *    *     *    *     *
CTGTTATATG TATCAACAAT ACAGGCAGAT CTATGGTTAT GGTAAAACAC TGTAACGGGA AGCAGCATTC TATGGTAACT GGCCTATGTT TAATAGCCAG ATCATTTTAC
GACAATATAC ATAGTTGTTA TGTCCGTCTA GATACCAATA CCATTTTGTG ACATTGCCCT TCGTCGTAAG ATACCATTGA CCGGATACAA ATTATCGGTC TAGTAAAATG

      3880       3890       3900       3910       3920       3930       3940       3950       3960       3970       3980
   *     *    *     *    *     *    *     *    *     *    *     *    *     *    *     *    *     *    *     *    *     *
TCTATAAACA TTTTACCACA AATAATAGGA TCCTCTAGAT ATTTAATATT ATATCTAACA ACAACAAAAA AATTTAACGA TGTATGGCCA GAAGTATTTT CTACTAATAA
AGATATTTGT AAAATGGTGT TTATTATCCT AGGAGATCTA TAAATTATAA TATAGATTGT TGTTGTTTTT TTAAATTGCT ACATACCGGT CTTCATAAAA GATGATTATT
```

FIG. 6H

```
      3990       4000       4010       4020       4030       4040       4050       4060       4070       4080       4090
    *    *     *    *     *    *     *    *     *    *     *    *     *    *     *    *     *    *     *    *     *    *
AGATAAAGAT AGTCTATCTT ATCTACAAGA TATGAAAGAA GATAATCATT TAGTAGTAGC TACTAATATG GAAAGAAATG TATACAAAAA CGTGGAAGCT TTTATATTAA
TCTATTTCTA TCAGATAGAA TAGATGTTCT ATACTTTCTT CTATTAGTAA ATCATCATCG ATGATTATAC CTTTCTTTAC ATATGTTTTT GCACCTTCGA AAATATAATT

      4100       4110       4120       4130       4140       4150       4160       4170       4180       4190       4200
    *    *     *    *     *    *     *    *     *    *     *    *     *    *     *    *     *    *     *    *     *    *
ATAGCATATT ACTAGAAGAT TTAAAATCTA GACTTAGTAT AACAAAACAG TTAAATGCCA ATATCGATTC TATATTTCAT CATAACAGTA GTACATTAAT CAGTGATATA
TATCGTATAA TGATCTTCTA AATTTTAGAT CTGAATCATA TTGTTTTGTC AATTTACGGT TATAGCTAAG ATATAAAGTA GTATTGTCAT CATGTAATTA GTCACTATAT

      4210       4220       4230       4240       4250       4260       4270       4280       4290       4300       4310
    *    *     *    *     *    *     *    *     *    *     *    *     *    *     *    *     *    *     *    *     *    *
CTGAAACGAT CTACAGACTC AACTATGCAA GGAATAAGCA ATATGCCAAT TATGTCTAAT ATTTTAACTT TAGAACTAAA ACGTTCTACC AATACTAAAA ATAGGATACG
GACTTTGCTA GATGTCTGAG TTGATACGTT CCTTATTCGT TATACGGTTA ATACAGATTA TAAAATTGAA ATCTTGATTT TGCAAGATGG TTATGATTTT TATCCTATGC

      4320       4330       4340       4350       4360       4370       4380       4390       4400       4410       4420
    *    *     *    *     *    *     *    *     *    *     *    *     *    *     *    *     *    *     *    *     *    *
TGATAGGCTG TTAAAAGCTG CAATAAATAG TAAGGATGTA GAAGAAATAC TTTGTTCTAT ACCTTCGGAG GAAAGAACTT TAGAACAACT TAAGTTTAAT CAAACTTGTA
ACTATCCGAC AATTTTCGAC GTTATTTATC ATTCCTACAT CTTCTTTATG AAACAAGATA TGGAAGCCTC CTTTCTTGAA ATCTTGTTGA ATTCAAATTA GTTTGAACAT

      4430
    *    *
TTTATGAAGG TACC
AAATACTTCC ATGG
```

VECTORS HAVING ENHANCED EXPRESSION, AND METHODS OF MAKING AND USES THEREOF

RELATED APPLICATIONS

Reference is made to the copending applications of Paoletti et al., U.S. Ser. Nos. 08/417,210, 08/303,275, 08/709,209, 08/184,009 (incorporating by reference U.S. Ser. No. 07/805,567, from which U.S. Pat. No. 5,378,457 issued) and U.S. Ser. No. 08/521,016 and to U.S. Pat. Nos. 5,378,457, 5,225,336, 5,453,364, 5,494,807, 5,505,941, and 5,110,587, all of which are incorporated herein by reference.

FIELD OF THE INVENTION

The present invention relates to enhanced vectors, and methods for making and using them. The vectors can have enhanced translation and/or expression, e.g., translation and/or expression from a nucleotide sequence of interest.

Several publications are referenced in this application. Full citation to these publications is found where cited or at the end of the specification, immediately preceding the claims or where the publication is mentioned; and each of these publications is hereby incorporated by reference. These publications relate to the state of the art to which the invention pertains; however, there is no admission that any of these publications is indeed prior art.

BACKGROUND OF THE INVENTION

DNA such as plasmids or naked DNA, and other vectors, such as viral vectors, e.g., vaccinia virus and more recently other poxviruses, have been used for the insertion and expression from foreign genes. The basic technique of inserting foreign genes into live infectious poxvirus involves recombination between pox DNA sequences flanking a foreign genetic element in a donor plasmid and homologous sequences present donor plasmid and homologous sequences present in the rescuing poxvirus (Piccini et al., 1987). Recombinant poxviruses are constructed in steps known as in or analogous to methods in U.S. Pat. Nos. 4,769,330, 4,772,848, 4,603,112, 5,505,941, and 5,494,807, incorporated herein by reference. A desire in vector development is attenuated vectors, e.g., for enhanced safety; for instance, so that the vector may be employed in an immunological or vaccine composition.

For instance, the NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen. Likewise, the ALVAC vector, a vaccine strain of canarypox virus, has also proven effective as a recombinant viral vaccine vector (Perkus et al., 1995). In non-avian hosts, both these vectors do not productively replicate (with some exceptions as to NYVAC). Since all poxviruses replicate in the cytoplasm and encode most, if not all of the proteins required for viral transcription (Moss 1990), appropriately engineered foreign coding sequences under the control of poxvirus promoters are transcribed and translated in the absence of productive viral replication.

It would be an improvement over the state of the art to provide enhanced vectors, e.g., vectors having enhanced transcription or transcription and translation and/or expression, for instance such vectors which are attenuated; especially since attenuation may raise issues of expression levels and/or persistence, and it would be an advancement to address such issues.

OBJECTS AND SUMMARY OF THE INVENTION

Recent studies on vaccinia replication have revealed certain poxvirus-encoded functions which play a role in the regulation of viral transcription and translation (reviewed in Moss, 1990; Moss, 1992). Some of these vaccinia encoded functions (e.g., K3L, E3L, and combinations thereof) have now surprisingly been utilized to increase the levels and persistence of gene expression (e.g., foreign gene expression) in vectors (e.g., the ALVAC vectors); and, are exemplary of the inventive vectors and methods.

Objects of the present invention may include at least one of: providing a method for increasing translation and/or expression from at least one nucleotide sequence of interest by a vector, such as a coding nucleotide sequence by a vector; a vector having enhanced translation; providing a method for preparing a vector having enhanced translation and/or expression; providing a method for enhancing translation and/or expression from a vector; providing an improved vector, such as poxvirus vectors, e.g., improved NYVAC, ALVAC or TROVAC vectors; and, products therefrom.

The invention therefore provides a vector for enhanced expression of at least one first nucleotide sequence in a cell. The vector can be modified to comprise the first nucleotide sequence. The vector is modified to comprise at least one second nucleotide sequence encoding a translation factor. Preferably there is substantially co-temporal expression from the first and second nucleotide sequences. Expression of the second nucleotide sequence enhances expression of the first nucleotide sequence by enhancing translation. Preferably the vector is employed in a cell in which enhanced translation results from the translation factor.

The first nucleotide sequence can be operably linked to a first promoter and the second nucleotide sequence can be operably linked to a second promoter, and the first and second promoters are preferably functional substantially co-temporally or contemporaneously. Thus, the first and second nucleotide sequences can be at different loci within the vector. The first and second nucleotide sequences also can be at the same locus within the vector, using the first and second promoters; or, by the first nucleotide sequence and the second nucleotide sequence being operably linked to a promoter.

The translation factor can effect inhibition of eIF-2$\alpha$ phosphorylation or inhibition of PKR phosphorylation or otherwise sequesters dsRNA leading to an increase of the effective concentration of dsRNA. The second nucleotide sequence can be from the group consisting of: a K3L open reading frame, an E3L open reading frame, a viral associated RNA I (VAI), an EBER RNA, a sigma 3 open reading frame, a TRBP open reading frame, and combinations thereof.

The first nucleotide sequence can be selected from the group of sequences encoding an epitope of interest, a biological response modulator, a growth factor, a recognition sequence, a therapeutic gene and a fusion protein.

The vector can be a recombinant virus, such as a poxvirus; for instance, an orthopoxvirus or an avipoxvirus, e.g., a vaccinia virus, a fowlpox virus, a canarypox virus; preferably an attenuated virus such as an attenuated poxvirus, e.g., NYVAC, ALVAC, or TROVAC.

The invention further provides a method for preparing a an inventive vector comprising modifying the vector to comprise the at least one second nucleotide sequence. The method can also include modifying the vector so that it comprises the at least one first nucleotide sequence. Preferably the vector is so modified that there is substantially co-temporal or contemporaneous expression of the first and second nucleotide sequences; and, more preferably, the vector is also so modified that the translation factor is with respect to the cell in which the vector is to be employed.

The method can comprise operably linking the first nucleotide sequence to a first promoter and the second nucleotide sequence to a second promoter, wherein the first and second promoters are functional substantially co-temporally or contemporaneously. The method can also comprise operably linking the first and second nucleotide sequences to a promoter.

The invention further provides an immunological, vaccine or therapeutic composition comprising at least one inventive vector and a pharmaceutically acceptable carrier or diluent.

The invention even still further provides a method for generating an immunological or therapeutic response in a host (animal, human, vertebrate, mammal, etc.) comprising administering to the host at least one inventive composition.

The invention additionally provides a method for increasing expression from at least one first nucleotide sequence by a vector comprising the first nucleotide sequence. The method comprises modifying the vector to comprise at least one second nucleotide sequence encoding a translation factor. There is preferably substantially co-temporal or contemporaneous expression of the first and second nucleotide sequences. Expression can be in a cell; and it is more preferred to have the translation factor expressed in a cell in which there is enhancement from expression of the particular translation factor. Expression of the second nucleotide sequence enhances expression of the first nucleotide sequence by enhancing translation. The method can additionally comprise modifying the vector to comprise the first nucleotide sequence.

The invention in yet another embodiment provides a method for expressing at least one gene product in vitro comprising infecting, or transfecting, a suitable cell with at least one inventive vector. The products therefrom can be an epitope of interest, which can be useful in formulating therapeutic, immunological or vaccine compositions; or, for generating antibodies such as monoclonal antibodies; or, in assays, kits, tests and the like, such as diagnostic compositions, e.g., for detection of antibodies.

Thus, the invention can provide compositions and methods for in vitro translation and/or expression involving at least one inventive vector, e.g., methods for producing a gene product (which can be used as an antigen or epitope in a therapeutic, immunological or vaccine composition, or in a diagnostic or detection kit, assay or method, e.g., to ascertain the presence or absence of antibodies, or to generate antibodies, such as monoclonal antibodies, e.g., for use in a diagnostic or detection kit, assay or method), and/or for ex vivo translation and/or expression involving at least one inventive vector, e.g., methods for producing a gene product for stimulating cells for reinfusion into a host (e.g., animal, mammal, vertebrate, human).

Additionally, in a further embodiment the invention provides a method for expressing at least one nucleotide sequence (e.g., the at least one first nucleotide sequence) in vivo comprising administering at least one inventive vector to a host (human, animal, vertebrate, mammal, etc.). The nucleotide sequence can encode an epitope of interest. The method can obtain antibodies. From generating antibodies one can generate monoclonal antibodies; or, antibodies are useful in assays, kits, tests or diagnostic compositions, e.g., for detection of antigens.

The invention can thus provide methods and compositions for in vivo translation and/or expression involving the inventive vectors, e.g., administering at least one inventive vector or a composition comprising at least one inventive vector, for instance, therapeutic, immunological or vaccine compositions comprising at least one inventive vector and a suitable carrier or diluent (e.g., suitable for veterinary and human medicine).

These and other embodiments are disclosed or are obvious from and encompassed by, the following Detailed Description.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which:

FIG. 1 (FIGS. 1A, 1B) shows the nucleotide sequence of the ALVAC C6 insertion site containing the H6/K3L and E3L expression cassette (SEQ ID NO:1);

FIG. 2 shows the DNA sequence of the coding region of FHV gB with modified T5NT motifs (SEQ ID NO:2);

FIG. 3 (FIGS. 3A, 3B, 3C) shows the DNA sequence of the H6 promoted FHV gB donor plasmid pC3H6FHVB (SEQ ID NO:3);

FIG. 4 (FIGS. 4A, 4B, 4C) and

FIG. 5 (FIGS. 5A, 5B, 5C, 5D, 5E, 5F, 5G); show DNA and amino acid sequences (SEQ ID NOS:4,5 and 6) of inserts in vCP1433 and vCP1452; and FIGS. 6A–6H show the DNA sequence (SEQ ID NO:7) of K3L E3L in vCP1452.

DETAILED DESCRIPTION

U.S. Pat. No. 5,494,807, to Paoletti et al., hereby incorporated herein by reference, relates to a modified recombinant virus having inactivated virus-encoded genetic functions so that the recombinant virus has attenuated virulence and enhanced safety. The viruses disclosed in Paoletti et al. can be poxviruses, e.g., a vaccinia virus or an avipox virus, such as fowlpox virus and canarypox virus, e.g., NYVAC, ALVAC and TROVAC. ALVAC was deposited under the terms of the Budapest Treaty with the American Type Culture Collection (ATCC), 10801 University Boulevard, Manassas, Va. 20110–2209 USA, ATCC accession number VR-2547. TROVAC was likewise deposited under the terms of the Budapest Treaty with the ATCC, accession number 2553. And, vCP205, vCP1433, pMPC6H6K3E3 and pC3H6FHVB were also deposited with the ATCC under the terms of the Budapest Treaty, accession numbers VR-2557, VR-2556, 97912, and 97914, respectively, on Mar. 6, 1997.

Like the Paoletti et al. issued U.S. Patent, Falkner et al., WO 95/30018, published Nov. 9, 1995, based on U.S. application Ser. 08/235,392, filed Apr. 24, 1994 (both incorporated herein by reference), relates to poxviruses wherein loci for genetic functions associated with virulence (i.e., loci for "essential" functions) are employed for insertion of exogenous DNA.

Further, recombinants can be made from early ($DNA^-$) and late defective mutants (see Condit and Niles, "Orthopoxvirus Genetics," pp 1–39, In: *Poxviruses*, Edited by R. W. Moyer and P. C. Turner (Springer-Verlag, 1990), and documents cited therein, hereby incoporated herein by reference), or from MVA which is said to be abortive late. Recombinants from defective mutants, abortive late viruses, viruses having essential genetic functions deleted or interrupted, or viruses having expression without productive replication (e.g., ALVAC in mammalian systems) may be said to be attenuated. It would be useful to increase foreign gene expression, e.g., levels of foreign gene expression or persistence of expression, in vectors, especially attenuated vectors.

A means to increase foreign gene expression involves enhancing the overall efficiency of translation, e.g., mRNA translation, such as viral mRNA translation. Two vaccinia encoded functions (E3L and K3L) have recently been identified as playing a role in the regulation of viral translation (Beattie et al., 1995a, 1995b, 1991; Chang et al., 1992; Davies et al., 1993). Both are capable of inhibiting the action of a cellular protein kinase (PKR) which, when activated by double stranded RNA (dsRNA), phosphorylates the translational initiation factor eIF-2α, leading to an inhibition of initiation of mRNA translation (reviewed in Jacobs and Langland, 1996). Vaccinia virus, which produces dsRNA during viral transcription, has thus evolved mechanisms to block the negative action of PKR on eIF-2α and allow for efficient translation of viral mRNA. (Asymetric transcription gives rise to dsRNA; any viral or plasmid-borne expression gives rise to it; dsRNA activates PKR and PKR becomes autophosphorylated, leading to phosphorylation of eIF-2α.)

The vaccinia K3L ORF has been shown to have significant amino acid homology to eIF-2α (Goebel et al., 1990; Beattie et al., 1991; U.S. Pat. No. 5,378,457; see also Beattie et al., 1995a, 1995b). This protein is believed to act as a pseudosubstrate for PKR and competes for the eIF-2α binding site (Carroll et al., 1993; Davies et al., 1992). The K3L gene product can bind to activated PKR and thus prevent phosphorylation of eIF-2α with its resultant negative effect on translation initiation.

The vaccinia E3L gene codes for a protein which is capable of specifically binding to dsRNA (Watson and Jacobs, 1991; Chang et al., 1992). This would tend to lower the amounts of dsRNA in the infected cell, and thus reduce the level of activated PKR. When E3L was deleted from vaccinia, the resulting virus lost this kinase inhibitory function and further allowed activation of the 2'5' oligoadenylate synthetase/RNase L pathway resulting in increased degradation of rRNA (Beattie et al., 1995a, 1995b). Thus, E3L appears to be critical for efficient mRNA translation in vaccinia infected cells at two levels; mRNA stability and limiting eIF-2α phosphorylation.

The ALVAC genome has been sequenced and searched for any homology to E3L/K3L or to any known dsRNA binding protein. Results have revealed no significant homology of any ALVAC ORFS to these two vaccinia ORFS, nor the presence of any dsRNA binding motifs.

Thus, an approach to improving expression levels in recombinant ALVAC vectors was to express the vaccinia E3L/K3L ORFs in ALVAC under the control of early vaccinia promoters. Through inhibition of PKR in the infected cells, the levels and persistence of foreign gene expression could be enhanced.

Hence, ALVAC recombinants as discussed herein were generated in order to enhance foreign gene expression at the transcriptional or transcriptional and translational levels, as examples of the vectors and methods of the present invention.

Thus, exemplified herein is ALVAC recombinants having expression from the vaccinia E3L/K3L genes for enhancing or increasing the levels or persistence of an inserted foreign gene. The up-regulation of foreign gene expression can have a profound effect on the induction of a therapeutic or immunological response in a host administered or inoculated with recombinants derived from these new vectors, thereby leading to an enhanced immunological, e.g., protective, response, or an enhanced therapeutic response.

The scope of the invention, i.e., to manipulate expression from any of E3L and K3L to thereby enhance translational and/or expression efficiency, can be extended to other eukaryotic vector systems (i.e. DNA, viruses).

In fact, viruses in other families have also evolved mechanisms to overcome the cellular anti-viral response of translational down-regulation through PKR activation. In adenoviruses, the VAI RNA, transcribed by RNA pol III, has been well characterized and shown to bind directly to PKR, and thus, prevent its activation by dsRNA (Mathews and Shenk, 1991). Deletion of VAI from the adenovirus genome results in a mutant that replicates poorly and is deficient in levels of late gene expression (Thimmappaya et al., 1982). Similarly, Epstein-Barr virus, a herpesvirus, has an analogous RNA, called EBER, which also acts to prevent PKR activation by directly binding to the kinase (Clark et al., 1991; Sharp et al., 1993). The reovirus sigma 3 gene product has been shown to act in a similar manner as vaccinia E3L in binding dsRNA and thus preventing activation of PKR (Imani and Jacobs, 1988; see also Beattie et al. 1995a). Indeed, one study has shown that the reovirus sigma 3 gene can partially compensate a vaccinia recombinant deleted of E3L (Beattie et al., 1995a). Further, a cellular protein activated upon HIV infection (TRBP) has been shown to inhibit the activity of PKR (Park et al., 1994).

Thus, the present invention broadly relates to manipulation of expression, preferably by employing at least one one translation factor, e.g., a nucleotide sequence encoding a product for overcoming the cellular anti-viral response of translational down-regulation through PKR activation in any eukaryotic vector system; for instance, to increase or enhance expression. And, the invention can pertain to any vector system, including, plasmid or naked DNA vectors, viral vectors, such as poxvirus, adenovirus, herpesvirus, baculovirus, and the like. Thus, the nucleotide sequences can be RNA or DNA, for instance, as is suitable in view of the vector system.

Accordingly, the invention can relate to a vector modified to comprise at least one nucleotide sequence encoding at least one translation factor; a method for increasing translation and/or expression by a vector or for preparing an inventive vector, e.g., by modifying the vector to comprise the at least one nucleotide sequence.

These methods can include substantially co-temporal expression from: (i) a first nucleotide sequence comprising at least one nucleotide sequence of interest, and (ii) a second nucleotide sequence comprising at least one nucleotide sequence encoding a translation factor. The vector also can be modified to comprise the at least one nucleotide sequence of interest. The at least one nucleotide sequence of interest can be at least one coding nucleotide sequence. The vector preferably has substantially co-temporal or contemporaneous expression of the first and second nucleotide sequences.

The substantially co-temporal expression can occur by employing promoters for the first and second nucleotide sequences which are functional at approximately the same time or stage of infection. Thus, the nucleotide sequence of interest and the nucleotide sequences encoding the factor(s) can be positioned at different loci in the vector. Alternatively, substantially co-temporal expression can occur by positioning the first and second nucleotide sequences within the same loci. Thus, substantially co-temporal expression can occur by operably linking to the nucleotide sequence of interest and/or to a promoter operably linked to the nucleotide sequence of interest, a nucleotide sequence encoding a translation factor.

The translation factor can be from any suitable system. Preferably the translation factor can effect inhibition of eIF-2α phosphorylation or inhibition of PKR phosphorylation or otherwise decreases cellular dsRNA content which increases the effective concentration of dsRNA. The translation factor can be selected from expression from the group consisting of: a K3L open reading frame, an E3L open reading frame, a VAI RNA, an EBER RNA, a sigma 3 open reading frame, a TRBP open reading frame, a homolog thereof, and combinations thereof. Thus, at least one nucleotide sequence encoding a K3L open reading frame, an E3L open reading frame, a VAI RNA, an EBER RNA, a sigma 3 open reading frame, a TRBP open reading frame, or homologs thereof, or combinations thereof, can be used in the practice of the invention. The term "effective" with respect to dsRNA concentration means the amount of dsRNA to activate PKR and/or eIF-2α phosphorylation (the dsRNA being in a form therefor). With respect to RNA-based factors, the skilled artisan, without undue experimentation, can obtain suitable DNA therefrom, for use in DNA-based vector systems; and, as to DNA-based factors, the skilled artisan can obtain RNA therefrom for use in RNA-based vector systems.

The term "substantially co-temporal expression" or the term "substantially contemporaneous expression" means that the nucleotide sequence(s) encoding the translation factor(s) are expressed during approximately the same stage of infection as is the at least one nucleotide sequence of interest.

For instance, poxvirus genes are regulated in a temporal manner (Coupar, et al., Eur. J. Immunol., 1986, 16:1479–1487, at 1479). Thus, immediately after infection, a class of "early" genes is expressed (Id.). "Early genes" cease being expressed (i.e., early promoters cease functioning) at a time after infection prior to the "later" stage of infection (DNA replication commencement). The thymidine kinase ("TK") gene and TK promoter is an example of an immediate "early" gene and promoter (Hruby et al., J. Virol., 1982, 43(2):403–409, at 403). The TK gene is switched "off" about four hours after infection. "Late genes" are a class of genes not expressed until DNA replication has commenced (Coupar et al., supra). The PL11 promoter employed by Coupar et al. is an example of a "late" promoter. Thus, in Coupar et al., HA gene expression regulated by the PL11 promoter was not until after DNA replication, despite being in the TK region.

In contrast to canonical "early" genes and "late" genes the 7.5 kD gene and 7.5 kD promoter, is an example of an "early and late" gene and promoter. An "apparent exception to regulated transcription" (Davison and Moss, "Structure of Vaccinia Virus Early Promoters" J. Mol. Biol., 210–69, 249–69 (1989) at 749), the 7.5 kD promoter "contains regulatory signal for both early and late transcription" (Coupar et al., supra). Indeed, there are "independent early and late RNA start sites within the promoter region of the 7.5-kD gene" (Cochran et al., J. Virol., 59(1): 30–37 (April, 1985).

Coupar et al. observed "that temporal regulation of HA expression by the promoters PF [early], P7.5 [early and late] and PL11 [late] was maintained when the promoters were transposed to interrupt the TK gene of [vaccinia virus]" (Id., at 1482). That is, Coupar et al. observed that foreign gene expression under the control of an early vaccinia promoter occurred "early", foreign gene expression under control of a late vaccinia promoter occurred "late", and foreign gene expression under the control of the early and late vaccinia 7.5 kD promoter occurred both early and late (See also id. at 1479: "[p]romoter sequences transposed to within the thymidine kinase (TK) gene continue to function in a temporally regulated manner" (citations omitted)).

Thus, the nucleotide sequence(s) encoding the translation factor(s) can be under the control of a first type of promoter and the at least one nucleotide sequence of interest or the coding nucleotide sequence can be under the control of a second type of promoter, wherein the first and second promoters are both early, both late (including intermediate), or both early and late; or, the first promoter can be early or late and the second promoter early and late; or the first promoter can be early and late and the second promoter early or late. The nucleotide sequence of interest and the nucleotide sequence(s) encoding the translation factor(s) can be at the same locus or at different loci; or under the control of the same promoter.

Accordingly, the invention can relate to a method for preparing a vector having enhanced translation and/or expression, or to a method for increasing or enhancing translation and/or expression in a vector comprising operably linking to at least one nucleotide sequence of interest, or to a promoter operably linked thereto, at least one nucleotide sequence for at least one at least one translation factor. Preferably the translation factor effects an inhibition of eIF-2α phosphorylation and/or effects an inhibition of phosphorylation of PKR and/or a cellular kinase responsible for phosphorylation of eIF-2α and/or effects a decrease in the effective concentration of dsRNA. The invention also can thus relate to vectors from such methods.

Alternatively, the inventive methods can comprise operably linking at least one nucleotide sequence of interest to a first type of promoter and operably linking at least one second nucleotide sequence encoding at least one translation factor to a second type of promoter, within a vector, wherein the first and second promoters are both functional at the same time or same stage of infection, e.g., the first and second promoters are both early, both late (including intermediate), or both early and late; or, the first promoter is early or late and the second promoter is early and late; or the first promoter is early and late and the second promoter is early or late. Of course, the first and second promoters can be the same promoter at two or more different loci, or the same promoter at one locus. And, the invention thus relates to vectors from such methods.

And, the term "nucleotide sequence" as used herein can mean nucleic acid molecule. Thus, a nucleotide sequence can be an isolated nucleic acid molecule, e.g., exogenous DNA.

Accordingly, the present invention can provide vectors modified to contain at least one exogenous nucleotide sequence, preferably encoding at least one epitope of interest, and at least one translation factor, wherein there is substantially temporal co-expression (or substantially co-temporal expression or substantially contemporaneous expression) of the exogenous nucleotide sequence and the factor(s); and, methods for making and using such vectors and products therefrom. Enhanced or improved expression is obtained by the vectors and methods of the invention; and, enhanced or improved expression can mean enhanced levels and/or persistence of expression.

The invention can provide vectors, for instance, poxvirus vectors, e.g., NYVAC, ALVAC or TROVAC recombinants, having expression from the vaccinia E3L and/or K3L (or a homolog thereof, e.g., from another vector system, such as poxviruses other than vaccinia, herpesvirus, such as Epstein-Barr, adenovirus, plasmid or naked DNA, and the like, note discussion supra of viral mechanisms to overcome the cellular anti-viral response of translational down-regulation through PKR activation) as a means for enhancing and/or increasing the levels and persistence of an inserted nucleotide sequence, e.g., a foreign gene.

As shown in the Examples below, ALVAC-HIV recombinant vCP1452 containing the K3L/E3L factors had enhanced expression on human cells in comparison to vCP1433 or vCP300. Indeed, enhanced expression is observed with the E3L/K3L translational factors in human and canine cells.

Enhanced expression by translational factors such as E3L/K3L may be cell type dependent. For instance, while enhanced expression with E3L/K3L is observed in human and canine cells it is not observed in murine and feline cells. From this disclosure and the knowledge in the art, the skilled artisan can select an appropriate translational factor for use with a particular cell type, without undue experimentation. For example, it should go without saying that the skilled artisan knows the differences between cells. Thus it is preferred that the translational factor be expressed in a cell in which enhanced expression is observed, e.g., that the translational factor employed be with respect to the cell.

Further, preliminary immunogenicity studies in mice show no evidence of enhanced immunogenicity by the E3L/K3L translational factor. This corresponds to no observed enhanced expression in murine cells. Accordingly, the skilled artisan from this disclosure and the knowledge in the art can select a translational factor which will provide enhanced immunogenicity in a desired animal, without undue experimentation. If enhanced expression is observed in vitro in a particular cell line by a particular translational factor, e.g., E3L/K3L in human or canine cells, the skilled artisan can thus expect enhanced immunogenicity in vivo in the animal (including human) from which the cells were derived by that particular translational factor, e.g., enhanced immunogenicity in humans and canines from the E3L/K3L translational factor.

In an abortive early system such as ALVAC or NYVAC, one preferably expresses exogenous DNA and the translational factor(s) early; in an abortive late (including intermediate) system, one preferably expresses exogenous DNA and the translational factor late or early and late (as expression only early may not necessarily obtain optimal expression).

The selection of a suitable translation factor and time for its expression is within the ambit of the skilled artisan from this disclosure and knowledge in the art; for instance, the skilled artisan can select expression of a translation factor based on the nature of the vector and of the promoter to be used with the factor; for example based on an abortive phenotype of the vector, e.g., MVA is said to be abortive late, and late (including intermediate) or early or early/late expression from a translation factor may be employed with this vector; ALVAC is abortive early and early or early/late expression from a translation factor may be employed with this vector. The vector can also be a ts (temperature sensitive) mutant (with respect to early ($DNA^-$) and late defective mutants which can be also used in the practice of this invention, reference is made to Condit and Niles, supra).

Thus, the translation factor and the at least one nucleotide sequence of interest preferably are expressed early, late (including intermediate), or early/late, relative to the phenotype of the vector; and, preferably the translation factor should be selected such that it indeed enhances translation and/or expression with respect to the cell type the vector is being employed in.

The methods for making a vector or recombinant can be by or analogous to the methods disclosed in U.S. Pat. Nos. 4,603,112, 4,769,330, 5,174,993, 5,505,941, 5,338,683, 5,494,807, and 4,722,848, WO 95/30018, Paoletti, "Applications of pox virus vectors to vaccination: An update," PNAS U.S.A. 93:11349–11353, October 1996, Moss, "Genetically engineered poxviruses for recombinant gene expression, vaccination, and safety," PNAS U.S.A. 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS U.S.A. 93:11307–11312, October 1996, Andreansky et al., "The application of genetically engineered herpes simplex viruses to the treatment of experimental brain tumors," PNAS U.S.A. 93:11313–11318, October 1996, Robertson et al. "Epstein-Barr virus vectors for gene delivery to B lymphocytes," PNAS U.S.A. 93:11334–11340, October 1996, Frolov et al., "Alphavirus-based expression vectors: Strategies and applications," PNAS U.S.A. 93:11371–11377, October 1996, Kitson et al., J. Virol. 65, 3068–3075, 1991; U.S. Pat. Nos. 5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT W091/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS U.S.A. 93:11414–11420, October 1996, and U.S. Pat. Nos. 5,591,639, 5,589,466, and 5,580,859 relating to DNA expression vectors, inter alia. See also U.S. applications Ser. Nos. 08/675,566 and 08/675,556, relating to vectors, including adenovirus vectors.

As to the inserted nucleotide sequence in a vector of the invention, e.g., the foreign gene, the heterologous or exogenous nucleotide sequence, e.g., DNA, in vectors of the instant invention, preferably encodes an expression product comprising: an epitope of interest, a biological response modulator, a growth factor, a recognition sequence, a therapeutic gene or a fusion protein. With respect to these terms, reference is made to the following discussion, and generally to Kendrew, THE ENCYCLOPEDIA OF MOLECULAR BIOLOGY (Blackwell Science Ltd., 1995) and Sambrook, Fritsch and Maniatis, *Molecular Cloning, A Laboratory Manual,* 2nd Ed., Cold Spring Harbor Laboratory Press, 1982.

An epitope of interest is an immunologically relevant region of an antigen or immunogen or immunologically active fragment thereof, e.g., from a pathogen or toxin of veterinary or human interest.

An epitope of interest can be prepared from an antigen of a pathogen or toxin, or from another antigen or toxin which elicits a response with respect to the pathogen, or from another antigen or toxin which elicits a response with respect to the pathogen, such as, for instance: a Morbillivirus antigen, e.g., a canine distemper virus or measles or rinderpest antigen such as HA or F; a rabies glycoprotein, e.g., rabies glycoprotein G; an avian influenza antigen, e.g., turkey influenza HA, Chicken/Pennsylvania/1/83 influenza antigen such as a nudeoprotein (NP); a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; RAV-1 env; matrix and/or preplomer of infectious bronchitis virus; a Herpesvirus glycoprotein, e.g., a glycoprotein from feline herpesvirus, equine herpesvirus, bovine herpesvirus, pseudorabies virus, canine herpesvirus, HSV, Marek's Disease Virus, or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV); a parvovirus antigen, e.g., canine parvovirus; an equine influenza antigen; an poxvirus antigen, e.g., an ectromelia antigen, a canarypox virus antigen or a fowlpox virus antigen; or an infectious bursal disease virus antigen, e.g., VP2, VP3, VP4.

An epitope of interest can be from an antigen of a human pathogen or toxin, or from another antigen or toxin which elicits a response with respect to the pathogen, or from another antigen or toxin which elicits a response with respect to the pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a C. tetani antigen; a mumps antigen; a pneumococcal antigen, e.g., PspA; a Borrelia antigen, e.g., OspA, OspB, OspC of Borrelia associated with Lyme disease such as *Borrelia burgdorferi, Borrelia afzelli* and *Borrelia garinii*; a chicken pox (varicella zoster) antigen; or a Plasmodium antigen.

Of course, the foregoing lists are intended as exemplary, as the epitope of interest can be derived from any antigen of any veterinary or human pathogen; and, to obtain an epitope of interest, one can express an antigen of any veterinary or human pathogen (such that the invention encompasses the exogenous or foreign nucleotide sequence(s) of interest encoding at least one antigen).

Since the heterologous DNA can be a growth factor or therapeutic gene, the inventive recombinants can be used in gene therapy. Gene therapy involves transferring genetic information; and, with respect to gene therapy and immunotherapy, reference is made to U.S. Pat. No. 5,252,479, which is incorporated herein by reference, together with the documents cited in it and on its face, and to WO 94/16716 and U.S. Pat. No. 5,833,975 each of which is also incorporated herein by reference, together with the documents cited therein. The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention further relates to an immunogenic, immunological or vaccine composition containing the inventive vector and an acceptable carrier or diluent (e.g., veterinary acceptable or pharmaceutically acceptable). An immunological composition containing the vector (or an expression product thereof) elicits an immunological response—local or systemic. The response can, but need not be protective. An immunogenic composition containing the inventive recombinants (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method of inducing an immunological response in a host vertebrate comprising administering to the host an immunogenic, immunological or vaccine composition comprising the inventive recombinant virus or vector and an acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

For human administration, the inventive recombinants or vectors, can provide the advantage of expression without productive replication. This thus provides the ability to use recombinants of the invention in immunocompromised individuals; and, provides a level of safety to workers in contact with recombinants of the invention. Therefore, the invention comprehends methods for amplifying or expressing a protein by administering or inoculating a host with a recombinant virus or vector, whereby the host is not a natural host of the recombinant virus or vector, and there is expression without productive replication.

The exogenous or heterologous DNA (or DNA foreign to vaccine virus) can be DNA encoding any of the aforementioned epitopes of interest, as listed above. In this regard, with respect to Borrelia DNA, reference is made to U.S. Pat. No. 5,523,089, WO93/08306, PCT/US92/08697, Molecular Microbiology (1989), 3(4), 479–486, and PCT publications WO 93/04175, and WO 96/06165, incorporated herein by reference.

With respect to pneumococcal epitopes of interest, reference is made to Briles et al. WO 92/14488, incorporated herein by reference, with respect to tumor viruses reference is made to *Molecular Biology of Tumor Viruses, RNA TUMOR VIRUSES* (Second Edition, Edited by Weiss et al., Cold Spring Harbor Laboratory 1982) (e.g., page 44 et seq.—Taxonomy of Retroviruses), incorporated herein by reference.

With respect to DNA encoding epitopes of interest, attention is directed to documents cited herein, see, e.g., documents cited supra and documents cited infra, for instance: U.S. Pat. Nos. 5,174,993 and 5,505,941 (e.g., recombinant avipox virus, vaccinia virus; rabies glycoprotein (G), gene, turkey influenza hemagglutinin gene, gp51, 30 envelope gene of bovine leukemia virus, Newcastle Disease Virus (NDV) antigen, FelV envelope gene, RAV-1 env gene, NP (nudeoprotein gene of Chicken/Pennsylvania/1/83 influenza virus), matrix and preplomer gene of infectious bronchitis virus; HSV gD), U.S. Pat. No. 5,338,683 (e.g., recombinant vaccinia virus, avipox virus; DNA encoding Herpesvirus glycoproteins, inter alia), U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, C. tetani, avian influenza, mumps, NDV, inter alia), U.S. Pat. No. 5,503,834 (e.g., recombinant vaccinia, avipox, Morbillivirus, e.g., measles F, hemagglutinin, inter alia), U.S. Pat. No. 4,722,848 (e.g., recombinant vaccinia virus; HSV tk, HSV glycoproteins, e.g., gB, gD, influenza HA, Hepatitis B, e.g., HBsAg, inter alia), U.K. Patent GB 2 269 820 B and U.S. Pat. No. 5,514,375 (recombinant poxvirus; flavivirus structural proteins); WO 92/22641 and U.S. Pat. No. 5,863,542 and U.S. application Ser. No. 08/372,664 (e.g., recombinant poxvirus; immunodeficiency virus, HTLV, inter alia), WO 93/03145, and U.S. Pat. Nos. 5,658,572 and 5,641,490 (e.g., recombinant poxvirus; IBDV, inter alia), WO 94/16716 and U.S. Pat. No. 5,833,975 (e.g., recombinant poxvirus; cytokine and/or tumor associated antigens, inter alia), U.S. application Ser. No. 08/469,969 (rabies combination compositions), U.S. application Ser. No. 08/746,668 (lentivirus, retrovirus and/or immunodeficiency virus, including feline immunodeficiency virus, inter alia), U.S. Pat. No. 5,529,780 and allowed U.S. Pat. No. 5,688,920 (canine herpesvirus), U.S. application Ser. No. 08/471,025 (calicivirus), WO 96/3941 and U.S. application Ser. No. 08/658,665 (cytomegalovirus), and PCT/US94/06652 (Plasmodium antigens such as from each stage of the Plasmodium life cycle).

As to antigens for use in vaccine or immunological compositions, reference is made to the documents and discussion set forth in the documents cited herein (see, e.g., documents cited supra); see also Stedman's Medical Dictionary (24th edition, 1982, e.g., definition of vaccine (for a list of antigens used in vaccine formulations; such antigens or epitopes of interest from those antigens can be used in the invention, as either an expression product of an inventive recombinant virus or vector, or in a multivalent composition containing an inventive recombinant virus or vector or an expression product therefrom).

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology,* 1988.

As to size: the skilled artisan can maximize the size of the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD8+T cell response (which recognizes virus infected cells or cancerous cells). A minimum peptide length of 13 to 25 amino acids is useful to stimulate a CD4+T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less-effective for determining B-cell epitopes" since B cell epitopes are often not linear amino acid sequence but rather result from the tertiary structure of the folded three dimensional protein. Janis Kuby, *Immunology*, (1992) pp. 79–80.

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, (1992) p. 81

Yet another method for determining an epitope of interest is to perform an X-ray crystallographic analysis of the antigen (full length)-antibody complex. Janis Kuby, *Immunology*, (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a ‘different HLA type.’

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigen-presenting cells. T cells which have a protein called CD4 bind to the MHC class II/peptide complexes via the T cell receptor. This leads to the synthesis of specific cytokines which stimulate an immune response.

Some guidelines in determining whether a protein is an epitopes of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules*, Blood 85:2680–2684; Englehard, V. H., *Structure of Peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the “Relevant Literature” section of this patent, and column 13 of this patent which discloses that: “A large number of epitopes have been defined for a wide variety of organisms of interest. Of particular interest are those epitopes to which neutralizing antibodies are directed. Disclosures of such epitopes are in many of the references cited in the Relevant Literature section.”)

With respect to expression of a biological response modulator, reference is made to Wohlstadter, “Selection Methods,” WO 93/19170, published Sep. 30, 1993, and the documents cited therein, incorporated herein by reference.

For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invention can express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

Table 2 of Neidhardt et al *Physiology of the Bacterial Cell* (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells can be determined, without undue experimentation.

In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degraded by the cell by secretion of an enzyme for that degradation. Thus, production of the enzyme by a recombinant can regulate use or uptake of the molecule by a cell. Likewise, the recombinant can express a molecule which binds to the enzyme necessary for uptake or use of a molecule, thereby similarly regulating its uptake or use.

Localization targeting of proteins carried out through cleavage of signal peptides another type of modulation or regulation. In this case, a specific endoprotease catalytic activity can be expressed by the recombinant.

Other examples of mechanisms through which modulation of function may occur are RNA virus poly-proteins, allosteric effects, and general covalent and non-covalent steric hindrance. HIV is a well studied example of an RNA virus which expresses non-functional poly-protein constructs. In HIV "the gag, pol, and env poly-proteins are processed to yield, respectively, the viral structural proteins p17, p24, and p15—reverse transcriptase and integrase—and the two envelope proteins gp41 and gp120" (Kohl et al., PNAS U.S.A. 85:4686–90 (1988)). The proper cleavage of the poly-proteins is crucial for replication of the virus, and virions carrying inactive mutant HIV protease are non-infectious (Id.). This is another example of the fusion of proteins down-modulating their activity. Thus, it is possible to construct recombinant viruses which express molecules which interfere with endoproteases, or which provide endoproteases, for inhibiting or enhancing the natural expression of certain proteins (by interfering with or enhancing cleavage).

The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table 1 of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, *Proteases and Biological Control*, Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$–$10^6$ times lower than those of the corresponding enzyme" (See Table 3 of Reich, supra at page 54).

It is therefore possible to down-modulate the function of certain enzymes simply by the addition of a peptide sequence to one of its termini. For example, with knowledge of this property, a recombinant can express peptide sequences containing additional amino acids at one or both termini.

The formation or disassociation of multi-subunit enzymes is another way through which modulation may occur. Different mechanisms may be responsible for the modulation of activity upon formation or disassociation of multi-subunit enzymes.

Therefore, sterically hindering the proper specific subunit interactions will down-modulate the catalytic activity. And accordingly, the recombinant of the invention can express a molecule which sterically hinders a naturally occurring enzyme or enzyme complex, so as to modulate biological functions.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (Fritsch, *Enzyme Structure and Mechanism,* 2d ed; Freeman & Co. Publishers, 1984)). This type of modulation is possible by the recombinant expressing a suitable suicide substrate, to thereby modulate biological responses (e.g., by limiting enzyme activity).

There are also examples of non-covalent steric hindrance including many repressor molecules. The recombinant can express repressor molecules which are capable of sterically hindering and thus down-modulating the function of a DNA sequence by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules can be expressed which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art can ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which can modify or alter function, e.g., phosphorylation, is of importance.

From the foregoing, the skilled artisan can use the present invention to express a biological response modulator, without any undue experimentation.

With respect to expression of fusion proteins by inventive recombinants, reference is made to Sambrook, Fritsch, Maniatis, *Molecular Cloning, A LABORATORY MANUAL* (2d Edition, Cold Spring Harbor Laboratory Press, 1989) (especially Volume 3), and Kendrew, supra, incorporated herein by reference. The teachings of Sambrook et al., can be suitably modified, without undue experimentation, from this disclosure, for the skilled artisan to generate recombinants or vectors expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. Pat. No. 5,833,975 each of which is also incorporated herein by reference, together with the documents cited therein.

A growth factor can be defined as multifunctional, locally acting intercellular signalling peptides which control both ontogeny and maintenance of tissue and function (see Kendrew, supra, especially at page 455 et seq.).

The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 and allowed U.S. Pat. No. 5,833,975, provide genes for cytokines and tumor associated antigens and immunotherapy methods, including ex vivo methods, and the skilled artisan is directed to those disclosures.

Thus, one skilled in the art can create recombinants or vectors expressing a growth factor or therapeutic gene and use the recombinants or vectors, from this disclosure and the knowledge in the art, without undue experimentation.

Moreover, from the foregoing and the knowledge in the art, no undue experimentation is required for the skilled artisan to construct an inventive recombinant or vector which expresses an epitope of interest, a biological response modulator, a growth factor, a recognition sequence, a therapeutic gene, or a fusion protein; or for the skilled artisan to use such a recombinant or vector.

As the recombinants or vectors of the invention can be used for expression of gene products in vitro, techniques for protein purification can be employed in the practice of the invention, and such techniques, in general, include:

Briefly, the cells are disrupted and the protein of interest is released into an aqueous “extract”. There are many methods of cellular disintegration, which vary from relatively gentle to vigorous conditions, and the choice of one method over the other is dependent upon the source material. Animal tissues vary from the very easily broken erythrocytes to tough collagenous material such as found in blood vessels and other smooth-muscle containing tissue. Bacteria vary from fairly fragile organisms that can be broken up by digestive enzymes or osmotic shock to more resilient species with thick cell walls, needing vigorous mechanical treatment for disintegration.

Gentle techniques include cell lysis, enzymatic digestion, chemical solubilization, hand homogenization and mincing (or grinding); moderate techniques of cell disintegration include blade homogenization and grinding with abrasive materials, i.e., sand or alumina; and vigorous techniques include french press, ultrasonication, bead mill or Manton-Gaulin homogenization. Each of the aforementioned techniques are art-recognized, and it is well within the scope of knowledge of the skilled artisan to determine the appropriate method of cell disintegration based upon the starting material, and the teachings herein and in the art.

Following cell disintegration, the extract is prepared by centrifuging off insoluble material. At this stage, one may proceed with the purification method, as an extract containing as much of the protein of interest as possible has been prepared, and, where appropriate, particulate and most non-protein materials have been removed.

Standard techniques of protein purification may be employed to further purify the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immuno affinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the proteins or epitopes of interest from expression of a recombinant or vector of the invention, using the standard methodologies outlined hereinabove, and in the literature, as well as the teachings in the Examples below.

As the expression products can provide an antigenic, immunological, or protective (vaccine) response, the invention further relates to products therefrom; namely, antibodies and uses thereof. More in particular, the expression products can elicit antibodies by administration of those products or of recombinants or vectors expressing the products. The antibodies can be monoclonal antibodies; and, the antibodies or expression products can be used in kits, assays, tests, and the like involving binding, so that the invention relates to these uses too. Additionally, since the recombinants or vectors of the invention can be used to replicate DNA, the invention relates to the inventive recombinants as vectors and methods for replicating DNA by infecting or transfecting cells with the recombinant and harvesting DNA therefrom. The resultant DNA can be used as probes or primers or for amplification.

The administration procedure for the inventive recombinants or vectors or expression products thereof, compositions of the invention such as immunological, antigenic or vaccine compositions or therapeutic compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions can be prepared in accordance with standard techniques well known to those skilled in the pharmaceutical, medical or veterinary arts. Such compositions can be administered in dosages and by techniques well known to those skilled in the medical or veterinary arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from expression by an inventive recombinant or vector or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant or vector may be in admixture with a suitable carrier, diluent, or excipient such as sterile water, physiological saline, glucose or the like.

Antigenic, immunological or vaccine compositions typically can contain an adjuvant and an amount of the recombinant or vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if the recombinant is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 $\mu$g. The inventive recombinant or vector can be administered in any suitable amount to achieve expression at these dosage levels. The viral recombinants of the invention can be administered in an amount of about $10^{3.5}$ pfu; thus, the inventive viral recombinant is preferably administered in at least this amount; more preferably about $10^4$ pfu to about $10^6$ pfu; however higher dosages such as about $10^4$ pfu to about $10^{10}$ pfu, e.g., about $10^5$ pfu to about $10^9$ pfu, for instance about $10^6$ pfu to about $10^8$ pfu can be employed. Suitable quantities of inventive plasmid or naked DNA in plasmid or naked DNA compositions can be 1 ug to 100 mg, preferably 0.1 to 10 mg, but lower levels such as 0.1 to 2 mg or preferably 1–10 ug may be employed Other suitable carriers or diluents can be water or a buffered saline, with or without a preservative. The expression product or recombinant or vector may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. *Current Topics in Microbiology and Immunology* 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Furthermore, the inventive vectors or recombinants can be used in any desired immunization or administration regimen; e.g., as part of periodic vaccinations such as annual vaccinations as in the veterinary arts or as in periodic vaccinations as in the human medical arts, or as in a prime-boost regimen wherein an inventive vector or recombinant is administered either before or after the administration of the same or of a different epitope of interest or recombinant or vector expressing such a same or different epitope of interest (including an inventive recombinant or vector expressing such a same or different epitope of interest), see, e.g., documents cited herein such as U.S. application Ser. No. 08/746,668.

Additionally, the inventive vectors or recombinants and the expression products therefrom can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the antigen or, to determine whether an immune response to that agent or to the antigen (s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive recombinants or vectors or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

The recombinants or vectors of the invention are also useful for generating DNA for probes or for PCR primers which can be used to detect the presence or absence of hybridizable DNA or to amplify DNA, e.g., to detect a pathogen in a sample or for amplifying DNA.

Since viruses require translation of viral mRNAs in order to generate viral proteins required for replication, it is evident that any function which blocks the action of PKR in the infected cell will have a positive effect on viral protein expression. Thus, co-expression, in some fashion, of the vaccinia E3L/K3L gene products, or a homolog of E3L and/or K3L, may provide a general mechanism for enhancing the expression levels of heterologous gene products by vectors in general. The E3L/K3L or homologous functions may enhance or augment native anti-PKR mechanisms, and thus increase protein expression levels and/or persistence. This provides a useful element towards optimizing the efficiency of eukaryotic virus systems as immunization vehicles. This approach could be further extended for improvement of DNA-based immunogens, e.g., naked DNA or plasmid DNA vector systems. Thus, increased or enhanced levels or persistence of expression can be obtained.

A better understanding of the present invention and of its many advantages will be had from the following non-limiting Examples, given by way of illustration.

EXAMPLES

Example 1

ALVAC Recombinants pMPC6H6K3E3 (ATCC No. 97912) was used as a donor plasmid in in vivo recombination (Piccini et al., 1987) with rescuing virus vCP205 (ATCC No. VR-2557; U.S. application Ser. No. 08/417,210, incorporated herein by reference; HIV expression cassette—vaccinia H6 promoter/HIV truncated env MN strain, 13L gag with protease in ALVAC C3 insertion site); and the resulting recombinant virus was designated vCP1431A (vaccinia H6/K3L and E3L cassette in the C6 locus). With respect to the H6/K3L expression cassette and the vaccinia E3L gene with the endogenous promoter flanked by the ALVAC C6 insertion site sequences reference is made to FIG. 1 (SEQ ID NO:1).

pC3H6FHVB (ATCC No. 97914; FIG. 3, SEQ ID NO:3; H6 promoted FHV gB ORF with early transcriptional and translational stop signals at both 5' and 3' ends flanked by the left and right arms of the ALVAC C3 locus) was used in in vivo recombination with the ALVAC (ATCC No. VR-2547) to generate vCP1459 (H6 promoted FHV gB expression cassette in deorfed C3 insertion locus). With respect to the FHV-1 gB coding region in which the two internal $T_5NT$ motifs have been mutated, see FIG. 2 (SEQ ID NO:2).

pC3H6FHVB was used in in vivo recombination with vCP1431A to generate vCP1460 (H6 promoted FHV gB expression cassette in the deorfed C3 insertion locus and vaccinia E3L/K3L genes in C6 locus).

pMPC5H6PN (HIV pol/nef "string of beads" cassette in the ALVAC C5 locus) was used in recombination with vCP205 to obtain vCP1433 (ATCC Deposit No. VR-2556). Thus, recombinant ALVAC-MN120TMGNPst (vCP1433) was generated by insertion of an expression cassette encoding a synthetic polypeptide containing all of the known Pol CTL epitopes (Nixon and McMichael; 1991) and all of the known human Nef CTL epitopes into vCP205 at the insertion site known as C5.

pMPC6H6K3E3 (ATCC Deposit No. 97912; containing vaccinia H6/K3L expression cassette and vaccinia E3L gene with endogenous promoter flanked by the ALVAC C6 insertion site sequences) was used in recombination with vCP1433 to obtain vCP1452. FIGS. 4 and 5 show the nucleotide and amino acid sequences of the vCP1433 and vCP1452 inserts. FIG. 6 shows the K3L E3L in C6 in vCP1452. vCP1452 contains the HIV type 1 gag and protease genes derived from the IIIB isolate, the gp120 envelope sequences derived from the MN isolate, and sequences encoding a polypeptide encompassing the known human CTL epitopes from HIV-1 Nef and Pol (Nef1 and Nef2 CTL epitopes, and Pol1, Pol2 and Pol3 CTL epitopes). The expressed gp120 moiety is linked to the transmembrane (TM) anchor sequence (28 amino acids) of the envelope glycoprotein. In addition to the HIV coding sequences vCP1452 contains the vaccinia virus E3L and K3L coding sequences inserted into the C6 site. The insertion sites and promoter linkages for this construct are shown in the Table below.

TABLE

Insertion sites and promoter linkages in vCP1452

| Insert | Insertion Site | Promoter |
|---|---|---|
| HIV1 MN gp120 + TM | C3 | H6 |
| HIV1 IIIB gag (+ pro) | C3 | I3L |
| pol3/Nef C term/Pol2/Nef central/Pol1 | C5 | H6 |
| Vaccinia virus E3L | C6 | endogenous |
| Vaccinia virus K3L | C6 | H6 |

vCP300 is an ALVAC recombinant containing HIV gp120TM (MN), gag/pro (IIIB) (C3 locus), Nef (C6 locus), and Pol (C5 locus), as described in U.S. application Ser. No. 08/417,210, incorporated herein by reference.

Plasmids for preparing these recombinants were prepared as follows:

K3L Expression Cassette

The K3L coding sequences were synthesized by PCR amplification using pSD407VC containing Copenhagen vaccinia HindIII K fragment as template, as described in U.S. Pat. No. 5,378,457. The oligonucleotides MPSYN 763 and MPSYN 764 (SEQ ID NOS:8 and 9) were used as primers for the PCR reaction.

MPSYN 763 5'-CCCTCTAGATCGCGATATCCGTTAA-GTTTGTATCGTAATGCTTGCATTTTGTTATTCGT-3'

MPSYN 764 5'-CCCGAATTCATAAAAATTATTGA-TGTCTACA-3'

The approximately 325 bp PCR fragment was digested with XbaI and EcoRI yielding a 315 bp fragment. This 315 bp fragment was purified by isolation from an agarose gel and ligated with XbaI and EcoRI digested pBSSK+ vector (from Stratagene LA Jolla, Calif.). The nucleic acid sequence was confirmed directly from alkali denatured plasmid template as described in Hattori, M. and Sakaki, Y., 1986, using the modified T7 polymerase (Tabor, S. and Richardson, C. C. 1987) and Sequenase (from U.S. Biochemicals Cleveland, Ohio). This plasmid was designated pBS 763/764. Digesting pBS 763/764 with NruI and XhoI, a 340 bp fragment was isolated for cloning into the plasmid vector pMM154 containing a cassette with the vaccinia H6 promoter controlling an irrelevant gene in the NYVAC $tk^-$ insertion vector background, which was prepared by digestion with NruI (partially) and XhoI, such that the 340 bp fragment from pBS 763/764 containing the K3L gene could be directionally oriented next to the H6 promoter generating pMPTKH6K3L. The plasmid pMP42GPT containing the dominant selectable marker Eco gpt gene (Pratt D. and Subramani S. 1983) under the control of the Entomopox 42k promoter, was digested with SmaI and BamHI to yield a 0.7 Kbp 42k-Eco gpt expression cassette. This 0.7 Kbp fragment was purified and ligated into SmaI and BamHI cut pMPTKH6K3L generating the plasmid pMPTKH6K3Lgpt. This plasmid was digested with XhoI, generating a 1.2 Kbp fragment containing the H6/K3L and the 42k/Ecogpt expression cassette, which was then gel purified. The 1.2 Kbp XhoI fragment was inserted into the XhoI site of the ALVAC C6 insertion plasmid pC6L (described in U.S. Pat. No. 5,494, 807), generating pMPC6H6K3Lgpt.

E3L/K3L ALVAC Expression Cassette

The entire E3L gene is contained within a 2.3 Kbp EcoRI fragment isolated from pSD401VC, which contained a clone of the HindIII E fragment from Copenhagen vaccinia. The 2.3 Kbp EcoRI fragment was inserted into pMPC6H6K3Lgpt that had been partially digested with EcoRI, generating the plasmid pMPC6H6K3E3gpt. The plasmid pMPC6H6K3E3gpt was digested with XhoI and the resulting 6.8 Kbp vector fragment was purified and self-ligated, resulting in the plasmid pMPC6E3. The plasmid pMPTKH6K3L was digested with PspAI and the resulting 560 bp fragment containing the H6/K3L expression cassette was ligated into PspAI digested pMPC6E3 resulting in the plasmid construct pMPC6H6K3E3.

Construction of the H6-Promoted FHV gB Donor Plasmid

The entire coding region of the Feline Herpesvirus 1 glycoprotein gB (FHV-1 gB) was obtained by digestion of pJCA079 (FHV gB coding region in which 5' and 3' $T_5NT$ sequences were mutated to change the early transcriptional stop signal without affecting amino acid sequences; the I3L vaccinia promoter has been coupled to the 5' end of the gB ORF; see FIG. 4, SEQ ID NOS:4 and 5) with PstI and isolating a 3 Kbp fragment from an agarose gel. The purified PstI fragment was cloned into an ALVAC C3 insertion plasmid (pVQH6CP3LSA) also digested with PstI (the unique BamHI site in pVQH6CP3LSA was previously inactivated by digestion with BamHI, blunting the ends with Klenow polymerase and religation; pVQH6CP3LSA was obtained by digesting pVQH6CP3L, discussed in U.S. Pat. No. 5,494,807, with NotI and NsiI, from which a 6623 bp fragment was isolated and ligated to annealed oligonucleotides CP34 (5'GGCCGCGTCGACATGCA3') and CP35 (5'TGTCGACGC3') (SEQ ID NOS:10 and 11). The resulting plasmid, pRAC5, was screened for proper orientation of the gB coding region with respect to the H6 promoter. To properly link the H6 promoter to the FHV gB initiation codon, an 800 bp PCR fragment was amplified from pJCA079 using oligonucleotides RG789 (SEQ ID NO:12) (5'-TTTCATTATCGCGATATCCGTTAAGTTTGTATCG-TAATGTCCACTCGTGGCGATC-3') and RG787 (SEQ ID NO:13) (5'-GGAGGGTTTCAGAGGCAG-3'). This purified fragment was digested with NruI/BamHI and ligated into pRAC5 also digested with NruI/BamHI. The resulting plasmid was the FHV gB donor plasmid, pC3H6FHVB.

"String of Beads" Cassette

The "string of beads" expression cassette for the nef and pol CTL epitopes (H6/Pol 3/Nef C term/Pol 2/Nef central/Pol 1) was generated by PCR (polymerase chain reaction) as detailed below, using template pHXBD2 for pol epitopes and template 2–60-HIV.3 for Nef epitopes. Initial assembly was in two parts: (1) H6(partial promoter)/Pol 3/Nef C term(Nef 2); (2) Pol 2/Nef central (Nef 1)/Pol 1 in pBSSK. These were combined, then moved to pBSH6–11 for the assembly of the entire H6 promoter, then the H6/HIV cassette was moved to a C5 insertion plasmid.

(1) H6/Pol 3/Nef C term(Nef 2)

A 230 bp fragment (A) was derived by PCR to obtain the H6 linkage and Pol3 using synthetic oligonucleotides MPSYN783 and MPSYN784 and template pHXBD2. pHXBD2 was derived at the NIH/NCI (Dr. Nancy Miller) from a recombinant phage library of XbaI digested DNA from HTLV-III infected H9 cells cloned in lambda-J1 (Shaw et al., 1994). This plasmid contains the entire proviral DNA sequence of the HIV IIIB isolate.

A 110 bp fragment (B) was derived by PCR to obtain Nef2 using oligonucleotides MPSYN785/MPSYN786 and template p2-60-HIV.3 (described in U.S. Pat. No. 5,863,542).

PCR fragments A and B were combined in a PCR as template to obtain a 300 bp fragment containing H6 linkage/Pol3/Nef2 using external primers MPSYN783/MPSYN786 (SEQ ID NOS:14 and 17). The 300 bp fragment was digested with XhoI/HindIII and a 290 bp fragment was isolated and ligated with similarly digested PBSSK to generate pBS783/786. The sequence was confirmed.

(2)Pol 2/Nef central (Nef 1)/Pol 1

A 210 bp fragment (C) containing Pol2 was derived by PCR using synthetic oligonucleotides MPSYN787/MPSYN788 (SEQ ID NOS:18 and 19) and template pHXBD2.

A 270 bp fragment (D) containing Nef1 was derived by PCR using synthetic oligonucleotides MPSYN789/MPSYN790 (SEQ ID NOS:20 and 21) and template p2-60-HIV.3 (described in U.S. Pat. No. 5,863,542.

A 170 bp fragment (E) containing Poll was derived by PCR using primers MPSYN791/MPSYN792 (SEQ ID NOS:22 and 23) and template pHXBD2.

Fragments C and D were combined as template in a PCR for Pol 2/Nef 1 using external primers MPSYN787/MPSYN790 (SEQ ID NOS:18 and 21) resulting in a 460 bp PCR product (C+D).

Fragments D and E were combined as template in a PCR for Nef 1/Pol 1 using external primers MPSYN789/MPSYN792 (SEQ ID NOS:20 and 23), resulting in isolation of a 420 bp fragment (D+E).

Fragments (C+D) and (D+E) were combined as template in a PCR with external primers MPSYN787/MPSYN792 (SEQ ID NOS:18 and 23) to obtain a 610 bp fragment containing Pol 2/Nef 1 /Pol 1. This 610 bp fragment was digested with HindIII/PstI. The resulting 590 bp fragment was ligated with pBSSK cut with HindIII/PstI to generate pBS787/792. The sequence was confirmed.

MPSYN783: 5' CCC CTC GAG TCG CGA TAT CCG TTA AGT TTG TAT CGT AAT GCC ACT AAC AGA AGA AGC A 3'(58mer)

MPSYN784: 5' AAA TCT CCA CTC CAT CCT TGT TTT CAG ATT TTT AAA 3'(36 mer)

MPSYN785: 5' AAT CTG AAA ACA GGA ATG GAG TGG AGA TTT GAT TCT 3'(36 mer)

MPSYN786: 5° CCC AAG CTT ACA ATT TTT AAA ATA TTC AGG 3' (30 mer)

MPSYN787: 5° CCC AAG CTT ATG GCA ATA TTC CAA AGT AGC 3' (30 mer)
MPSYN788: 5' TGG AAA ACC TAC CAT GGT TGT AAG TCC CCA CCT CAA 3'(36 mer)
MPSYN789: 5' TGG GGA CTT ACA ACC ATG GTA GGT TTT CCA GTA ACA 3'(36 mer)
MPSYN790: 5' TAC AGT CTC AAT CAT TGG TAC TAG CTT GTA GCA CCA 3'(36 mer)
MPSYN791: 5' TAC AAG CTA GTA CCA ATG ATT GAG ACT GTA CCA GTA 3'(36 mer)
MPSYN792: 5° CCC CCT GCA GAA AAA TTA AGG CCC AAT TTT TGA AAT 3'(36 mer) (SEQ ID NOS:14–23)

Assembly of Entire Cassette

A 590 bp HindIII/PstI fragment was isolated from pBS787/792 and ligated with vector pBS783/786 cut with HindIII/PstI to generate pBS783/792. pBS783/792 was cut with EcoRV and PstI, to generate an 880 bp fragment which was then ligated with similarly digested vector pBSH6-1 to generate pBSH6PN. Plasmid pBSH6PN was digested with BamHI and a 1060 bp fragment was isolated. pVQC5LSP1, a generic C5 donor plasmid, was digested with BamHI and ligated with the 1060 bp fragment from pBSH6PN. The resulting plasmid, pMPC5H6PN, contains the HIV pol/nef "string of beads" cassette in the ALVAC C5 locus.

Example 2

Expression Studies

Dishes containing confluent monolayers of cells were infected at a multiplicity of infection (moi) of 2. After incubation for specified time periods, cells were incubated in labeling medium for 1 hour. At the end of the incubation, cells were harvested for immunoprecipitation analysis as described (Harlow, E. and Lane, D (1988); Langone, J. (1982)).

Cells were infected at an moi of 2 pfu/cell and incubated for specified time periods. At the appropriate time post-infection, cell lysates were prepared for RNA analysis. The medium was aspirated and cells were harvested. RNA was isolated and prepared using the TRI-Reagent (Molecular Research Center Inc. Cincinnati, Ohio 45212) as per manufacture instructions and analyzed by slot blot. Radiolabelled DNA probes were used to detect specific RNA species.

ALVAC-HIV Recombinants

Immunoprecipitation (IP) was used to provide a semi-quantitative comparison of the temporal expression of the HIV-I cassette contained in the ALVAC recombinants in MRC-5 infected cells. Heat inactivated sera from HIV patients was obtained and used for the IP as described in the methods. The antiserum will precipitate the 120 KDa env protein and the various cleavage products from the gag protein precursor. In the analysis of the IP data it is apparent that the ALVAC recombinants such as vCP1431A containing the E3L/K3L cassette had a significant increase in the level of expression at all times post infection when compared to the ALVAC recombinant vCP205 without the E3L/K3L cassette.

RNA slot blots were used to evaluate temporal transcriptional expression in MRC-5 cells infected with the ALVAC recombinants vCP205 and vCP1431A. In this analysis comparisons were made to the levels of mRNA transcribed from the HIV-I cassette encoding the env and gag proteins. ALVAC recombinants containing the E3L/K3L cassette (vCP1431A) did not exhibit a significant increase in the level of mRNA for the env and gag genes above that of the ALVAC recombinant vCP205.

The previously discussed role E3L/K3L plays in the down regulation of PKR in vaccinia infected cells thereby modulating translation seems to be operative in the ALVAC recombinants containing the vaccinia E3L/K3L functions. The data has shown that translation is significantly enhanced in cells infected with ALVAC recombinants containing the E3L/K3L genes, while no significant increase in the level of transcription has been detected. This exemplifies the impact of E3L/K3L expression on translation efficiency in poxvirus infected cells.

Immunoprecipitation analyses were also performed using radiolabeled lysates derived from CEF cells infected with ALVAC parental virus, ALVAC-MN120TMG (vCP205), ALVAC-MN120TMGNPst (vCP1433), vCP1452 and vCP300, as described previously (Taylor et al., 1990), with human serum derived from HIV-seropositive individuals (anti-HIV). The analysis confirmed the expression of the envelope sequences with a molecular weight of 120 kDa and the Gag precursor protein with a molecular weight of 55 kDa in the recombinants but not in the parental virus. However, vCP300 exhibits diminished expression in comparison to vCP1452, i.e., vCP1452 surprisingly demonstrates enhanced expression due to expression of transcription and/or translation factors, in accordance with the invention.

FAC scan analysis with the Human anti-HIV antibody demonstrated expression of gp120 on the surface of HeLa cells infected with ALVAC-MN120TMGNPst (vCP1433). No fluorescence was detected on cells infected with ALVAC parental virus.

Appropriate expression of the inserted HIV genes was further confirmed by immunoprecipitation analysis (using polyclonal serum pool from HIV infected individuals) performed on a radiolabelled lysate of MRC5 cells infected with vCP1433 or vCP1452. The analysis confirmed the expression of the envelope sequences with a molecular weight of 120 KDa and the Gag precursor protein with a molecular weight of 55 KDa in vCP1452.

vCP1452 had enhanced expression on human cells in comparison to vCP1433 and vCP300. Indeed, enhanced expression was observed with the E3L/K3L translational factors in human and canine cells.

Preliminary immunogenicity studies in mice showed no evidence of enhanced immunogenicity by the E3L/K3L translational factor. This corresponds to no observed enhanced expression in murine cells. Thus, the origin of the cell may be an important factor in in vitro or in vivo applications of the invention, as may be the nature of the vector, e.g., the phenotype of the vector (e.g., abortive, and when abortive such as abortive early, abortive late); but, appropriate selection of a cell and vector phenotype and of time of expression of factor(s) and foreign and/or exogenous DNA are within the ambit of the skilled artisan, from this disclosure and the knowledge in the art, without undue experimentation.

ALVAC-FHV gB Recombinants

Analysis of the expression for vCP1459 and vCP1460 was accomplished by immunoprecipitation analysis using a sheep anti-FHV gB polyclonal sera. Human MRC-5 cells were inoculated at an moi=5 at time 0, and then pulsed for 1 hour with $^{35}S$ labelled methionine at times 3, 6, 24, 48 and 72 h p.i. The precipitated protein was separated on SDS-PAGE gels. Autoradiographs of these IPs were scanned using a densitometer. The methods used provide a semi-quantitative analysis of FHV gB expression at the specific time points.

Results show that all recombinants express the proper sized full-length, glycosylated FHV gB polypeptide (apparent MW of approximately 115 kDa). However, recombinant vCP1460 shows significant increase in the amount of gB protein (about 5 times) compared to vCP1459.

In addition, these expression levels persist even at 72 hr p.i. Thus, it appears that the expression of vaccinia E3L/K3L in ALVAC has a significant effect on the level and persistence of FHV gB expression.

Example 3

Additional Vectors

Using the documents cited herein and the teaching herein, including in the foregoing Examples, plasmid and naked DNA vectors, and additional viral vectors, including poxvirus, e.g., NYVAC, TROVAC, ALVAC, MVA, ts (temperature sensitive) mutants, or early ($DNA^-$) and late defective mutants, adenovirus, e.g., CAV such as CAV2, herpesvirus, e.g., Epstein Barr, are generated with enhanced translation, e.g., by using E3L, K3L, VAI, EBER, sigma 3, TRBP, or combinations thereof, to modify the vector to contain at least one translation factor; and accordingly, enhanced expression, of exogenous coding nucleic acid molecules (such exogenous coding nucleic acid molecules including from documents cited herein or as otherwise known in the art, or from applying those teachings in conjunction with teachings herein) is obtained.

Having thus described in detail preferred embodiments of the present invention, it is to be understood that the invention defined by the appended claims is not to be limited to particular details set forth in the above description as many apparent variations thereof are possible without departing from the spirit or scope of the present invention.

REFERENCES

Ahn, B-Y. and Moss, B. 1992. RNA polymerase-associated transcription specificity factor encoded by vaccinia virus. Proc. Natl. Acad. Sci. 89: 3536–3540.

Beattie, E., Denzler, K., Tartaglia, J., Paoletti, E. and Jacobs, B. L. 1995. Reversal of the interferon-sensitive phenotype of and E3L-minus vaccinia virus by expression of the reovirus S4 gene. J. Virol. 69: 499–505 ("Beattie et al. 1995a").

Beattie, E., Paoletti, E., and Tartaglia, J. 1995. Distinct Patterns of IFN Sensitivity Observed in Cells Infected with Vaccinia $K3L^-$ and $E3L^-$ Mutant Viruses. Virology 210:254–263 ("Beattie et al 1995b")

Beattie, E., Tartaglia, J. and Paoletti, E. 1991. Vaccinia virus-encoded eIF-2α homologue abrogates the antiviral effect of interferon. Virology 183: 419–422.

Carroll, K., Elroy Stein, O., Moss, B. and Jagus, R. 1993. Recombinant vaccinia virus K3L gene product prevents activation of double-stranded RNA-dependent, initiation factor 2 alpha-specific protein kinase. J. Biol. Chem. 268: 12837–12842.

Chang, H-W., Watson, J. and Jacobs, B. L. 1992. The vaccinia virus E3L gene encodes a double-stranded RNA-binding protein with inhibitory activity for the interferon-induced protein kinase. Proc. Natl. Acad. Sci. USA 89: 4825–4829.

Clark, P. A., Schwemmle, M., Schickinger, J., Hilse, K., and Clemens, M. J. 1991. Binding of Epstein-Barr virus small RNA EBER-1 to double-stranded RNA-activated protein kinase DAI. Nucleic Acids Res. 19:243–248.

Davies, M. V., Chang, H. W., Jacobs, B. L. and Kaufman, R. J. 1993. The E3L and K3L vaccinia virus gene products stimulate translation through inhibition of the double-stranded RNA-dependent protein kinase by different mechanisms. J. Virol. 67: 1688–1692.

Davies, M. V., Elroy Stein, O., Jagus, R., Moss, B. and Kaufman, R. J. 1992. The vaccinia K3L gene product potentiates translation by inhibiting double-stranded-RNA-activated protein kinase and phosphorylation of the alpha subunit of eukaryotic initiation factor 2. J. Virol. 66: 1943–1950.

Goebel, S. J., Johnson, G. P., Perkus, M. E., Davis, S. W., Winslow, J. P. and Paoletti, E. 1990. The complete DNA sequence of vaccinia virus. Virology 179: 247–266.

Harlow, E. and Lane, D. (1988). Antibodies, A Laboratory Manual. Cold Spring Harbor Laboratory. 421–470.

Hattori, M., and Sakaki, Y. (1986). Dideoxy sequencing method using denatured plasmid templates. Anal. Biochem. 152, 232–237.

Imani, F. and Jacobs, B. L. 1988. Inhibitory activity for the interferon induced protein kinase is associated with the reovirus serotype 1 s3 protein. Proc. Natl. Acad. Sci. U.S.A. 85: 7887–7891.

Jacobs, B. L. and Langland, J. 0. 1996. When two strands are better than one: the mediators and modulators of the cellular responses to double-stranded RNA. Virology 219: 339–349.

Langone, J. (1982). Applications of immobilized protein A in immunochemical techniques. J. Immunol. Methods. 55. 277–296.

Mathews, M. B. and Shenk, T. 1991. Adenovirus virus-associated RNA and translation control. J. Virol. 65: 5657–5662.

Moss, B. 1990. Regulation of vaccinia virus transcription. Annu. Rev. Biochem. 59: 661–688.

Moss, B. 1992. Molecular biology of poxviruses. In *Recombinant Poxviruses*. Binns M. M., Smith, G. L. (eds). Boca Raton, Fla.: CRC Press; pg. 45–80.

Park, H., Davies, M. V., Langland, L. O., Chang, H-W., Nam, Y. S., Tartaglia, J., Paoletti, E., Jacobs, B. L., Kaufman, R. J. and Venkatesan, S. 1994. A cellular protein that binds several structured viral RNAs is an inhibitor of the interferon induced PKR protein kinase in vitro and in vivo. Proc. Natl. Acad. Sci. U.S.A. 91: 4713–4717.

Perkus, M., Limbach, K., Paoletti, E. (1989). Cloning and expression of foreign genes in vaccinia virus, using a host range selection system. J. Virology 63. 3829–3836.

Perkus, M. E., Tartaglia, J., and Paoletti, E. 1995. Poxvirus-based vaccine candidates for cancer, AIDS and other infectious diseases. J. of Leukocyte Biology 58: 1–13.

Sharp, T. V., Schwemmle, M., Jeffrey, I., Laing, K., Mellor, H., Proud, C. G., Hilse, K. and Clemens, M. J. 1993. Comparative analysis of the regulation of the interferon-inducible protein kinase PKR by Epstein-Barr virus RNAs EBER-1 and EBER-2 and adenovirus VAI RNA. Nucleic Acids Res. 21: 4483–4490.

Tabor, S., and Richardson, C. C. (1987). DNA sequence analysis with a modified bacteriophage T7 polymerase. Proc. Natl. Acad. Sci. USA 84, 4767–4771.

Tartaglia, J., Perkus, M. E., Taylor, J. et al. 1992. NYVAC: A highly attenuated strain of vaccinia virus. Virology 188: 217–32.

Thimmappaya, B. C., Weinberger, C., Schneider, R. J. and Shenk, T. 1982. Adenovirus VAI RNA is required for efficient translation of viral mRNAs at late times after infection. Cell 31: 543–551.

Watson, J., Chang, H-W. and Jacobs, B. L. 1991. Characterization of a vaccinia virus-induced dsRNA-binding protein that may be the inhibitor of the dsRNA-dependent protein kinase. Virology 185: 206–216.

Yuen, L, and Moss, B. (1987). Oligonucleotide sequence signaling transcriptional termination of vaccinia virus early genes. Proc. Natl. Acad. Sci. USA 84, 6417–6421.

Zhang, Y., Ahn, B-Y. and Moss, B. 1994. Targeting of a multicomponent transcription apparatus into assembling vaccinia virus particles requires RAP94, an RNA polymerase-associated protein. J. Virol. 68: 1360–1370.

What is claimed is:

1. A vector for enhanced expression of at least one first nucleic acid molecule in a cell, said vector modified to comprise nucleic acid sequences comprising the first nucleic acid molecule and at least one second nucleic acid molecule encoding a translation factor, wherein the vector is modified to comprise the nucleic acid sequences by at least one insertion into the vector, and there is substantially co-temporal expression of the first and second nucleic acid molecules, whereby expression of the second nucleic acid molecule enhances expression of the first nucleic acid molecule by enhancing translation, wherein the insertion is not present in the vector prior to the modification.

2. The vector of claim 1 wherein the first nucleic acid molecule is operably linked to a first promoter and the second nucleic acid molecule is operably linked to a second promoter, and the first and second promoters are functional substantially co-temporally.

3. The vector of claim 2 wherein the first and second nucleic acid molecules are at different loci within the vector.

4. The vector of claim 2 wherein the first and second nucleic acid molecules are at the same locus within the vector.

5. The vector of claim 1 wherein the first nucleic acid molecule and the second nucleic acid molecule are operably linked to a promoter.

6. The vector of claim 1 wherein the translation factor effects inhibition of eIF-2α phosphorylation or inhibition of PKR phosphorylation or sequesters dsRNA.

7. The vector of claim 6 wherein said at least one second molecule is selected from the group consisting of: a K3L open reading frame, an E3L open reading frame, a VAI RNA, an EBER RNA, a sigma 3 open reading frame, a TRBP open reading frame, and combinations thereof.

8. The vector of claim 1 wherein said first nucleic acid molecule is selected from the group consisting of nucleic acid molecules encoding: an epitope of interest, a biological response modulator, a growth factor, a recognition sequence, a therapeutic gene, and a fusion protein.

9. The vector of claim 1 which is a recombinant virus.

10. The vector of claim 9 which is a recombinant poxvirus.

11. A method for preparing a vector as claimed in claim 1 comprising modifying the vector to comprise the at least one second nucleic acid molecule, and optionally also modifying the vector to comprise the first nucleic acid molecule, so that there is substantially co-temporal expression of the first and second nucleic acid molecules.

12. The method of claim 11 comprising operably linking the first nucleic acid molecule to a first promoter and the second nucleic acid molecule to a second promoter, wherein the first and second promoters are functional substantially co-temporally.

13. The method of claim 11 comprising operably linking the first and second nucleic acid molecules to a promoter.

14. A method of expressing a gene product in vitro comprising infecting, or transfecting, a suitable cell with a vector as claimed in claim 1.

15. A method of increasing expression of at least one first nucleic acid molecule by a vector comprising the first nucleic acid molecule, in a cell, comprising modifying the vector to comprise at least one second nucleic acid molecule encoding a translation factor, and expressing the vector in the cell; wherein there is substantially co-temporal expression of the first and second nucleic acid molecules, whereby expression of the second nucleic acid molecule enhances expression of the first nucleic acid molecule by enhancing translation.

* * * * *

SEQUENCE LISTING

<160> NUMBER OF SEQ ID NOS: 23

<210> SEQ ID NO 1
<211> LENGTH: 4434
<212> TYPE: DNA
<213> ORGANISM: Vaccinia virus

<400> SEQUENCE: 1
gagctcgcgg ccgcctatca aaagtcttaa tgagttaggt gtagatagta tagatattac 60
tacaaaggta ttcatatttc ctatcaattc taaagtagat gatattaata actcaaagat 120
gatgatagta gataatagat acgctcatat aatgactgca aatttggacg gttcacattt 180
taatcatcac gcgttcataa gtttcaactg catagatcaa aatctcacta aaaagatagc 240
cgatgtattt gagagagatt ggacatctaa ctacgctaaa gaaattacag ttataaataa 300
tacataatgg attttgttat catcagttat atttaacata agtacaataa aaagtattaa 360
ataaaaatac ttacttacga aaaaatgact aattagctat aaaaacccag atctctcgag 420
gtcgacggta tcgataagct tgatatcgaa ttcataaaaa ttattgatgt ctacacatcc 480
ttttgtaatt gacatctata tatccttttg tataatcaac tctaatcact ttaactttta 540
cagttttccc taccagttta tccctatatt caacatatct atccatatgc atcttaacac 600
tctctgccaa gatagcttca gagtgaggat agtcaaaaag ataaatgtat agagcataat 660
ccttctcgta tactctgccc tttattacat cgcccgcatt gggcaacgaa taacaaaatg 720
caagcatacg atacaaactt aacggatatc gcgataatga aataatttat gattatttct 780
cgctttcaat ttaacacaac cctcaagaac ctttgtattt attttcactt tttaagtata 840
gaataaagaa agctctaatt aattaatgaa cagattgttt cgttttcccc ttggcgtatc 900
actaattaat taacccgggc tgcagctcga ggaattcaac tatatcgaca tatttcattt 960
gtatacacat aaccattact aacgtagaat gtataggaag agatgtaacg ggaacagggt 1020
ttgttgattc gcaaactatt ctaatacata attcttctgt taatacgtct tgcacgtaat 1080
ctattataga tgccaagata tctatataat tattttgtaa gatgatgtta actatgtgat 1140
ctatataagt agtgtaataa ttcatgtatt tcgatatatg ttccaactct gtctttgtga 1200
tgtctagttt cgtaatatct atagcatcct caaaaaatat attcgcatat attcccaagt 1260
cttcagttct atcttctaaa aaatcttcaa cgtatggaat ataataatct attttacctc 1320
ttctgatatc attaatgata tagtttttga cactatcttc tgtcaattga ttcttattca 1380
ctatatctaa gaaacggata gcgtccctag gacgaactac tgccattaat atctctatta 1440
tagcttctgg acataattca tctattatac cagaattaat gggaactatt ccgtatctat 1500
ctaacatagt tttaagaaag tcagaatcta agacctgatg ttcatatatt ggttcataca 1560
tgaaatgatc tctattgatg atagtgacta tttcattctc tgaaaattgg taactcattc 1620
tatatatgct ttccttgttg atgaaggata gaatatactc aatagaattt gtaccaacaa 1680
actgttctct tatgaatcgt atatcatcat ctgaaataat catgtaaggc atacatttaa 1740
caattagaga cttgtctcct gttatcaata tactattctt gtgataattt atgtgtgagg 1800
caaatttgtc cacgttcttt aattttgtta tagtagatat caaatccaat ggagctacag 1860
ttcttggctt aaacagatat agtttttctg gaacaaattc tacaacatta ttataaagga 1920
ctttgggtag ataagtggga tgaaatccta ttttaattaa tgctatcgca ttgtcctcgt 1980
gcaaatatcc aaacgctttt gtgatagtat ggcattcatt gtctagaaac gctctacgaa 2040

-continued

```
tatctgtgac agatatcatc tttagagaat atactagtcg cgttaatagt actacaattt   2100

gtattttta atctatctca ataaaaaaat taatatgtat gattcaatgt ataactaaac   2160

tactaactgt tattgataac tagaatcaga atctaatgat gacgtaacca agaagtttat   2220

ctactgccaa tttagctgca ttatttttag catctcgttt agattttcca tctgccttat   2280

cgaatactct tccgtcgatg tctacacagg cataaaatgt aggagagtta ctaggcccaa   2340

ctgattcaat acgaaaagac caatctctct tagttatttg gcagtactca ttaataatgg   2400

tgacagggtt agcatctttc caatcaataa tttttttagc cggaataaca tcatcaaaag   2460

acttatgatc ctctctcatt gatttttcgc gggatacatc atctattatg acgtcagcca   2520

tagcatcagc atccggctta tccgcctccg ttgtcataaa ccaacgagga ggaatatcgt   2580

cggagctgta caccatagca ctacgttgaa gatcgtacag agctttatta acttctcgct   2640

tctccatatt aagttgtcta gttagttgtg cagcagtagc tccttcgatt ccaatgtttt   2700

taatagccgc acacacaatc tctgcgtcag aacgctcgtc aatatagatc ttagacattt   2760

ttagagagaa ctaacacaac cagcaataaa actgaaccta ctttatcatt tttttattca   2820

tcatcctctg gtggttcgtc gtttctatcg aatgtagctc tgattaaccc gtcatctata   2880

ggtgatgctg gttctggaga ttctggagga gatggattat tatctggaag aatctctgtt   2940

atttccttgt tttcatgtat cgattgcgtt gtaacattaa gattgcgaaa tgctctaaat   3000

ttgggaggct taaagtgttg tttgcaatct ctacacgcgt gtctaactag tggaggttcg   3060

tcagctgctc tagtttgaat catcatcggc gtagtattcc tacttttaca gttaggacac   3120

ggtgtattgt atttctcgtc gagaacgtta aaataatcgt tgtaactcac atcctttatt   3180

ttatctatat tgtattctac tcctttctta atgcatttta taccgaataa gagatagcga   3240

aggaattctt tttattgatt aactagtcaa atgagtatat ataattgaaa aagtaaaata   3300

taaatcatat aataatgaaa cgaaatatca gtaatagaca ggaactggca gattcttctt   3360

ctaatgaagt aagtactgct aaatctccaa aattagataa aaatgataca gcaaatacag   3420

cttcattcaa cgaattacct tttaattttt tcagacacac cttattacaa actaactaag   3480

tcagatgatg agaaagtaaa tataaattta acttatgggt ataatataat aaagattcat   3540

gatattaata atttacttaa cgatgttaat agacttattc catcaacccc ttcaaacctt   3600

tctggatatt ataaaatacc agttaatgat attaaaatag attgtttaag agatgtaaat   3660

aattatttgg aggtaaagga tataaaatta gtctatcttt cacatggaaa tgaattacct   3720

aatattaata attatgatag gaatttttta ggatttacag ctgttatatg tatcaacaat   3780

acaggcagat ctatggttat ggtaaaacac tgtaacggga agcagcattc tatggtaact   3840

ggcctatgtt taatagccag atcattttac tctataaaca ttttaccaca aataatagga   3900

tcctctagat atttaatatt atatctaaca acaacaaaaa aatttaacga tgtatggcca   3960

gaagtatttt ctactaataa agataaagat agtctatctt atctacaaga tatgaaagaa   4020

gataatcatt tagtagtagc tactaatatg gaaagaaatg tatacaaaaa cgtggaagct   4080

tttatattaa atagcatatt actagaagat ttaaaatcta gacttagtat aacaaaacag   4140

ttaaatgcca atatcgattc tatatttcat cataacagta gtacattaat cagtgatata   4200

ctgaaacgat ctacagactc aactatgcaa ggaataagca atatgccaat tatgtctaat   4260

attttaactt tagaactaaa acgttctacc aatactaaaa ataggatacg tgataggctg   4320

ttaaaagctg caataaatag taaggatgta gaagaaatac tttgttctat accttcggag   4380

gaaagaactt tagaacaact taagtttaat caaacttgta tttatgaagg tacc          4434
```

<210> SEQ ID NO 2
<211> LENGTH: 2844
<212> TYPE: DNA
<213> ORGANISM: Vaccinia virus

<400> SEQUENCE: 2

```
atgtccactc gtggcgatct tgggaagcgg cgacgaggga gtcgttggca gggacacagt     60
ggctattttc gacagagatg ttttttccct tctctactcg gtattgcagc gactggctcc    120
agacatggta acggatcgtc gggattaacc agactagcta gatatgtttc atttatctgg    180
atcgtactat tcttagtcgg tccccgtcca gtagagggtc aatctggaag cacatcggaa    240
caaccccggc ggactgtagc taccccctgag gtagggggta caccaccaaa accaactaca    300
gatcccaccg atatgtcgga tatgagggaa gctctccgtg cgtcccaaat agaggctaac    360
ggaccatcga ctttctatat gtgtccacca ccttcaggat ctactgtcgt gcgtttagag    420
ccaccacggg cctgtccaga ttataaacta gggaaaaatt ttaccgaggg tatagctgta    480
atatttaaag aaaatatagc gccatataaa ttcaaggcaa atatatacta taaaaacatt    540
attatgacaa cggtatggtc tgggagttcc tatgccgtta caaccaaccg atatacagac    600
agggttcccg tgaaagttca agagattaca gatctcatag atagacgggg tatgtgcctc    660
tcgaaagctg attacgttcg taacaattat caatttacgg cctttgatcg agacgaggat    720
cccagagaac tgcctctgaa accctccaag ttcaacactc cagagtcccg tggatggcac    780
accaccaatg aaacatacac aaagatcggt gctgctggat ttcaccactc tgggacctct    840
gtaaattgca tcgtagagga agtggatgca agatctgtat atccatatga ctcatttgct    900
atctccactg gtgacgtgat tcacatgtct ccattctttg ggctgaggga tggagcccat    960
gtagaacata ctagttattc ttcagacaga tttcaacaaa tcgagggata ctatccaata   1020
gacttggata cgcgattaca actgggggca ccagtttctc gcaatttttt ggaaactccg   1080
catgtgacag tggcctggaa ctggacccca aagtctggtc gggtatgtac cttagccaaa   1140
tggagggaaa tagatgaaat gctacgcgat gaatatcagg gctcctatag atttacagcc   1200
aagaccatat ccgctacttt catctccaat acttcacaat ttgaaatcaa tcgtatccgt   1260
ttgggggact gtgccaccaa ggaggcagcc gaagccatag accggattta taagagtaaa   1320
tatagtaaaa ctcatattca gactggaacc ctggagacct acctagcccg tgggggattt   1380
ctaatagctt tccgtcccat gatcagcaac gaactagcaa agttatatat caatgaatta   1440
gcacgttcca atcgcacggt agatctcagt gcactcctca atccatctgg ggaaacagta   1500
caacgaacta gaagatcggt cccatctaat caacatcata ggtcgcggcg cagcacaata   1560
gagggggggta tagaaaccgt gaacaatgca tcactcctca agaccacctc atctgtggaa   1620
ttcgcaatgc tacaatttgc ctatgactac atacaagccc atgtaaatga aatgttgagt   1680
cggatagcca ctgcctggtg tacacttcag aaccgcgaac atgtgctgtg gacagagacc   1740
ctaaaactca atcccggtgg ggtggtctcg atggccctag aacgtcgtgt atccgcgcgc   1800
ctacttggag atgccgtcgc cgtaacacaa tgtgttaaca tttctagcgg acatgtctat   1860
atccaaaatt ctatgcgggt gacgggttca tcaacgacat gttacagccg ccctcttgtt   1920
tccttccgtg ccctcaatga ctccgaatac atagaaggac aactagggga aaacaatgaa   1980
cttctcgtgg aacgaaaact aattgagcct tgcactgtca ataataagcg gtattttaag   2040
tttggggcag attatgtata ttttgaggat tatgcgtatg tccgtaaagt cccgctatcg   2100
gagatagaac tgataagtgc gtatgtgaat ttaaatctta ctctcctaga ggatcgtgaa   2160
```

```
tttctcccac tcgaagttta tacacgagct gagctggaag ataccggcct tttggactac   2220
agcgagattc aacgccgcaa ccaactccac gccttaaaat tttatgatat agacagcata   2280
gtcagagtgg ataataatct tgtcatcatg cgtggtatgg caaatttctt tcagggactc   2340
ggggatgtgg gggctggttt cggcaaggtg gtcttagggg ctgcgagtgc ggtaatctca   2400
acagtatcag gcgtatcatc atttctaaac aacccatttg gagcattggc cgtgggactg   2460
ttaatattag ctggcatcgt cgcagcattc ctggcatatc gctatatatc tagattacgt   2520
gcaaatccaa tgaaagcctt atatcctgtg acgactagga atttgaaaca gacgctaaga   2580
gcccgctcaa cggctggtgg ggatagcgac ccgggagtcg atgacttcga tgaggaaaag   2640
ctaatgcagg caagggagat gataaaatat atgtccctcg tatcggctat ggagcaacaa   2700
gaacataagg cgatgaaaaa gaataagggc ccagcgatcc taacgagtca tctcactaac   2760
atggccctcc gtcgccgtgg acctaaatac caacgcctca ataatcttga tagcggtgat   2820
gatactgaaa caaatcttgt ctaa                                          2844
```

<210> SEQ ID NO 3
<211> LENGTH: 6628
<212> TYPE: DNA
<213> ORGANISM: Vaccinia virus

<400> SEQUENCE: 3

```
gcggccgcgt cgacatgcat tgttagttct gtagatcagt aacgtatagc atacgagtat     60
aattatcgta ggtagtaggt atcctaaaat aaatctgata cagataataa ctttgtaaat    120
caattcagca atttctctat tatcatgata atgattaata cacagcgtgt cgttattttt    180
tgttacgata gtatttctaa agtaaagagc aggaatccct agtataatag aaataatcca    240
tatgaaaaat atagtaatgt acatatttct aatgttaaca tatttatagg taaatccagg    300
aagggtaatt tttacatatc tatatacgct tattacagtt attaaaaata tacttgcaaa    360
catgttagaa gtaaaaaaga aagaactaat tttacaaagt gctttaccaa aatgccaatg    420
gaaattactt agtatgtata taatgtataa aggtatgaat atcacaaaca gcaaatcggc    480
tattcccaag ttgagaaacg gtataataga tatatttcta gataccatta ataaccttat    540
aagcttgacg tttcctataa tgcctactaa gaaaactaga agatacatac atactaacgc    600
catacgagag taactactca tcgtataact actgttgcta acagtgacac tgatgttata    660
actcatcttt gatgtggtat aaatgtataa taactatatt acactggtat tttatttcag    720
ttatatacta tatagtatta aaaattatat ttgtataatt atattattat attcagtgta    780
gaaagtaaaa tactataaat atgtatctct tatttataac ttattagtaa agtatgtact    840
attcagttat attgttttat aaaagctaaa tgctactaga ttgatataaa tgaatatgta    900
ataaattagt aatgtagtat actaatatta actcacattt gactaattag ctataaaaac    960
ccgggctgca gcccgggaag cttacaaaaa ttagacaaga tttgtttcag tatcatcacc   1020
gctatcaaga ttattgaggc gttggtattt aggtccacgg cgacggaggg ccatgttagt   1080
gagatgactc gttaggatcg ctgggccctt attctttttc atcgccttat gttcttgttg   1140
ctccatagcc gatacgaggg acatatattt tatcatctcc cttgcctgca ttagcttttc   1200
ctcatcgaag tcatcgactc ccgggtcgct atccccacca gccgttgagc gggctcttag   1260
cgtctgtttc aaattcctag tcgtcacagg atataaggct ttcattggat ttgcacgtaa   1320
tctagatata tagcgatatg ccaggaatgc tgcgacgatg ccagctaata ttaacagtcc   1380
cacggccaat gctccaaatg ggttgtttag aaatgatgat acgcctgata ctgttgagat   1440
```

-continued

```
taccgcactc gcagccccta agaccacctt gccgaaacca gcccccacat ccccgagtcc   1500
ctgaaagaaa tttgccatac cacgcatgat gacaagatta ttatccactc tgactatgct   1560
gtctatatca taaaatttta aggcgtggag ttggttgcgg cgttgaatct cgctgtagtc   1620
caaaaggccg gtatcttcca gctcagctcg tgtataaact tcgagtggga gaaattcacg   1680
atcctctagg agagtaagat ttaaattcac atacgcactt atcagttcta tctccgatag   1740
cgggacttta cggacatacg cataatcctc aaaatataca taatctgccc caaacttaaa   1800
ataccgctta ttattgacag tgcaaggctc aattagtttt cgttccacga gaagttcatt   1860
gttttcccct agttgtcctt ctatgtattc ggagtcattg agggcacgga aggaaacaag   1920
agggcggctg taacatgtcg ttgatgaacc cgtcacccgc atagaatttt ggatatagac   1980
atgtccgcta gaaatgttaa cacattgtgt tacggcgacg gcatctccaa gtaggcgcgc   2040
ggatacacga cgttctaggg ccatcgagac caccccaccg ggattgagtt ttagggtctc   2100
tgtccacagc acatgttcgc ggttctgaag tgtacaccag gcagtggcta tccgactcaa   2160
catttcattt acatgggctt gtatgtagtc ataggcaaat tgtagcattg cgaattccac   2220
agatgaggtg gtcttgagga gtgatgcatt gttcacggtt tctatacccc cctctattgt   2280
gctgcgccgc gacctatgat gttgattaga tgggaccgat cttctagttc gttgtactgt   2340
ttccccagat ggattgagga gtgcactgag atctaccgtg cgattggaac gtgctaattc   2400
attgatatat aactttgcta gttcgttgct gatcatggga cggaaagcta ttagaaatcc   2460
cccacgggct aggtaggtct ccagggttcc agtctgaata tgagttttac tatatttact   2520
cttataaatc cggtctatgg cttcggctgc ctccttggtg gcacagtccc ccaaacggat   2580
acgattgatt tcaaattgtg aagtattgga gatgaaagta gcggatatgg tcttggctgt   2640
aaatctatag gagccctgat attcatcgcg tagcatttca tctatttccc tccatttggc   2700
taaggtacat acccgaccag actttggggt ccagttccag gccactgtca catgcggagt   2760
ttccaaaaaa ttgcgagaaa ctggtgcccc cagttgtaat cgcgtatcca agtctattgg   2820
atagtatccc tcgatttgtt gaaatctgtc tgaagaataa ctagtatgtt ctacatgggc   2880
tccatccctc agcccaaaga atggagacat gtgaatcacg tcaccagtgg agatagcaaa   2940
tgagtcatat ggatatacag atcttgcatc cacttcctct acgatgcaat ttacagaggt   3000
cccagagtgg tgaaatccag cagcaccgat ctttgtgtat gtttcattgg tggtgtgcca   3060
tccacgggac tctggagtgt tgaacttgga gggtttcaga ggcagttctc tgggatcctc   3120
gtctcgatca aaggccgtaa attgataatt gttacgaacg taatcagctt tcgagaggca   3180
catacccgt ctatctatga gatctgtaat ctcttgaact ttcacgggaa ccctgtctgt   3240
atatcggttg gttgtaacgg cataggaact cccagaccat accgttgtca taataatgtt   3300
tttatagtat atatttgcct tgaatttata tggcgctata ttttctttaa atattacagc   3360
tataccctcg gtaaaatttt tccctagttt ataatctgga caggcccgtg gtggctctaa   3420
acgcacgaca gtagatcctg aaggtggtgg acacatatag aaagtcgatg gtccgttagc   3480
ctctatttgg gacgcacgga gagcttccct catatccgac atatcggtgg gatctgtagt   3540
tggttttggt ggtgtacccc ctacctcagg ggtagctaca gtccgccggg gttgttccga   3600
tgtgcttcca gattgaccct ctactggacg gggaccgact aagaatagta cgatccagat   3660
aaatgaaaca tatctagcta gtctggttaa tcccgacgat ccgttaccat gtctggagcc   3720
agtcgctgca ataccgagta gagaagggaa aaaacatctc tgtcgaaaat agccactgtg   3780
tccctgccaa cgactccctc gtcgccgctt cccaagatcg ccacgagtgg acattacgat   3840
```

-continued

```
acaaacttaa cggatatcgc gataatgaaa taatttatga ttatttctcg ctttcaattt   3900
aacacaaccc tcaagaacct ttgtatttat tttcactttt taagtataga ataaagaagc   3960
tctaattaat taagctacaa atagtttcgt tttcaccttg tctaataact aattaattaa   4020
cccggatcga tcccgatttt tatgactagt taatcaaata aaaagcatac aagctattgc   4080
ttcgctatcg ttacaaaatg gcaggaattt tgtgtaaact aagccacata cttgccaatg   4140
aaaaaaatag tagaaaggat actattttaa tgggattaga tgttaaggtt ccttgggatt   4200
atagtaactg ggcatctgtt aacttttacg acgttaggtt agatactgat gttacagatt   4260
ataataatgt tacaataaaa tacatgacag gatgtgatat ttttcctcat ataactcttg   4320
gaatagcaaa tatggatcaa tgtgatagat ttgaaaattt caaaaagcaa ataactgatc   4380
aagatttaca gactatttct atagtctgta aagaagagat gtgttttcct cagagtaacg   4440
cctctaaaca gttgggagcg aaaggatgcg ctgtagttat gaaactggag gtatctgatg   4500
aacttagagc cctaagaaat gttctgctga atgcggtacc ctgttcgaag gacgtgtttg   4560
gtgatatcac agtagataat ccgtggaatc ctcacataac agtaggatat gttaaggagg   4620
acgatgtcga aaacaagaaa cgcctaatgg agtgcatgtc caagtttagg gggcaagaaa   4680
tacaagttct aggatggtat taataagtat ctaagtattt ggtataattt attaaatagt   4740
ataattataa caaataataa ataacatgat aacggttttt attagaataa aatagagata   4800
atatcataat gatatataat acttcattac cagaaatgag taatggaaga cttataaatg   4860
aactgcataa agctataagg tatagagata taaatttagt aaggtatata cttaaaaaat   4920
gcaaatacaa taacgtaaat atactatcaa cgtctttgta tttagccgta agtatttctg   4980
atatagaaat ggtaaaatta ttactagaac acggtgccga tattttaaaa tgtaaaaatc   5040
ctcctcttca taaagctgct agtttagata atacagaaat tgctaaacta ctaatagatt   5100
ctggcgctga catagaacag atacattctg gaaatagtcc gttatatatt tctgtatata   5160
gaaacaataa gtcattaact agatatttat taaaaaaagg tgttaattgt aatagattct   5220
ttctaaatta ttacgatgta ctgtatgata agatatctga tgatatgtat aaaatattta   5280
tagattttaa tattgatctt aatatacaaa ctagaaattt tgaaactccg ttacattacg   5340
ctataaagta taagaatata gatttaatta ggatattgtt agataatagt attaaaatag   5400
ataaaagttt atttttgcat aaacagtatc tcataaaggc acttaaaaat aattgtagtt   5460
acgatataat agcgttactt ataaatcacg gagtgcctat aaacgaacaa gatgatttag   5520
gtaaaacccc attacatcat tcggtaatta atagaagaaa agatgtaaca gcacttctgt   5580
taaatctagg agctgatata aacgtaatag atgactgtat gggcagtccc ttacattacg   5640
ctgtttcacg taacgatatc gaaacaacaa agacactttt agaaagagga tctaatgtta   5700
atgtggttaa taatcatata gataccgttc taaatatagc tgttgcatct aaaaacaaaa   5760
ctatagtaaa cttattactg aagtacggta ctgatacaaa gttggtagga ttagataaac   5820
atgttattca catagctata gaaatgaaag atattaatat actgaatgcg atcttattat   5880
atggttgcta tgtaaacgtc tataatcata aaggtttcac tcctctatac atggcagtta   5940
gttctatgaa aacagaattt gttaaactct tacttgacca cggtgcttac gtaaatgcta   6000
aagctaagtt atctggaaat actcctttac ataaagctat gttatctaat agttttaata   6060
atataaaatt acttttatct tataacgccg actataattc tctaaataat cacggtaata   6120
cgcctctaac ttgtgttagc tttttagatg acaagatagc tattatgata atatctaaaa   6180
tgatgttaga aatatctaaa aatcctgaaa tagctaattc agaaggtttt atagtaaaca   6240
```

-continued

```
tggaacatat aaacagtaat aaaagactac tatctataaa agaatcatgc gaaaaagaac   6300

tagatgttat aacacatata aagttaaatt ctatatattc ttttaatatc tttcttgaca   6360

ataacataga tcttatggta aagttcgtaa ctaatcctag agttaataag atacctgcat   6420

gtatacgtat atatagggaa ttaatacgga aaaataaatc attagctttt catagacatc   6480

agctaatagt taaagctgta aaagagagta agaatctagg aataataggt aggttaccta   6540

tagatatcaa acatataata atggaactat taagtaataa tgatttacat tctgttatca   6600

ccagctgttg taacccagta gtataaag                                      6628
```

<210> SEQ ID NO 4
<211> LENGTH: 2700
<212> TYPE: DNA
<213> ORGANISM: Vaccinia virus

<400> SEQUENCE: 4

```
ttttttcat tatttagaaa ttatgcattt tagatcttta taagcggccg tgattaacta      60

gtcataaaaa cccgggatcg attctagact cgagggtacc ggatcttaat aaaaaaagta    120

ataaatcttt aatacgtaaa atctagaaat attcgccggc actaattgat cagtattttt    180

gggccctagc taagatctga gctcccatgg cctagaatta taattagtca tcaggcaggg    240

cgagaacgag actatctgct cgttaattaa ttaggtcgac ggatccccca acaaaaacta    300

atcagctatc ggggttaatt aattagttat attaatcagt agtccgtccc gctcttgctc    360

tgatagacga gcaattaatt aatccagctg cctagggggt tgtttttgat tagtcgatag    420

ccccaattaa ttaatcaata tagacaaggt gaaaacgaaa ctatttgtag cttaattaat    480

tagagcttct ttattctata cttaaaaagt gaaaataaat acaaaggttc ttgagggttg    540

tgttaaattg atctgttcca cttttgcttt gataaacatc gaattaatta atctcgaaga    600

aataagatat gaatttttca cttttattta tgtttccaag aactcccaac acaatttaac    660

aaagcgagaa ataatcataa attatttcat tatcgcgata tccgttaagt ttgtatcgta    720

atgccactaa cagaagaagc agagctagaa ctggcagaaa actttcgctc tttattagta    780

tttaataaag taatagcgct ataggcaatt caaacatagc attacggtga ttgtcttctt    840

cgtctcgatc ttgaccgtct tttgagagag attctaaaag aaccagtaca tggagtgtat    900

tatgacccat caaaagactt aatagcagaa atacagaagc aggggcaagg ccaatctctc    960

taagattttc ttggtcatgt acctcacata atactgggta gttttctgaa ttatcgtctt   1020

tatgtcttcg tccccgttcc ggtttggaca tatcaaattt atcaagagcc atttaaaaat   1080

ctgaaaacag gaatggagtg gagatttgat tctagattag catttcatca cgtaacctgt   1140

atagtttaaa tagttctcgg taaattttta gacttttgtc cttacctcac ctctaaacta   1200

agatctaatc gtaaagtagt gcatgctaga gaattacatc ctgaatattt taaaaattgt   1260

aagcttatgg caatattcca aagtagcatg acaaaaatct tagagccttt tagacgatct   1320

cttaatgtag gacttataaa atttttaaca ttcgaatacc gttataaggt ttcatcgtac   1380

tgtttttaga atctcggaaa atctaaacaa aatccagaca tagttatcta tcaatacatg   1440

gatgatttgt atgtaggatc tgacttagaa atagggcagc atagaacaaa aatatttgtt   1500

ttaggtctgt atcaatagat agttatgtac ctactaaaca tacatcctag actgaatctt   1560

tatcccgtcg tatcttgttt ttatgaggag ctgagacaac atctgttgag gtggggactt   1620

acaaccatgg taggttttcc agtaacacct caagtacctt taagaccaat gactctcctc   1680

gactctgttg tagacaactc cacccctgaa tgttggtacc atccaaaagg tcattgtgga   1740
```

```
gttcatggaa attctggtta ctgatacaaa gcagctgtag atctttctca ctttttaaaa   1800

gaaaaaggag gtttagaagg gctaattcat tctcaacgaa gacaagatat tcttatgttt   1860

cgtcgacatc tagaaagagt gaaaaatttt ctttttcctc caaatcttcc cgattaagta   1920

agagttgctt ctgttctata agaagatttg tggatttatc atacacaagg atattttcct   1980

gattggcaga attacacacc aggaccagga gtcagatacc cattaacctt tggtctaaac   2040

acctaaatag tatgtgttcc tataaaagga ctaaccgtct taatgtgtgg tcctggtcct   2100

cagtctatgg gtaattggaa accatggtgc tacaagctag taccaatgat tgagactgta   2160

ccagtaaaat taaagccagg aatggatggc ccaaaagtta aacaatggcc attgaccacg   2220

atgttcgatc atggttacta actctgacat ggtcatttta atttcggtcc ttacctaccg   2280

ggttttcaat ttgttaccgg taacacagaa gaaaaaataa aagcattagt agaaatttgt   2340

acagagatgg aaaaggaagg gaaaatttca aaaattgggc cttaattttt cttgtcttct   2400

tttttatttt cgtaatcatc tttaaacatg tctctacctt ttccttccct tttaaagttt   2460

ttaacccgga attaaaaaga gcagcccggg ggatcctttt tatagctaat tagtcacgta   2520

cctttgagag taccacttca gctacctctt ttgtgtctca gagtaacttt ctttaatcaa   2580

ttccaaaaca cgtcgggccc cctaggaaaa atatcgatta atcagtgcat ggaaactctc   2640

atggtgaagt cgatggagaa aacacagagt ctcattgaaa gaaattagtt aaggttttgt   2700
```

<210> SEQ ID NO 5
<211> LENGTH: 266
<212> TYPE: PRT
<213> ORGANISM: Vaccinia virus

<400> SEQUENCE: 5

```
Arg Glu Ile Leu Lys Glu Pro Val His Gly Val Tyr Tyr Asp Pro Ser
  1               5                  10                  15

Lys Asp Leu Ile Ala Glu Ile Gln Lys Gln Gly Gln Gly Gln Trp Thr
             20                  25                  30

Tyr Gln Ile Tyr Gln Glu Pro Phe Lys Asn Leu Lys Thr Gly Met Glu
         35                  40                  45

Trp Arg Phe Asp Ser Arg Leu Ala Phe His His Val Ala Arg Glu Leu
     50                  55                  60

His Pro Glu Tyr Phe Lys Asn Cys Lys Leu Met Ala Ile Phe Gln Ser
 65                  70                  75                  80

Ser Met Thr Lys Ile Leu Glu Pro Phe Arg Lys Gln Asn Pro Asp Ile
                 85                  90                  95

Val Ile Tyr Gln Tyr Met Asp Asp Leu Tyr Val Gly Ser Asp Leu Glu
            100                 105                 110

Ile Gly Gln His Arg Thr Lys Ile Glu Glu Leu Arg Gln His Leu Leu
        115                 120                 125

Arg Trp Gly Leu Thr Thr Met Val Gly Phe Pro Val Thr Pro Gln Val
    130                 135                 140

Pro Leu Arg Pro Met Thr Tyr Lys Ala Ala Val Asp Leu Ser His Phe
145                 150                 155                 160

Leu Lys Glu Lys Gly Gly Leu Glu Gly Leu Ile His Ser Gln Arg Arg
                165                 170                 175

Gln Asp Ile Leu Asp Leu Trp Ile Tyr His Thr Gln Gly Tyr Phe Pro
            180                 185                 190

Asp Trp Gln Asn Tyr Thr Pro Gly Pro Gly Val Arg Tyr Pro Leu Thr
        195                 200                 205
```

-continued

```
Phe Gly Trp Cys Tyr Lys Leu Val Pro Met Ile Glu Thr Val Pro Val
    210                 215                 220

Lys Leu Lys Pro Gly Met Asp Gly Pro Lys Val Lys Gln Trp Pro Leu
225                 230                 235                 240

Thr Glu Glu Lys Ile Lys Ala Leu Val Glu Ile Cys Thr Glu Met Glu
                245                 250                 255

Lys Glu Gly Lys Ile Ser Lys Ile Gly Pro
            260                 265
```

<210> SEQ ID NO 6
<211> LENGTH: 7616
<212> TYPE: DNA
<213> ORGANISM: Vaccinia virus

<400> SEQUENCE: 6

```
taatgtagta tactaatatt aactcacatt tgactaatta gctataaaaa cccgggatcg     60

attctagaat aaaaattatc cctgcctaac tctattcact acagagagta cagcaaaaac    120

attacatcat atgattataa ttgagtgtaa actgattaat cgatattttt gggccctagc    180

taagatctta tttttaatag ggacggattg agataagtga tgtctctcat gtcgtttttg    240

tattcttaaa cctaccaagc ctcctactat cattatgaat aatctttttt ctctctgcac    300

cactcttctc tttgccttgg tgggtgctac tcctaatggt tcaattgtta ctactttata    360

ataagaattt ggatggttcg gaggatgata gtaatactta ttagaaaaaa gagagacgtg    420

gtgagaagag aaacggaacc acccacgatg aggattacca agttaacaat gatgaaatat    480

tttatataat tcacttctcc aattgtccct catatctcct cctccaggtc tgaagatctc    540

ggtgtcgttc gtgtccgtgt ccttaccacc atctcttgtt aatagtagcc ctgtaatatt    600

aaatatatta agtgaagagg ttaacaggga gtatagagga ggaggtccag acttctagag    660

ccacagcaag cacaggcaca ggaatggtgg tagagaacaa ttatcatcgg gacattataa    720

tgatgaacat ctaatttgtc cttcaatggg aggggcatat attgcttttc ctacttcctg    780

ccacatgttt ataatttgtt ttattttgca ttgaagtgtg atattgttat ttgaccctgt    840

actacttgta gattaaacag gaagttaccc tccccgtata taacgaaaag gatgaaggac    900

ggtgtacaaa tattaaacaa aataaaacgt aacttcacac tataacaata aactgggaca    960

agtattattc caagtattat taccattcca agtactatta aacagtggtg atgaattaca   1020

gtagaagaat tcccctccac aattaaaact gtgcattaca atttctgggt cccctcctga   1080

tcataataag gttcataata atggtaaggt tcatgataat ttgtcaccac tacttaatgt   1140

catcttctta aggggaggtg ttaattttga cacgtaatgt taaagaccca ggggaggact   1200

ggattgatta aagactattg ttttattctt aaattgttct tttaatttgc taactatctg   1260

tcttaaagtg tcattccatt ttgctctact aatgttacaa tgtgcttgtc ttatagttcc   1320

cctaactaat ttctgataac aaaataagaa tttaacaaga aaattaaacg attgatagac   1380

agaatttcac agtaaggtaa aacgagatga ttacaatgtt acacgaacag aatatcaagg   1440

tattatattt tttgttgtat aaaatgctct ccctggtcct atatgtatcc tttttctttt   1500

attgtagttg ggtcttgtac aattaatttg tacagattca ttcagatgta ctatgatggt   1560

ataatataaa aaacaacata ttttacgaga gggaccagga tatacatagg aaaaagaaaa   1620

taacatcaac ccagaacatg ttaattaaac atgtctaagt aagtctacat gatactacca   1680

tttagcatta tcattgaaat tctcagatct aattactacc tcttcttctg ctagactgcc   1740

atttaacagc agttgagttg atactactgg cctaattcca tgtgtacatt gtactgtgct   1800
```

-continued

```
aaatcgtaat agtaacttta agagtctaga ttaatgatgg agaagaagac gatctgacgg   1860
taaattgtcg tcaactcaac tatgatgacc ggattaaggt acacatgtaa catgacacga   1920
gacattttta catgatcctt ttccactgaa ctttttatcg ttacacttta gaatcgcaaa   1980
accagccggg gcacaatagt gtatgggaat tggctcaaag gatatctttg gacaagcttg   2040
ctgtaaaaat gtactaggaa aaggtgactt gaaaaatagc aatgtgaaat cttagcgttt   2100
tggtcggccc cgtgttatca catacccta accgagtttc ctatagaaac ctgttcgaac   2160
tgtaatgact gaggtattac aacttatcaa cctatagctg gtactatcat tatttattga   2220
tactatatca agtttataaa gaagtgcata ttctttctgc atcttatctc ttatgcttgt   2280
acattactga ctccataatg ttgaatagtt ggatatcgac catgatagta ataaataact   2340
atgatatagt tcaaatattt cttcacgtat aagaaagacg tagaatagag aatacgaaca   2400
ggtgatattg aaagagcagt tttcatttc tcctcccttt attgttccct cgctattact   2460
attgttatta gcagtactat tattggtatt agtagtattc ctcaaatcag tgcaatttaa   2520
ccactataac tttctcgtca aaaagtaaag aggagggaaa taacaaggga gcgataatga   2580
taacaataat cgtcatgata ataaccataa tcatcataag gagtttagtc acgttaaatt   2640
agtaacacag agtggggtta attttacaca tggctttagg ctttgatccc ataaactgat   2700
tatatcctca tgcatctgtt ctaccatgtt atttttccac atgttaaaat tttctgtcac   2760
tcattgtgtc tcaccccaat taaaatgtgt accgaaatcc gaaactaggg tatttgacta   2820
atataggagt acgtagacaa gatggtacaa taaaaaggtg tacaatttta aaagacagtg   2880
atttaccaat tctacttctt gtgggttggg gtctgtgggt acacaggcat gtgtggccca   2940
aacattatgt acctctgtat catatgcttt agcatctgat gcacaaaata gagtggtggt   3000
taaatggtta agatgaagaa cacccaaccc cagacaccca tgtgtccgta cacaccgggt   3060
ttgtaataca tggagacata gtatacgaaa tcgtagacta cgtgttttat ctcaccacca   3120
tgcttctttc cacacaggta ccccataata gactgtgacc cacaattttt ctgtagcact   3180
acagatcatc aacatcccaa ggagcatggt gccccatctc caccccccatc tccacaagtg   3240
acgaagaaag gtgtgtccat ggggtattat ctgacactgg gtgttaaaaa gacatcgtga   3300
tgtctagtag ttgtagggtt cctcgtacca cggggtagag gtgggggtag aggtgttcac   3360
ctgatatttc tccttcactc tcattgccac tgtcttctgc tctttcatat acgatacaaa   3420
cttaacgcat atcgcgataa tgaaataatt tatgattatt tctcgctttc aatttaacac   3480
gactataaag aggaagtgag agtaacggtg acagaagacg agaaagtata tgctatgttt   3540
gaattgcgta tagcgctatt actttattaa atactaataa agagcgaaag ttaaattgtg   3600
aaccctcaag aacctttgta tttattttca ctttttaagt atagaataaa gaagctctaa   3660
ttaattaagc tacaaatagt ttcgttttca ccttgtctaa taactaatta attaacccgg   3720
ttgggagttc ttggaaacat aaataaaagt gaaaaattca tatcttattt cttcgagatt   3780
aattaattcg atgtttatca aagcaaaagt ggaacagatt attgattaat taattgggcc   3840
atcttgagat aaagtgaaaa tatatatcat tatattacaa agtacaatta tttaggttta   3900
atcatgggtg cgagagcgtc agtattaagc gggggagaat tagatcgatg ggaaaaaatt   3960
tagaactcta tttcactttt atatatagta atataatgtt tcatgttaat aaatccaaat   4020
tagtacccac gctctcgcag tcataattcg ccccctctta atctagctac cctttttaa   4080
cggttaaggc cagggggaaa gaaaaaatat aaattaaaac atatagtatg ggcaagcagg   4140
gagctagaac gattcgcagt taatcctggc ctgttagaaa catcagaagg ctgtagacaa   4200
```

-continued

```
gccaattccg gtccccccttt cttttttata tttaattttg tatatcatac ccgttcgtcc   4260
ctcgatcttg ctaagcgtca attaggaccg gacaatcttt gtagtcttcc gacatctgtt   4320
atactgggac agctacaacc atcccttcag acaggatcag aagaacttag atcattatat   4380
aatacagtag caaccctcta ttgtgtgcat caaaggatag agataaaaga caccaaggaa   4440
tatgaccctg tcgatgttgg tagggaagtc tgtcctagtc ttcttgaatc tagtaatata   4500
ttatgtcatc gttgggagat aacacacgta gtttcctatc tctattttct gtggttcctt   4560
gctttagaca agatagagga agagcaaaac aaaagtaaga aaaaagcaca gcaagcagca   4620
gctgacacag gacacagcaa tcaggtcagc caaaattacc ctatagtgca gaacatccag   4680
cgaaatctgt tctatctcct tctcgttttg ttttcattct tttttcgtgt cgttcgtcgt   4740
cgactgtgtc ctgtgtcgtt agtccagtcg gttttaatgg gatatcacgt cttgtaggtc   4800
gggcaaatgg tacatcaggc catatcacct agaactttaa atgcatgggt aaaagtagta   4860
gaagagaagg ctttcagccc agaagtgata cccatgtttt cagcattatc agaaggagcc   4920
cccgtttacc atgtagtccg gtatagtgga tcttgaaatt tacgtaccca ttttcatcat   4980
cttctcttcc gaaagtcggg tcttcactat gggtacaaaa gtcgtaatag tcttcctcgg   5040
accccacaag atttaaacac catgctaaac acagtggggg gacatcaagc agccatgcaa   5100
atgttaaaag agaccatcaa tgaggaagct gcagaatggg atagagtgca tccagtgcat   5160
tggggtgttc taaatttgtg gtacgatttg tgtcaccccc ctgtagttcg tcggtacgtt   5220
tacaattttc tctggtagtt actccttcga cgtcttaccc tatctcacgt aggtcacgta   5280
gcagggccta ttgcaccagg ccagatgaga gaaccaaggg gaagtgacat agcaggaact   5340
actagtaccc ttcaggaaca aataggatgg atgacaaata atccacctat cccagtagga   5400
cgtcccggat aacgtggtcc ggtctactct cttggttccc cttcactgta tcgtccttga   5460
tgatcatggg aagtccttgt ttatcctacc tactgtttat taggtggata gggtcatcct   5520
gaaatttata aaagatggat aatcctggga ttaaataaaa tagtaagaat gtatagccct   5580
accagcattc tggacataag acaaggacca aaagaaccct ttagagacta tgtagaccgg   5640
ctttaaatat tttctaccta ttaggaccct aatttatttt atcattctta catatcggga   5700
tggtcgtaag acctgtattc tgttcctggt tttcttggga aatctctgat acatctggcc   5760
ttctataaaa ctctaagagc cgagcaagct tcacaggagg taaaaaattg gatgacagaa   5820
accttgttgg tccaaaatgc gaacccagat tgtaagacta ttttaaaagc attgggacca   5880
aagatatttt gagattctcg gctcgttcga agtgtcctcc attttttaac ctactgtctt   5940
tggaacaacc aggttttacg cttgggtcta acattctgat aaaattttcg taaccctggt   6000
gcggctacac tagaagaaat gatgacagca tgtcagggag taggaggacc cggccataag   6060
gcaagagttt tggctgaagc aatgagccaa gtaacaaatt cagctaccat aatgatgcag   6120
cgccgatgtg atcttcttta ctactgtcgt acagtccctc atcctcctgg gccggtattc   6180
cgttctcaaa accgacttcg ttactcggtt cattgtttaa gtcgatggta ttactacgtc   6240
agaggcaatt ttaggaacca aagaaagatt gttaagtgtt tcaattgtgg caaagaaggg   6300
cacacagcca gaaattgcag ggcccctagg aaaaagggct gttggaaatg tggaaaggaa   6360
tctccgttaa aatccttggt ttctttctaa caattcacaa agttaacacc gtttcttccc   6420
gtgtgtcggt ctttaacgtc ccggggatcc tttttcccga caacctttac acctttcctt   6480
ggacaccaaa tgaaagattg tactgagaga caggctaatt ttttagggaa gatctggcct   6540
tcctacaagg gaaggccagg gaattttctt cagagcagac cagagccaac agccccacca   6600
```

-continued

```
cctgtggttt actttctaac atgactctct gtccgattaa aaaatccctt ctagaccgga   6660

aggatgttcc cttccggtcc cttaaaagaa gtctcgtctg gtctcggttg tcggggtggt   6720

gaagagagct tcaggtctgg ggtagagaca acaactcccc ctcagaagca ggagccgata   6780

gacaaggaac tgtatccttt aacttccctc agatcactct ttggcaacga cccctcgtca   6840

cttctctcga agtccagacc ccatctctgt tgttgagggg gagtcttcgt cctcggctat   6900

ctgttccttg acataggaaa ttgaagggag tctagtgaga aaccgttgct ggggagcagt   6960

caataaagat agggggcaa ctaaaggaag ctctattaga tacaggagca gatgatacag   7020

tattagaaga aatgagtttg ccaggaagat ggaaaccaaa aatgataggg ggaattggag   7080

gttatttcta tccccccgtt gatttccttc gagataatct atgtcctcgt ctactatgtc   7140

ataatcttct ttactcaaac ggtccttcta cctttggttt ttactatccc ccttaacctc   7200

gttttatcaa agtaagacag tatgatcaga tactcataga aatctgtgga cataaagcta   7260

taggtacagt attagtagga cctacacctg tcaacataat tggaagaaat ctgttgactc   7320

caaaatagtt tcattctgtc atactagtct atgagtatct ttagacacct gtatttcgat   7380

atccatgtca taatcatcct ggatgtggac agttgtatta accttcttta gacaactgag   7440

agattggttg cactttaaat ttttaacccg gggatcccg atttttatga ctagttaatc   7500

aaataaaaag catacaagct attgcttctc taaccaacgt gaaatttaaa aattgggccc   7560

cctagggcta aaaatactga tcaattagtt tatttttcgt atgttcgata acgaag       7616
```

<210> SEQ ID NO 7
<211> LENGTH: 8868
<212> TYPE: DNA
<213> ORGANISM: Vaccinia virus

<400> SEQUENCE: 7

```
gagctcgcgg ccgcctatca aaagtcttaa tgagttaggt gtagatagta tagatattac     60

tacaaaggta ttcatatttc ctatcaattc taaagtagat gatattaata ctcgagcgcc    120

ggcggatagt tttcagaatt actcaatcca catctatcat atctataatg atgtttccat    180

aagtataaag gatagttaag atttcatcta ctataattat actcaaagat gatgatagta    240

gataatagat acgctcatat aatgactgca aatttggacg gttcacattt taatcatcac    300

gcgttcataa gtttcaactg catagatcaa tgagtttcta ctactatcat ctattatcta    360

tgcgagtata ttactgacgt ttaaacctgc caagtgtaaa attagtagtg cgcaagtatt    420

caaagttgac gtatctagtt aatctcacta aaaagatagc cgatgtattt gagagagatt    480

ggacatctaa ctacgctaaa gaaattacag ttataaataa tacataatgg attttgttat    540

catcagttat ttagagtgat ttttctatcg gctacataaa ctctctctaa cctgtagatt    600

gatgcgattt ctttaatgtc aatatttatt atgtattacc taaaacaata gtagtcaata    660

atttaacata agtacaataa aaagtattaa ataaaaatac ttacttacga aaaaatgact    720

aattagctat aaaaacccag atctctcgag gtcgacggta tcgataagct taaattgtat    780

tcatgttatt tttcataatt tatttttatg aatgaatgct tttttactga ttaatcgata    840

tttttgggtc tagagagctc cagctgccat agctattcga tgatatcgaa ttcataaaaa    900

ttattgatgt ctacacatcc ttttgtaatt gacatctata tatccttttg tataatcaac    960

tctaatcact ttactatagc ttaagtattt ttaataacta cagatgtgta ggaaaacatt   1020

aactgtagat atataggaaa acatattagt tgagattagt gaaaaacttt tacagttttc   1080

cctaccagtt tatccctata ttcaacatat ctatccatat gcatcttaac actctctgcc   1140
```

-continued

```
aagatagctt cagattgaaa atgtcaaaag ggatggtcaa atagggatat aagttgtata   1200
gataggtata cgtagaattg tgagagacgg ttctatcgaa gtctgtgagg atagtcaaaa   1260
agataaatgt atagagcata atccttctcg tatactctgc cctttattac atcgcccgca   1320
ttgggcaacg aatacactcc tatcagtttt tctatttaca tatctcgtat taggaagagc   1380
atatgagacg ggaaataatg tagcgggcgt aacccgttgc ttatacaaaa tgcaagcata   1440
cgatacaaac ttaacggata tcgcgataat gaaataattt atgattattt ctcgctttca   1500
atttaacaca accctcaaga actgttttac gttcgtatgc tatgtttgaa ttgcctatag   1560
cgctattact ttattaaata ctaataaaga gcgaaagtta aattgtgttg ggagttcttg   1620
ctttgtattt attttcactt tttaagtata gaataaagaa agctctaatt aattaatgaa   1680
cagattgttt cgttttcccc ttggcgtatc actaattaat taacccgggc gaaacataaa   1740
taaaagtgaa aaattcatat cttatttctt tcgagattaa ttaattactt gtctaacaaa   1800
gcaaaagggg aaccgcatag tgattaatta attgggcccg tgcagctcga ggaattcaac   1860
tatatcgaca tatttcattt gtatacacat aaccattact aacgtagaat gtataggaag   1920
agatgtaacg ggaacagggt ttgttgattc acgtcgagct ccttaagttg atatagctgt   1980
ataaagtaaa catatgtgta ttggtaatga ttgcatctta catatccttc tctacattgc   2040
ccttgtccca aacaactaag gcaaactatt ctaatacata attcttctgt taatacgtct   2100
tgcacgtaat ctattataga tgccaagata tctatataat tattttgtaa gatgatgtta   2160
actatgtgat cgtttgataa gattatgtat taagaagaca attatgcaga acgtgcatta   2220
gataatatct acggttctat agatatatta ataaaacatt ctactacaat tgatacacta   2280
ctatataagt agtgtaataa ttcatgtatt tcgatatatg ttccaactct gtctttgtga   2340
tgtctagttt cgtaatatct atagcatcct caaaaaatat attcgcatat gatatattca   2400
tcacattatt aagtacataa agctatatac aaggttgaga cagaaacact acagatcaaa   2460
gcattataga tatcgtagga gttttttata taagcgtata attcccaagt cttcagttct   2520
atcttctaaa aaatcttcaa cgtatggaat ataataatct attttacctc ttctgatatc   2580
attaatgata tagtttttga cactatcttc taagggttca gaagtcaaga tagaagattt   2640
tttagaagtt gcatacctta tattattaga taaaatggag aagactatag taattactat   2700
atcaaaaact gtgatagaag tgtcaattga ttcttattca ctatatctaa gaaacggata   2760
gcgtccctag gacgaactac tgccattaat atctctatta tagcttctgg acataattca   2820
tctattatac acagttaact aagaataagt gatatagatt ctttgcctat cgcagggatc   2880
ctgcttgatg acggtaatta tagagataat atcgaagacc tgtattaagt agataatatg   2940
cagaattaat gggaactatt ccgtatctat ctaacatagt tttaagaaag tcagaatcta   3000
agacctgatg ttcatatatt ggttcataca tgaaatgatc tctattgatg gtcttaatta   3060
cccttgataa ggcatagata gattgtatca aaattctttc agtcttagat tctggactac   3120
aagtatataa ccaagtatgt actttactag agataactac atagtgacta tttcattctc   3180
tgaaaattgg taactcattc tatatatgct ttccttgttg atgaaggata gaatatactc   3240
aatagaattt gtaccaacaa actgttctct tatcactgat aaagtaagag acttttaacc   3300
attgagtaag atatatacga aaggaacaac tacttcctat cttatatgag ttatcttaaa   3360
catggttgtt tgacaagaga tatgaatcgt atatcatcat ctgaaataat catgtaaggc   3420
atacatttaa caattagaga cttgtctcct gttatcaata tactattctt gtgataattt   3480
atgtgtgagg atacttagca tatagtagta gactttatta gtacattccg tatgtaaatt   3540
```

-continued gttaatctct gaacagagga caatagttat atgataagaa cactattaaa tacacactcc 3600
caaatttgtc cacgttcttt aattttgtta tagtagatat caaatccaat ggagctacag 3660
ttcttggctt aaacagatat agtttttctg gaacaaattc tacaacatta gtttaaacag 3720
gtgcaagaaa ttaaaacaat atcatctata gtttaggtta cctcgatgtc aagaaccgaa 3780
tttgtctata tcaaaaagac cttgtttaag atgttgtaat ttataaagga ctttgggtag 3840
ataagtggga tgaaatccta ttttaattaa tgctatcgca ttgtcctcgt gcaaatatcc 3900
aaacgctttt gtgatagtat ggcattcatt aatatttcct gaaacccatc tattcaccct 3960
actttaggat aaaattaatt acgatagcgt aacaggagca cgtttatagg tttgcgaaaa 4020
cactatcata ccgtaagtaa gtctagaaac gctctacgaa tatctgtgac agatatcatc 4080
tttagagaat atactagtcg cgttaatagt actacaattt gtattttta atctatctca 4140 ataaaaaaat cagatctttg cgagatgctt atagacactg tctatagtag aaatctctta 4200
tatgatcagc gcaattatca tgatgttaaa cataaaaaat tagatagagt tatttttta 4260 taatatgtat gattcaatgt ataactaaac tactaactgt tattgataac tagaatcaga 4320
atctaatgat gacgtaacca agaagtttat ctactgccaa attatacata ctaagttaca 4380
tattgatttg atgattgaca ataactattg atcttagtct tagattacta ctgcattggt 4440
tcttcaaata gatgacggtt tttagctgca ttatttttag catctcgttt agattttcca 4500
tctgccttat cgaatactct tccgtcgatg tctacacagg cataaaatgt aaatcgacgt 4560
aataaaaatc gtagagcaaa tctaaaaggt agacggaata gcttatgaga aggcagctac 4620
agatgtgtcc gtattttaca aggagagtta ctaggcccaa ctgattcaat acgaaaagac 4680
caatctctct tagttatttg gcagtactca ttaataatgg tgacagggtt tcctctcaat 4740
gatccgggtt gactaagtta tgcttttctg gttagagaga atcaataaac cgtcatgagt 4800
aattattacc actgtcccaa agcatctttc caatcaataa tttttttagc cggaataaca 4860
tcatcaaaag acttatgatc ctctctcatt gatttttcgc gggatacatc tcgtagaaag 4920
gttagttatt aaaaaaatcg gccttattgt agtagttttc tgaatactag gagagagtaa 4980
ctaaaaagcg ccctatgtag atctattatg acgtcagcca tagcatcagc atccggctta 5040
tccgcctccg ttgtcataaa ccaacgagga ggaatatcgt cggagctgta tagataatac 5100
tgcagtcggt atcgtagtcg taggccgaat aggcggaggc aacagtattt ggttgctcct 5160
ccttatagca gcctcgacat caccatagca ctacgttgaa gatcgtacag agctttatta 5220
acttctcgct tctccatatt aagttgtcta gttagttgtg cagcagtagc gtggtatcgt 5280
gatgcaactt ctagcatgtc tcgaaataat tgaagagcga agaggtataa ttcaacagat 5340
caatcaacac gtcgtcatcg tccttcgatt ccaatgtttt taatagccgc acacacaatc 5400
tctgcgtcag aacgctcgtc aatatagatc ttagacattt ttagagagaa aggaagctaa 5460
ggttacaaaa attatcggcg tgtgtgttag agacgcagtc ttgcgagcag ttatatctag 5520
aatctgtaaa aatctctctt ctaacacaac cagcaataaa actgaaccta ctttatcatt 5580
tttttattca tcatcctctg gtggttcgtc gtttctatcg aatgtagctc tgattaaccc 5640
gtcatctata gattgtgttg gtcgttattt tgacttggat gaaatagtaa aaaaataagt 5700
agtaggagac caccaagcag caaagatagc ttacatcgag actaattggg cagtagatat 5760
ggtgatgctg gttctggaga ttctggagga gatggattat tatctggaag aatctctgtt 5820
atttccttgt tttcatgtat cgattgcgtt gtaacattaa gattgcgaaa ccactacgac 5880
caagacctct aagacctcct ctacctaata atagaccttc ttagagacaa taaaggaaca 5940

-continued aaagtacata gctaacgcaa cattgtaatt ctaacgcttt tgctctaaat ttgggaggct 6000
taaagtgttg tttgcaatct ctacacgcgt gtctaactag tggaggttcg tcagctgctc 6060
tagtttgaat catcatcggc gtagtattcc acgagattta aaccctccga atttcacaac 6120
aaacgttaga gatgtgcgca cagattgatc acctccaagc agtcgacgag atcaaactta 6180
gtagtagccg catcataagg tacttttaca gttaggacac ggtgtattgt atttctcgtc 6240
gagaacgtta aaataatcgt tgtaactcac atcctttatt ttatctatat tgtattctac 6300
tcctttctta atgaaaatgt caatcctgtg ccacataaca taaagagcag ctcttgcaat 6360
tttattagca acattgagtg taggaaataa aatagatata acataagatg aggaaagaat 6420
atgcatttta taccgaataa gagatagcga aggaattctt tttattgatt aactagtcaa 6480
atgagtatat ataattgaaa aagtaaaata taaatcatat aataatgaaa tacgtaaaat 6540
atggcttatt ctctatcgct tccttaagaa aaataactaa ttgatcagtt tactcatata 6600
tattaacttt ttcattttat atttagtata ttattacttt cgaaatatca gtaatagaca 6660
ggaactggca gattcttctt ctaatgaagt aagtactgct aaatctccaa aattagataa 6720
aaatgataca gcaaatacag cttcattcaa gctttatagt cattatctgt ccttgaccgt 6780
ctaagaagaa gattacttca ttcatgacga tttagaggtt ttaatctatt tttactatgt 6840
cgtttatgtc gaagtaagtt cgaattacct tttaattttt tcagacacac cttattacaa 6900
actaactaag tcagatgatg agaaagtaaa tataaattta acttatgggt ataatataat 6960
aaagattcat gcttaatgga aaattaaaaa agtctgtgtg gaataatgtt tgattgattc 7020
agtctactac tctttcattt atatttaaat tgaataccca tattatatta tttctaagta 7080
gatattaata atttacttaa cgatgttaat agacttattc catcaacccc ttcaaacctt 7140
tctggatatt ataaaatacc agttaatgat attaaaatag attgtttaag ctataattat 7200
taaatgaatt gctacaatta tctgaataag gtagttgggg aagtttggaa agacctataa 7260
tattttatgg tcaattacta taattttatc taacaaattc agatgtaaat aattatttgg 7320
aggtaaagga tataaaatta gtctatcttt cacatggaaa tgaattacct aatattaata 7380
attatgatag gaatttttta ggatttacag tctacattta ttaataaacc tccatttcct 7440
atattttaat cagatagaaa gtgtaccttt acttaatgga ttataattat taatactatc 7500
cttaaaaaat cctaaatgtc ctgttatatg tatcaacaat acaggcagat ctatggttat 7560
ggtaaaacac tgtaacggga agcagcattc tatggtaact ggcctatgtt taatagccag 7620
atcattttac gacaatatac atagttgtta tgtccgtcta gataccaata ccattttgtg 7680
acattgccct tcgtcgtaag ataccattga ccggatacaa attatcggtc tagtaaaatg 7740
tctataaaca ttttaccaca aataatagga tcctctagat atttaatatt atatctaaca 7800
acaacaaaaa aatttaacga tgtatggcca gaagtatttt ctactaataa agatatttgt 7860
aaaatggtgt ttattatcct aggagatcta taaattataa tatagattgt tgttgttttt 7920
ttaaattgct acataccggt cttcataaaa gatgattatt agataaagat agtctatctt 7980
atctacaaga tatgaaagaa gataatcatt tagtagtagc tactaatatg gaaagaaatg 8040
tatacaaaaa cgtggaagct tttatattaa tctatttcta tcagatagaa tagatgttct 8100
atactttctt ctattagtaa atcatcatcg atgattatac ctttctttac atatgttttt 8160
gcaccttcga aaatataatt atagcatatt actagaagat ttaaaatcta gacttagtat 8220
aacaaaacag ttaaatgcca atatcgattc tatatttcat cataacagta gtacattaat 8280
cagtgatata tatcgtataa tgatcttcta aattttagat ctgaatcata ttgttttgtc 8340

-continued

```
aatttacggt tatagctaag atataaagta gtattgtcat catgtaatta gtcactatat   8400

ctgaaacgat ctacagactc aactatgcaa ggaataagca atatgccaat tatgtctaat   8460

attttaactt tagaactaaa acgttctacc aatactaaaa ataggatacg gactttgcta   8520

gatgtctgag ttgatacgtt ccttattcgt tatacggtta atacagatta taaaattgaa   8580

atcttgattt tgcaagatgg ttatgatttt tatcctatgc tgataggctg ttaaaagctg   8640

caataaatag taaggatgta gaagaaatac tttgttctat accttcggag gaaagaactt   8700

tagaacaact taagtttaat caaacttgta actatccgac aattttcgac gttatttatc   8760

attcctacat cttctttatg aaacaagata tggaagcctc ctttcttgaa atcttgttga   8820

attcaaatta gtttgaacat tttatgaagg taccaaatac ttccatgg                8868


<210> SEQ ID NO 8
<211> LENGTH: 59
<212> TYPE: DNA
<213> ORGANISM: Vaccinia virus

<400> SEQUENCE: 8

ccctctagat cgcgatatcc gttaagtttg tatcgtaatg cttgcatttt gttattcgt      59


<210> SEQ ID NO 9
<211> LENGTH: 31
<212> TYPE: DNA
<213> ORGANISM: Vaccinia virus

<400> SEQUENCE: 9

cccgaattca taaaaattat tgatgtctac a                                    31


<210> SEQ ID NO 10
<211> LENGTH: 17
<212> TYPE: DNA
<213> ORGANISM: Vaccinia virus

<400> SEQUENCE: 10

ggccgcgtcg acatgca                                                    17


<210> SEQ ID NO 11
<211> LENGTH: 9
<212> TYPE: DNA
<213> ORGANISM: Vaccinia virus

<400> SEQUENCE: 11

tgtcgacgc                                                              9


<210> SEQ ID NO 12
<211> LENGTH: 55
<212> TYPE: DNA
<213> ORGANISM: Vaccinia virus

<400> SEQUENCE: 12

tttcattatc gcgatatccg ttaagtttgt atcgtaatgt ccactcgtgg cgatc          55


<210> SEQ ID NO 13
<211> LENGTH: 18
<212> TYPE: DNA
<213> ORGANISM: Vaccinia virus

<400> SEQUENCE: 13

ggagggtttc agaggcag                                                   18


<210> SEQ ID NO 14
```

<211> LENGTH: 58
<212> TYPE: DNA
<213> ORGANISM: Vaccinia virus

<400> SEQUENCE: 14
cccctcgagt cgcgatatcc gttaagtttg tatcgtaatg ccactaacag aagaagca 58

<210> SEQ ID NO 15
<211> LENGTH: 36
<212> TYPE: DNA
<213> ORGANISM: Vaccinia virus

<400> SEQUENCE: 15
aaatctccac tccatccttg ttttcagatt tttaaa 36

<210> SEQ ID NO 16
<211> LENGTH: 36
<212> TYPE: DNA
<213> ORGANISM: Vaccinia virus

<400> SEQUENCE: 16
aatctgaaaa caggaatgga gtggagattt gattct 36

<210> SEQ ID NO 17
<211> LENGTH: 30
<212> TYPE: DNA
<213> ORGANISM: Vaccinia virus

<400> SEQUENCE: 17
cccaagctta caatttttaa aatattcagg 30

<210> SEQ ID NO 18
<211> LENGTH: 30
<212> TYPE: DNA
<213> ORGANISM: Vaccinia virus

<400> SEQUENCE: 18
cccaagctta tggcaatatt ccaaagtagc 30

<210> SEQ ID NO 19
<211> LENGTH: 36
<212> TYPE: DNA
<213> ORGANISM: Vaccinia virus

<400> SEQUENCE: 19
tggaaaacct accatggttg taagtcccca cctcaa 36

<210> SEQ ID NO 20
<211> LENGTH: 36
<212> TYPE: DNA
<213> ORGANISM: Vaccinia virus

<400> SEQUENCE: 20
tggggactta caaccatggt aggttttcca gtaaca 36

<210> SEQ ID NO 21
<211> LENGTH: 36
<212> TYPE: DNA
<213> ORGANISM: Vaccinia virus

<400> SEQUENCE: 21
tacagtctca atcattggta ctagcttgta gcacca 36

<210> SEQ ID NO 22

-continued

```
<211> LENGTH: 36
<212> TYPE: DNA
<213> ORGANISM: Vaccinia virus

<400> SEQUENCE: 22

tacaagctag taccaatgat tgagactgta ccagta                                36


<210> SEQ ID NO 23
<211> LENGTH: 36
<212> TYPE: DNA
<213> ORGANISM: Vaccinia virus

<400> SEQUENCE: 23

ccccctgcag aaaaattaag gcccaatttt tgaaat                                36
```